US007510860B1

(12) United States Patent
Sung

(10) Patent No.: US 7,510,860 B1
(45) Date of Patent: *Mar. 31, 2009

(54) XYLANASES WITH ENHANCED THERMOPHILICITY AND ALKALOPHILICITY

(75) Inventor: Wing L. Sung, Gloucester (CA)

(73) Assignee: National Research Council of Canada, Ottawa, Ontario (CA)

(*) Notice: Subject to any disclaimer, the term of this patent is extended or adjusted under 35 U.S.C. 154(b) by 684 days.

This patent is subject to a terminal disclaimer.

(21) Appl. No.: 09/990,874

(22) Filed: Nov. 21, 2001

(51) Int. Cl.
*C12N 9/26* (2006.01)
*C12P 21/06* (2006.01)
*D21C 3/00* (2006.01)
*C07H 21/04* (2006.01)

(52) U.S. Cl. .................. 435/201; 435/69.1; 435/278; 536/23.2

(58) Field of Classification Search ............ 435/183, 435/69.1, 195–211, 252.1, 254.1, 254.6, 435/320.1, 262, 262.5, 277, 278, 4, 6, 252.3, 435/252.74; 536/23.2, 23.4, 23.5, 23.7; 530/350
See application file for complete search history.

(56) References Cited

U.S. PATENT DOCUMENTS

| | | | |
|---|---|---|---|
| 5,078,802 A | 1/1992 | Imanaka et al. | |
| 5,405,769 A | 4/1995 | Campbell et al. | |
| 5,610,046 A * | 3/1997 | van Ooyen et al. | 435/200 |
| 5,759,840 A | 6/1998 | Sung et al. | |
| 5,817,500 A * | 10/1998 | Hansen et al. | 435/200 |
| 5,866,408 A | 2/1999 | Sung et al. | |
| 5,866,526 A | 2/1999 | Olsen et al. | 51/392 |
| 6,228,629 B1 * | 5/2001 | Paloheimo et al. | 435/200 |
| 2003/0166236 A1 * | 9/2003 | Sung | 435/200 |
| 2005/0271769 A1 * | 12/2005 | Sibbesen et al. | 426/20 |

FOREIGN PATENT DOCUMENTS

| | | |
|---|---|---|
| EP | 0473545 (B1) | 3/1992 |
| EP | 0 828 002 A2 | 5/1997 |
| WO | WO 94/24270 | 10/1994 |
| WO | WO 95/12668 | 5/1995 |
| WO | WO 00/29587 | 5/2000 |
| WO | WO 01/92487 A2 * | 12/2001 |

OTHER PUBLICATIONS

Kimura et al. (GenBank Accession No. Q9HFA4, Mar. 1, 2001).*
Yoshino et al. (GenBank Accession No. Q12579, Nov. 1, 1996).*
Sequence alignments of three pages.*
Arase et al. Stabilization of xylznzse by random mutagenesis. *FEBS Lett.* 316:123-127 (1993).
Chandra et al. A Cellulase-Free Xylanase From Alkali-Tolerant *Aspergillus fischeri* Fxn1. *Biotechnol. Lett.* 17:309-314 (1995).
Fisk et al. Development of A Method for the Stabilization and Formulation of Xylanase from *Trichoderma* Using Experimental Design. *Stability and Stabilization of Enzymes* published by Elsevier Science Publishers B. V. pp. 323-328 (1993).
Gruber et al. Thermophilic Xylanase from *Thermomyces lanuginosus*: High-Resolution X-ray Structure and Modeling Studies. *Biochemistry* 37:13475-13485 (1998).
Irwin et al. Characterization and Sequence of a *Thermomonospora fusca* Xylanase. *Environ. Microbiol.* 60(3):763-770 (1994).
Kinoshita et al. Cloning of the *xynNB* Gene Encoding Xylanase B from *Aspergillus niger* and Its expression in *Aspergillus kawachii. J. Fermentation and Bioengineering* 79(5):422-428 (1995).
Krengel et al. Three-dimensional Structure of Endo-1, 4-β-xylanase I from *Aspergillus niger*: Molecular Basis for its Low pH Optimum. *J. Mol. Biol.* 263:70-78 (1996).
Lee et al. Purification and Characterization of Two Endoxylanas0es from *Clostridium acetobutylicum* ATCC 824. *Appl. Environ. Microbiol.* 53(4):644-650 (1987).
Lüthi et al. Xylanase from the Extremely Thermophilic Bacterium "*Caldocellum saccharolyticum*": Overexpression of the Gene in *Escherichia coli* and Characterization. *Appl. Environ. Microbiol.* 56(9):2677-2683 (1990).
Mathrani. Thermophilic and alkalophilic xylanases from several Dictyolglomus isolates. *Appl. Microbiol. Biotechnol.* 38:23-27 (1992).
Misset, O. Stability of Industrial Enzymes. *Stability and Stabilization of Enzymes* published by Elsevier Science Publishers B. V. pp. 111-131 (1993).
Nissen et al. Xylanases for the Pulp and Paper Industry. *Xylans and Xylanases* published by Elsevier, Amsterdam, pp. 325-337 (1992 ).
Sakka et al. Nucletide Sequence of the *Clostridium stercorarium xynA* Gene Encoding Xylanase A: Identification of Catalytic and Cellulose Binding Domains. *Biosci. Biotech. Biochem.* 57(2):273-277 (1993).
Simpson et al. An extremely thermostable xylanase from the themophilic eubacterium *Thermotoga. Biochem. J.* 277:413-417 (1991).
Sung et al. Short synthetic oligodeoxyribonucleotide leader sequences enhance accumulation of human proinsulin synthesized in *Escherichia coli. Proc. Natl. Acad. Sci. USA* 83:561-565 (1986).
Sung et al. Overexpression of the *Bacillus subtilis* and circulans Xylanases in *Escherichia coli. Protein Expression Purif.* 4:200-206 (1993).
Sung et al. Expresion of *Trichoderma reesei* and *Trichoderma viride* xylanases in *Escherichia coli. Biochem. Cell. Biol.* 73:253-259 (1995).

(Continued)

*Primary Examiner*—Rebecca E. Prouty
*Assistant Examiner*—Ganapathirama Raghu
(74) *Attorney, Agent, or Firm*—Cooley Godward Kronish LLP

(57) ABSTRACT

The present invention provides a xylanase, or a modified xylanase enzyme comprising at least one substituted amino acid residue at a position selected from the group consisting of amino acid 11, 116, 118, 144 and 161, the position determined from sequence alignment of the modified xylanase with *Trichoderma reesei* xylanase II amino acid sequence. The xylanases described herein exhibit improved thermophilicity, alkalophilicity, expression efficiency, or a combination thereof, in comparison to a corresponding native xylanase.

9 Claims, 14 Drawing Sheets

OTHER PUBLICATIONS

Sunna et al. Xylanolytic Enzymes from Fungi and Bacteria. *Crit. Rev. Biotech.* 17(1):39-67 (1997).

Tolan et al. The Use of Enzymes to Decrease the $Cl_2$ Requirements in Pulp Bleaching. *Pulp & Paper Canada* 93:116-119 (1992).

Turenen et al. A combination of weakly stabilizing mutations with a disulfide bridge in the α-helix region of *Trichoderma reesei* endo-1, 4-β-xylanase II increases the thermal stability through synergiam. *J. Biotech* 88:37-46 (2001).

Wakarchuck et al. Thermostablization of the *Bacillus circulans* xylanase by the introduction of disufide bonds. *M. Protein Engineering* 7(11):1379-1386 (1994).

Winterhalter and Liebl. Two extremely Thermkostable Xylanases of the Hyperthermophilic Bacterium *Thermotoga maritima* MSB8. *Appl. Environ. Bicrobiol.* 61(5):1810-1815 (1995).

Zappe et al. Cloning and expression of a xylanase gene from *Closridium acetobutlicum* P262 in *Escherichia coli*. *Appl.Microbiol. Biotechnol.* 27:57-63 (1987).

Zappe et al. Nucleotide sequence of a *Clostridium acetobutylicum* P262 xylanase gene (*xynB*) *Nucl. Acids Res.* 18(8):2179 (1990).

Sapag et al. The endoxylanases from family 11: computer analysis of protein sequences reveals important structural and phylogenetic relationships *J. Biotech*. 95:109-131, 2002.

* cited by examiner

```
Ca      23                                                                  S AFNTQAAP    31
Cs       1                                                                    G           1

Tr2#                         10         20         30         40
                              |          |          |          |
Bp       1       RTITNNEMGN HSGYDYELWK DYGNT-SMTL NNGGAFSAGW N--NIGNA        45
Ca      10       KTITSNEIGV NGGYDYELWK DYGNT-SMTL KNGGAFSCQW S--NIGNA        54
Fs       1       NSSVTGNVG  SSPYHYEIWY QGG-NNSMTF YDNGTYKASW N--GTNDF        44
Cs       2       RIIYDNETGT HGGYDYELWK DYGNT-IMEL NDGGTFSCQW S--NIGNA        46
Rf       1       SAADQQTRGN VGGYDYEMWN QNGQGQASMN PGAGSFTCSW S--NIENF        46
Tr2      1       QTIQPGTGY  NNGYFYSYWN DGHGGVTYTN GPGGQFSVNW S--NSGNF        45
Tv       1       QTIQPGTGF  NNGYFYSYWN DGHGGVTYTN GPGGQFSVNW S--NSGNF        45
Th       1       QTIGPGTGY  SNGYYYSYWN DGHAGVTYTN GGGGSFTVNW S--NSGNF        45
Sc       1       SGTPSSTGT  DGGYYYSWWT DGAGDATYQN NGGGSYTLTW SG-NNGNL        46
An       1               S  AGINYVQNYN GNLGDFTY-D ESAGTFSMYW EDGVSSDF        38
Ak       1               S  AGINYVQNYN GNLADFTY-D ESAGTFSMYW EDGVSSDF        38
At       1               S  AGINYVQNYN QNLGDFTY-D ESAGTFSMYW EDGVSSDF        38
Tr1      1                  ASINYDQNYQ TGG-QVSYS- PSNTGFSVNW N--TQDDF        34
Aa       1       RSTPSSTGE  NNGYYYSFWT DGGGDVTYTN GNAGSYSVEW S--NVGNF        45
Ss       1       ATTIT-NETGY D-GMYYSFWT DGGGSVSMTL NGGGSYSTRW T--NCGNF       45
S1B      1       DTVVTTNQEGT NNGYYYSFWT DSQGTVSMNM GSGGQYSTSW R--NTGNF       47
S1C      1       ATTITTNQTGT D-GMYYSFWT DGGGSVSMTL NGGGSYSTQW T--NCGNF       46
Tl       1       QTTPNSEGW  HDGYYYSWWS DGGAQATYTN LEGGTYEISW G--DGGNL        45
Tf       1       AVTSNETGY  HDGYFYSFWT DAPGTVSMEL GPGGNYSTSW R--NTGNF        45
Bc       1                  ASTDYWQNWT DGGGIVNAVN GSGGNYSVNW S--NTGNF        36
Bs       1                  ASTDYWQNWT DGGGIVNAVN GSGGNYSVNW S--NTGNF        36

FIGURE 1
```

```
Tr2#              50          60          70    *    80
                   |           |           |         |
Bp     46  LFRK-GKKFD  ST-RTHHQLG  NISINYNASF  N-PSGNSYLC  VYGWTQSP   90
Ca     55  LFRK-GKKFN  DT-QTYKQLG  NISVNYNCNY  Q-PYGNSYLC  VYGWTSSP   99
Fs     45  LARV-GFKYD  EK-HTYEELGPIDAYYKWSKQ   GSAGGYNYIG  IYGWTVDP   91
Cs     47  LFRK-GRKFN  SD-KTYQELG  DIVVEYGCDY  N-PNGNSYLC  VYGWTRNF   91
Rf     47  LARM-GKNYD  SQKKNYKAFG  NIVLTYDVEY  T-PRGNSYMC  VYGWTRNP   92
Tr2    46  VGGK-GWQPG  TKNKV-----  ---INFS-GS  YNPNGNSYLS  VYGWSRNP   83
Tv     46  VGGK-GWQPG  TKNKV-----  ---INFS-GS  YNPNGNSYLS  VYGWSRNP   83
Th     46  VGGK-GWQPG  TKNKV-----  ---INFS-GS  YNPNGNSYLS  IYGWSRNP   83
Sc     47  VGGK-GWNPG  AASRS-----  ---ISYS-GT  YQPNGNSYLS  VYGWTRSS   84
An     39  VVGL-GWTTG  SSNA------  ---ITYSAEY  SASGSSSYLA  VYGWVNYP   76
Ak     39  VVGL-GWTTG  SSNA------  ---ISYSAEY  SASGSSSYLA  VYGWVNYP   76
At     39  VVGLGGWTTG  SSNA------  ---ITYSAEY  SASGSASYLA  VYGWVNYP   77
Tr1    35  VVGV-GWTTG  SSAP------  ---INFGGSF  SVNSGTGLLS  VYGWSTNP   72
Aa     46  VGGK-GWNPG  SAKD------  ---ITYSGNF  T-PSGNGYLS  VYGWTTDP   82
Ss     46  VAGK-GWANG  GR-RT-----  ---VRYT-GW  FNPSGNGYGC  LYGWTSNP   82
S1B    48  VAGK-GWANG  GR-RT-----  ---VQYS-GS  FNPSGNAYLA  LYGWTSNP   84
S1C    47  VAGK-GWSTG  DGN-------  ---VRYN-GY  FNPVGNGYGC  LYGWTSNP   82
Tl     46  VGGK-GWNPG  LNARA-----  ---IHFE-GV  YQPNGNSYLA  VYGWTRNP   83
Tf     46  VAGK-GWATG  GR-RT-----  ---VTYS-AS  FNPSGNAYLT  LYGWTRNP   82
Bc     37  VVGK-GWTTG  SPFRT-----  ---INYNAGV  WAPNGNGYLT  LYGWTRSP   75
Bs     37  VVGK-GWTTG  SPFRT-----  ---INYNAGV  WAPNGNGYLT  LYGWTRSP   75

Tr2#              90         100    *    110         120         130
                   |           |           |           |           |
Bp     91  LAEYYIVDSW  GTYR-PT--G  AYKGSFYADG  GTYDIYETTR  VNQPSIIG  135
Ca    100  LVEYYIVDSW  GSWRPP--GG  TSKGTITVDG  GIYDIYETTR  INQPSIQG  145
Fs     92  LVEYYIVDDW  FNKPGANLLG  QRKGEFTVDG  DTYEIWQNTR  VQQPSIKG  139
Cs     92  LVEYYIVESW  GSWRPP--GA  TPKGTITQWMAGTYEIYETTR  VNQPSIDG  138
Rf     93  LMEYYIVEGW  GDWRPPGNDG  EVKGTVSANG  NTYDIRKTMR  YNQPSLDG  140
Tr2    84  LIEYYIVENF  GTYN-PSTGA  TKLGEVTSDG  SVYDIYRTQR  VNQPSIIG  130
Tv     84  LIEYYIVENF  GTYN-PSTGA  TKLGEVTSDG  SVYDIYRTQR  VNQPSIIG  130
Th     84  LIEYYIVENF  GTYN-PSTGA  TKLGEVTSDG  SVYDIYRTQR  VNQPSIIG  130
Sc     85  LIEYYIVESY  GSYD-PSSAA  SHKGSVTCNG  ATYDILSTWR  YNAPSIDG  131
An     77  GAEYYIVEDY  GDYN-PCSSA  TSLGTVYSDG  STYQVCTDTR  INEPSITG  123
Ak     77  QAEYYIVEDY  GDYN-PCSSA  TSLGTVYSDG  STYQVCTDTR  TNEPSITG  123
At     78  QAEYYIVEDY  GDYN-PCSSA  TSLGTVYSDG  STYQVCTDTR  INEPSITG  124
Tr1    73  LVEYYIMEDN  HNY--PAQ-G  TVKGTVTSDG  ATYTIWENTR  VNEPSIQG  117
Aa     83  LIEYYIVESY  GDYN-PGSGG  TTRGNVSSDG  SVYDIYTATR  TNAPSIDG  129
Ss     83  LVEYYIVDNW  GSYR-PT--G  ETRGTVHSDG  GTYDIYKTTR  YNAPSVEA  127
S1B    85  LVEYYIVDNW  GTYR-PT--G  EYKGTVTSDG  GTYDIYKTTR  VNKPSVEG  129
S1C    83  LVEYYIVDNW  GSYR-PT--G  TYKGTVSSDG  GTYDIYQTTR  YNAPSVEG  127
Tl     84  LVEYYIVENF  GTYD-PSSGA  TDLGTVECDG  SIYRLGKTTR  VNAPSIDG  130
Tf     83  LVEYYIVESW  GTYR-PT--G  TYMGTVTTDG  GTYDIYKTTR  YNAPSIEG  127
Bc     76  LIEYYVVDSW  GTYR-PT--G  TYKGTVKSDG  GTYDIYTTTR  YNAPSIDG  120
Bs     76  LIEYYVVDSW  GTYR-PT--G  TYKGTVKSDG  GTYDIYTTTR  YNAPSIDG  120
```

FIGURE 1 CONT'D

```
Tr2#                    140         150         160
                         |           |           |
Bp   136  -IATFKQYWS  VRQTKRTS--  ------GTVS  VSAHFRKWES  LGMPM-GK  173
Ca   146  -NTTFKQYWS  VRRTKRTS--  ------GTIS  VSKHFAAWES  KGMPL-GK  183
Fs   140  -TQTFPQYFS  VRKSARSC--  ------GHID  ITAHMKKWEE  LGMKM-GK  177
Cs   139  -TATFQQYWS  VRTSKRTS--  ------GTIS  VTEHFKQWER  MGMRM-GK  176
Rf   141  -TATFPQYWS  VRQTSGSANN  QTNYMKGTID  VSKHFDAWSA  AGLDMSGT  187
Tr2  131  -TATFYQYWS  VRRNHR-S-S  ------GSVN  TANHFNAWAQ  QGLTL-GT  168
Tv   131  -TATFYQYWS  VRRTHR-S-S  ------GSVN  TANHFNAWAQ  QGLTL-GT  168
Th   131  -TATFYQYWS  VRRNHR-S-S  ------GSVN  TANHFNAWAS  HGLTL-GT  168
Sc   132  -TQTFEQFWS  VRNPKKAPGG  SIS---GTVD  VQCHFDAWKG  LGMNLGSE  175
An   124  -TSTFTQYFS  VRESTRTS--  ------GTVT  VANHFNFWAQ  HGFGN-SD  161
Ak   124  -TSTFTQYFS  VRESTRTS--  ------GTVT  VANHFNFWAQ  HGFGN-SD  161
At   125  -TSTFTQYFS  VRESTRTS--  ------GTVT  VANHFNFWAH  HGFHN-SD  163
Trl  118  -TATFNQYIS  VRNSPR-T-S  ------GTVT  VQNHFN-WAS  LGLHLGQM  155
Aa   130  -TQTFSQYWS  VRQNKR-VG-  ------GTVT  TSNHFNAWAK  LGMNL-GT  167
Ss   128  -PAAFDQYWS  VRQSKVT--S  ------GTIT  TGNHFDAWAR  AGMNMGNF  166
S1B  130  TR-TFDQYWS  VRQSKR-TG-  ------GTIT  TGNHFDAWAR  AGMPLGNF  168
S1C  128  TK-TFQQYWS  VRQSKVTSGS  ------GTIT  TGNHFDAWAR  AGMNMGQF  168
Tl   131  TQ-TFDQYWS  VRQDKR-T-S  ------GTVQ  TGCHFDAWAR  AGLNVNGD  169
Tf   128  TR-TFDQYWS  VRQSKRTS--  ------GTIT  AGNHFDAWAR  HGMHLGTH  166
Bc   121  DRTTFTQYWS  VRQSKRPTGS  N-----ATIT  FTNHVNAWKS  HGMNLGSN  163
Bs   121  DRTTFTQYWS  VRQSKRPTGS  N-----ATIT  FSNHVNAWKS  HGMNLGSN  163

Tr2#         170         180         190
              |           |           |
Bp   174  MYETAFTVEG  YQSSGSANVM  TNQLFIGN         201  SEQ ID NO:4
Ca   184  MHETAFNIEG  YQSSGKADVN  SMSINIGK         211  SEQ ID NO:6
Fs   178  MYEAKVLVEA  GGGSGSFDV-  TYFKMT           202  SEQ ID NO:18
Cs   177  MYEVALTVEG  YQSSGYANVY  KNEIRIGANP....        SEQ ID NO:7
Rf   188  LYEVSLNIEG  YRSNGSANVK  SVSV             211  SEQ ID NO:8
Tr2  169  MDYQIVAVEG  YFSSGSASI-  TVS              190  SEQ ID NO:16
Tv   169  MDYQIVAVEG  YFSSGSASI-  TVS              190  SEQ ID NO:17
Th   169  MDYQIVAVEG  YFSSGSASI-  TVS              190  SEQ ID NO:14
Sc   176  HNYQIVATEG  YQSSGTATI-  TVT              197  SEQ ID NO:9
An   162  FNYQVMAVEA  WSGAGSASV-  TISS             184  SEQ ID NO:1
Ak   162  FNYQVMAVEA  WSGAGSASV-  TISS             184  SEQ ID NO:54
At   164  FNYQVVAVEA  WSGAGSAAV-  TISS             185  SEQ ID NO:2
Trl  156  MNYQVVAVEG  WGGSGSASQ-  SVSN             178  SEQ ID NO:15
Aa   168  HNYQILATEG  YQSSGSSSI-  TIQ              189  SEQ ID NO:19
Ss   167  RYYMINATEG  YQSSGSSTI-  TVSG             189  SEQ ID NO:12
S1B  169  SYYMINATEG  YQSSGTSSI-  NVGG..........        SEQ ID NO:10
S1C  169  RYYMINATEG  YQSSGSSNI-  TVSG             191  SEQ ID NO:11
Tl   170  HYYQIVATEG  YFSSGYARI-  TVADVG           194  SEQ ID NO:20
Tf   167  D-YMIMATEG  YQSSGSSNVT  LGTS..........        SEQ ID NO:13
Bc   164  WAYQVMATEG  YQSSGSSNV-  TVW              185  SEQ ID NO:3
Bs   164  WAYQVMATEG  YQSSGSSNV-  TVW              185  SEQ ID NO:5
```

FIGURE 1 CONT'D

```
                                                                         st
                                            5'-CT AGC TAA GGA GG CTG CAG ATG
                                                  G ATT CCT CC GAC GTC TAC
                                                NheI |              PstI

TrX-1
    1   2   3   4   5   6   7   8   9  10  11  12  13  14  15  16
    Q   T   I   Q   P   G   T   G   Y   N   N   G   Y   F   Y   S
   CAA ACA ATA CAA CCA GGA ACC GGT TAC AAC AAC GGT TAC TTT TAC AGC
   GTT TGT TAT GTT GGT CCT TGG CCA ATG TTG TTG CCA ATG AAA ATG TCG
                TrX-8           AgeI                     |

XyTv-2
   17  18  19  20  21  22  23  24  25  26  27  28  29  30  31  32
    Y   W   N   D   G   H   G   G   V   T   Y   T   N   G   P   G
   TAT TGG AAC GAT GGC CAT GGT GGT GTT ACC TAT ACA AAC GGG CCC GGA
   ATA ACC TTG CTA CCG GTA CCA CCA CAA TGG ATA TGT TTG CCC GGG CCT
                         NcoI                    XyTv-7     ApaI

|
   33  34  35  36  37  38  39  40  41  42  43  44  45  46  47  48
    G   Q   F   S   V   N   W   S   N   S   G   N   F   V   G   G
   GGC CAA TTT AGC GTC AAT TGG TCT AAC TCC GGA AAC TTC GTA GGT GGA
   CCG GTT AAA TCG CAG TTA ACC AGA TTG AGG CCT TTG AAG CAT CCA CCT
                         MunI    |       BspEI

TrX-3
   49  50  51  52  53  54  55  56  57  58  59  60  61  62  63  64
    K   G   W   Q   P   G   T   K   N   K   V   I   N   F   S   G
   AAA GGT TGG CAA CCC GGG ACC AAA AAT AAG GTG ATC AAC TTC TCT GGA
   TTT CCA ACC GTT GGG CCC TGG TTT TTA TTC CAC TAG TTG AAG AGA CCT
                         XmaI                    TrX-6

|
   65  66  67  68  69  70  71  72  73  74  75  76  77  78  79  80
    S   Y   N   P   N   G   N   S   Y   L   S   V   Y   G   W   S
   TCT TAT AAT CCG AAT GGG AAT TCA TAC TTA AGC GTC TAT GGC TGG TCT
   AGA ATA TTA GGC TTA CCC TTA AGT ATG AAT TCG CAG ATA CCG ACC AGA
    |                      EcoRI    AflII

XyTv-4                                                       |
   81  82  83  84  85  86  87  88  89  90  91  92  93  94  95
    R   N   P   L   I   E   Y   Y   I   V   E   N   F   G   T
   AGA AAC CCA CTG ATT GAA TAT TAC ATT GTC GAA AAT TTC GGT AC
   TCT TTG GGT GAC TAA CTT ATA ATG TAA CAG CTT TTA AAG C
   Xba I            XyTv-5                                  | KpnI
```

FIGURE 2

```
                                    XyTv-101
          92  93  94  95  96  97  98  99 100 101 102 103 104 105
      V   D   N   F   G   T   Y   N   P   S   T   G   A   T   K   L
     TC GAC AAT TTC GGT ACC TAC AAT CCG AGT ACC GGC GCC ACA AAA TTA
      3'-G TTA AAG CCA TGG ATG TTA GGC TCA TGG CCG CGG TGT TTT AAT
     SalI          KpnI            XyTv-110    KasI/NarI

XyTv-102
    106 107 108 109 110 111 112 113 114 115 116 117 118 119 120 121
     G   E   V   T   S   D   G   S   V   Y   D   I   Y   R   T   Q
    GGC GAA GTC ACT AGT GAT GGA TCC GTA TAT GAT ATC TAC CGT ACC CAA
    CCG CTT CAG TGA TCA CTA CCT AGG CAT ATA CTA TAG ATG GCA TGG GTT
                    SpeI        BamHI                    XyTv-109
                         |                     TrX-103
    122 123 124 125 126 127 128 129 130 131 132 133 134 135 136 137
     R   V   N   Q   P   S   I   I   G   T   A   T   F   Y   Q   Y
    CGC GTT AAT CAG CCA TCG ATC ATT GGA ACC GCC ACC TTT TAT CAG TAC
    GCG CAA TTA GTC GGT AGC TAG TAA CCT TGG CGG TGG AAA ATA GTC ATG
    MluI                ClaI 138 139 140 141 142 143 144 145 146 147 148 149 150 151 152 153
     W   S   V   R   R   N   H   R   S   S   G   S   V   N   T   A
    TGG AGT GTT AGA CGT AAT CAT CGG AGC TCC GGT TCG GTT AAT ACT GCG
    ACC TCA CAA TCT GCA TTA GTA GCC TCG AGG CCA AGC CAA TTA TGA CGC
         TrX-108                        SacI

XyTv-104
    154 155 156 157 158 159 160 161 162 163 164 165 166 167 168 169
     N   H   F   N   A   W   A   Q   Q   G   L   T   L   G   T   M
    AAT CAC TTT AAT GCA TGG GCA CAG CAA GGG TTA ACC CTA GGT ACA ATG
    TTA GTG AAA TTA CGT ACC CGT GTC GTT CCC AAT TGG GAT CCA TGT TAC
                     NsiI         XyTv-107              AvrII

XyTv-105
    170 171 172 173 174 175 176 177 178 179 180 181 182 183 184 185
     D   Y   Q   I   V   A   V   E   G   Y   F   S   S   G   S   A
    GAT TAT CAA ATC GTA GCG GTG GAA GGC TAC TTC TCG AGT GGT TCC GCT
    CTA ATA GTT TAG CAT CGC CAC CTT CCG ATG AAG AGC TCA CCA AGG CGA
                             XyTv-106             XhoI 186 187 188 189 190
     S   I   T   V   S
    AGT ATT ACA GTG AGC TAA A              SEQ ID NO:16
    TCA TAA TGT CAC TCG ATT TCT AG-5'      SEQ ID NO:39
                        BglII
```

FIGURE 2 CONT'D

XYLANASES WITH ENHANCED THERMOPHILICITY AND ALKALOPHILICITY

The present invention relates to xylanases. More specifically, the invention relates to xylanases, and modified xylanases with improved performance at conditions of high temperature and pH.

BACKGROUND OF THE INVENTION

Xylanases are a group of enzymes with side commercial utility. A major application of xylanases is for pulp biobleaching in the production of paper. In addition, xylanases have been used as clarifying agents in juices and wines, as enzymatic agents in the washing of precision devices and semiconductors (e.g. U.S. Pat. No. 5,078,802), and they are also used for improving digestibility of poultry and swine feed.

In the manufacturing of pulp for the production of paper, fibrous material is subjected to high temperatures and pressures in the presence of chemicals. This treatment converts the fibers to pulp and is known as pulping. Following pulping, the pulp is bleached. Xylanase enzymes are used to enhance the bleaching of the pulp. The xylanase treatment allows subsequent bleaching chemicals such as chlorine, chlorine dioxide, hydrogen peroxide, or combinations of these chemicals to bleach pulp more efficiently. Pretreatment of pulp with xylanase increases the whiteness and quality of the final paper product and reduces the amount of chlorine-based chemicals which must be used to bleach the pulp. This in turn decreases the chlorinated effluent produced by such processes.

The most important chemical pulping process is kraft pulp. For kraft pulp, following pulping, and prior to the treatment of pulp with xylanase, the pulp is at about a temperature of 55-70° C. and at a highly alkaline pH (e.g. Nissen et al., 1992). A drawback of many commercially available wild-type xylanases, is that these enzymes exhibit an acidic pH optimum and a temperature optimum of about 55° C. Therefore, in order to effectively utilize xylanases for bleaching applications, the pulp must be acidified to a pH approximating the optimal pH for the specific xylanase used. In addition, the hot pulp must be cooled to a temperature close to the optimal temperature for enzymatic activity of the selected xylanase. Decreasing pulp temperatures for xylanase treatment decreases the efficiency of the subsequent chemical bleaching. Acidification of pulp requires the use of large quantities of acids. Further, the addition of acids leads to corrosion, which lessens the lifetime of process equipment. Thus, xylanases optimally active at temperatures and pH conditions approximating the conditions of the pulp would be useful and beneficial in pulp manufacturing.

Xylanases which exhibit greater activity at higher temperatures could be used to treat pulp immediately following the pulping process, without the need to cool the pulp. Similarly, xylanases which exhibit greater activity at higher pH conditions would require less or no acid to neutralize the pulp. The isolation of, or the genetic manipulation of, xylanases with such properties would provide several advantages and substantial economic benefits within a variety of industrial processes.

Several approaches directed towards improving xylanase for use in pulp-bleaching within the prior art include the isolation of thermostable xylanases from extreme thermophiles that grow at 80-100° C., such as *Caldocelium saccharolyticum, Thermatoga maritima* and *Thermatoga* sp. Strain FJSS-B.1 (Lüthi et al. 1990; Winterhalter et al. 1995; Simpson et al. 1991). However, these thermostable xylanase enzymes are large, with molecular masses ranging from 35-120 kDa (320-1100 residues), and exhibit a reduced ability to penetrate the pulp mass compared with other smaller xylanases which exhibit better accessibility to pulp fibers. In addition, some of the extremely thermophilic xylanases, such as *Caldocellum saccharolyticum* xylanase A, exhibit both xylanase and cellulase activities (Lüthi et al. 1990). This additional cellulolytic activity is undesirable for pulp bleaching, due to its detrimental effect of cellulose, the bulk material in paper. Furthermore, hyper-thermostable xylanase enzymes which function normally at extremely high temperatures have low specific activities at temperatures in the range for optimal pulp bleaching (Simpson et al. 1991).

A number of xylanases have been modified by protein engineering to improve their properties for industrial applications. For instance, U.S. Pat. No. 5,759,840 (Sung et al.), and U.S. Pat. No. 5,866,408 (Sung et al.) disclose mutations in the N-terminal region (residues 1-29) of *Trichoderma reesei* xylanase II (TrX). Three mutations, at residues 10, 27 and 29 of TrX, were found to increase the enzymatic activity of the xylanase enzyme at elevated temperatures and alkaline pH conditions.

U.S. Pat. No. 5,405,769 (Campbell et al.) discloses modification of *Bacillus circulans* xylanase (BcX) using site-directed mutagenesis to improve the thermostability of the enzyme. The site specific mutations include replacing two amino acids with Cys residues to create intramolecular disulfide bonds. In addition, specific residues in the N-terminus of the enzyme were mutated which were also found to further improve the thermostability of the enzyme. In in vitro assays, the disulfide mutants showed thermostability at 62° C., an improvement of 7° C. over the native BcX xylanase enzyme. However, these thermostable disulfide mutants showed no gain in thermophilicity in laboratory assays in subsequent studies (Wakarchuck et al., 1994). Mutations T3G (i.e. threonine at position 3 replaced with Gly; BcX xylanase amino acid numbering), D4Y(F) and N8Y(F) near the N-terminus of the BcX xylanase enzyme provided thermostability to 57° C., an increase of 2° C. over the native BcX (U.S. Pat. No. 5,405,769). However, the use of these enzymes within industrial applications still requires cooling and acidification of pulp following pretreatment, prior to enzyme addition. Therefore, further increases in thermostability, thermophilicity and pH optima are still required.

Turunen et al. (2001) discloses mutations (N11D, N38E, Q162H) of TrX II at positions 11, 38 and 162, complement similar disulfide bond (S110C/N154C) to improve the thermostability of the xylanase. However, these mutations including N11D also have an adverse effect on both the thermophilicity and the alkalophilicity of the xylanase, resulting in a decrease of enzymatic activity at higher temperatures and the neutral-alkaline pH, as compared to native TrX II.

There is a need in the prior art to obtain novel xylanases which exhibit increased enzymatic activity at elevated temperatures and pH conditions, suitable for industrial use. It is an object of the invention to overcome drawbacks in the prior art.

The above object is met by the combination of features of the main claim, the sub-claims disclose further advantageous embodiments of the invention.

SUMMARY OF THE INVENTION

The present invention relates to xylanases. More specifically, the invention relates to xylanases, and modified xylanases with improved performance at conditions of high temperature and pH.

This invention relates to a xylanase comprising at least one substituted amino acid residue at a position selected from the group consisting of amino acid 11, 116, 118, 144, and 161, with the position determined from sequence alignment of the modified xylanase with *Trichoderma reesei* xylanase II amino acid sequence defined in SEQ ID NO:16. Preferably, the xylanase exhibits improved thermophilicity, alkalophilicity, broader effective pH range, expression efficiency or a combination thereof, in comparison to a corresponding native TrX xylanase.

The present invention also provides for the xylanase as defined above wherein the xylanase is a modified xylanase and at least one substituted amino acid residue is at position 116. Preferably the substituted amino acid is Gly.

The present invention also embraces the xylanase, modified at position 116 as defined above and further comprising a His at positions 10 and 105, a Met at position 27, a Leu at position 29, an Ala at positions 75 and 125, a Glu at position 129 and a Arg at position 144.

This invention includes the xylanase modified at position 116 as defined above and further comprising a His at positions 10 and 105, a Met at position 27, a Leu at position 29, an Ala at positions 75 and 125, a Glu at position 129 and a Arg at position 144.

This invention describes the xylanase modified at position 116 as defined above and further comprising a His at positions 10 and 105, an Asp at position 11, a Met at position 27, a Leu at position 29, an Ala at positions 75 and 125, a Glu at position 129 and a Arg at positions 144 and 161.

The present invention also provides for the modified xylanase as defined above wherein the at least one substituted amino acid residue is at position 144. Preferably the substituted amino acid is Arg.

The present invention embraces the xylanase modified at position 144 as defined above and further comprising a His at positions 10 and 105, a Met at position 27, a Leu at position 29, an Ala at positions 75 and 125 and a Glu at position 129.

The present invention also provides for the modified xylanase as defined above wherein the at least one substituted amino acid residue is at position 61. Preferably the substituted amino acid is Arg.

The present invention embraces the xylanase modified at position 161 as defined above and further comprising a His at positions 10 and 105, a Met at position 27, a Leu at position 29, an Ala at positions 75 and 125, a Glu at position 129 and an Arg at position 144.

The present invention also provides for the modified xylanase as defined above wherein the at least one substituted amino acid residue is at position 11. Preferably the substituted amino acid is Asp.

The present invention embraces the xylanase modified at position 11 as defined above and further comprising a His at positions 10 and 105, a Met at position 27, a Leu at position 29, an Ala at positions 75 and 125, a Glu at position 129 and an Arg at positions 144 and 161.

The present invention also provides for the modified xylanase as defined above wherein the at least one substituted amino acid residue is at position 118. Preferably the substituted amino acid is Cys.

The present invention also embraces the xylanase modified at position 118 as defined above and further comprising a His at positions 10 and 105, a Met at position 27, a Leu at position 29, an Ala at positions 75 and 125, a Glu at position 129 and a Arg at position 144.

The present invention includes the xylanase modified at position 118 as defined above and further comprising a His at positions 10 and 105, a Met at position 27, a Leu at position 29, an Ala at positions 75 and 125, a Glu at position 129 and a Arg at position 144.

This invention describes the xylanase modified at position 118 as defined above and further comprising a His at positions 10 and 105, an Asp at position 11, a Met at position 27, a Leu at position 29, an Ala at positions 75 and 125, a Glu at position 129 and a Arg at positions 144 and 161.

The present invention is also directed to the modified xylanases, as defined above, wherein the modified xylanases are derived from a Family 11 xylanase, preferably a *Trichoderma reesei* xylanase.

The present invention pertains to a modified xylanase comprising at least one substituted amino acid residue, wherein the modified xylanase is characterized as having a maximum effective temperature (MET) between about 69° C. to about 84° C., and wherein the modified xylanase is a Family 11 xylanase obtained from a *Trichoderma* sp. Preferably, the MET is between about 70° C. to about 80° C.

This invention also includes a modified xylanase comprising at least one substituted amino acid residue, wherein the modified xylanase is characterized as having a maximum effective pH (MEP) between about pH 5.8 to about pH 8.4, and wherein the modified xylanase is a Family 11 xylanase obtained from a *Trichoderma* sp. Preferably, the MEP is between about pH 6.0 to about pH 8.0.

The present invention is directed to a modified xylanase comprising at least one substituted amino acid residue, wherein the modified xylanase is characterized as having a maximum effective temperature (MET) between about 69° C. to about 84° C., and a maximum effective pH (MEP) between about pH 5.8 to about pH 8.4 Prefereably, the MET is between about 70° C. to about 80° C., and the MEP is between about pH 6.0 to about pH 8.0.

The present invention also relates to a modified xylanase selected from the group consisting of:
 TrX-HML-75A105H-125A129E-144R;
 TrX-HML-75A105H-125A129E-144R161R;
 TrX-116G;
 TrX-118C;
 TrX-HML-75A105H-116G-125A129E-144R;
 TrX-HML-75A105H-118C-125A129E-144R;
 TrX-H-11D-ML-75A105H-125A129E-144R161R;
 TrX-H-11D-ML-75A105H-116G-125A129E-144R161R;
 TrX-H-11D-ML-75A105H-118C-125A129E-144R161R; and
 TrX-H-11D-ML-75A105H-116G118C-125A129E-144R161R;

According to the present invention, there is also provided a modified xylanase comprising at least one substituted amino acid residue, and characterized as having a maximum effective temperature (MET) between about 69° C. to about 84° C., wherein the modified xylanase is a Family 11 xylanase obtained from a *Trichoderma* sp. Furthermore the present invention relates to a modified Family 11 xylanase obtained from a *Trichoderma* sp. characterized as having a MET between about 70° C. to about 80° C. The present invention also includes the modified Family 11 xylanase obtained from a *Trichoderma* sp. characterized as having a MET between about 69° C. to about 84° C. and a maximum effective pH (MEP) between about 5.8 to about 8.4. This invention also pertains to the modified xylanase as just defined, wherein the MEP is between about 6.0 to about 8.0.

The present invention is directed to the use of the modified xylanase as defined above in an industrial process. Also included is an industrial process, wherein the industrial process comprises bleaching of pulp, processing of precision devices, or improving digestibility of poultry and swine feed.

This summary of the invention does not necessarily describe all necessary features of the invention but that the invention may also reside in a subcombination of the described features.

BRIEF DESCRIPTION OF THE DRAWINGS

These and other features of the invention will become more apparent from the following description in which reference is made to the appended drawings wherein:

FIG. 1 shows an amino acid sequence alignment among Family 11 xylanases. The amino acid numbering is compared with *Trichoderma reesei* xylanase II (Tr2) as indicated at the top of the sequences. The residues at position 75 and 105 (relative to Tr2) are in italic and indicated with an asterisk. The amino acids common to at least 75% of the listed Family 11 xylanases are indicated in bold. The residues common to all Family 11 xylanases are underlined. For xylanases with a cellulose-binding domain, only the catalytic core sequences are presented. Bp: *Bacillus pumilus* (SEQ ID NO:4); Ca: *Clostridium acetobutylicum pl P262* XynB (SEQ ID NO:6); Cs: *Clostridium stercorarium* xynA (SEQ ID NO:7); Rf: *Ruminococcus flavefaciens* (SEQ ID NO:8); Tr2 *Trichoderma reesei* XYN II (SEQ ID NO:16); Tv: *Trichoderma viride* (SEQ ID NO:17); Th: *Trichoderma harzianum* (SEQ ID NO:14); Sc: *Schizophyllum commune* Xylanase A (SEQ ID NO:9); An: *Aspergillus niger,* var. *awamori* (SEQ ID NO:1); Ak: *Aspergillus kawachii* XynC (SEQ ID NO:54); At: *Aspergillus tubigensis* (SEQ ID NO:2); Trl; *Trichoderma reesei* XYN I (SEQ ID NO:15); Aa: *Aspargillus awamorivar* var. *kawachi* Xyn B (SEQ ID NO:19); Fs: *Fibrobacter succinogenes* XYN II (SEQ ID NO:18); Ss: *Streptomyces* sp. 36a (SEQ ID NO:12); SlB: *Streptomyces lividans* Xln B (SEQ ID NO:10); SlC: *Streptomyces lividans* Xln C (SEQ ID NO:11); Tl: *Thermomyces lanuginosus* Xyn (SEQ ID NO:20); Tf: *Thermomonospora fusca* TfxA (SEQ ID NO:13); Bc: *Bacillus circulans* (SEQ ID NO:3); Bs: *Bacillus subtilis* (SEQ ID NO:5).

FIG. 2 shows the nucleotide sequence of TrX xylanase (SEQ ID NO:39), and the synthetic oligonucleotides used to construct the sequence encoding the *Trichoderma reesei* xylanase II enzyme (TrX) in the plasmid pTrX.

DESCRIPTION OF PREFERRED EMBODIMENT

Figure 3:
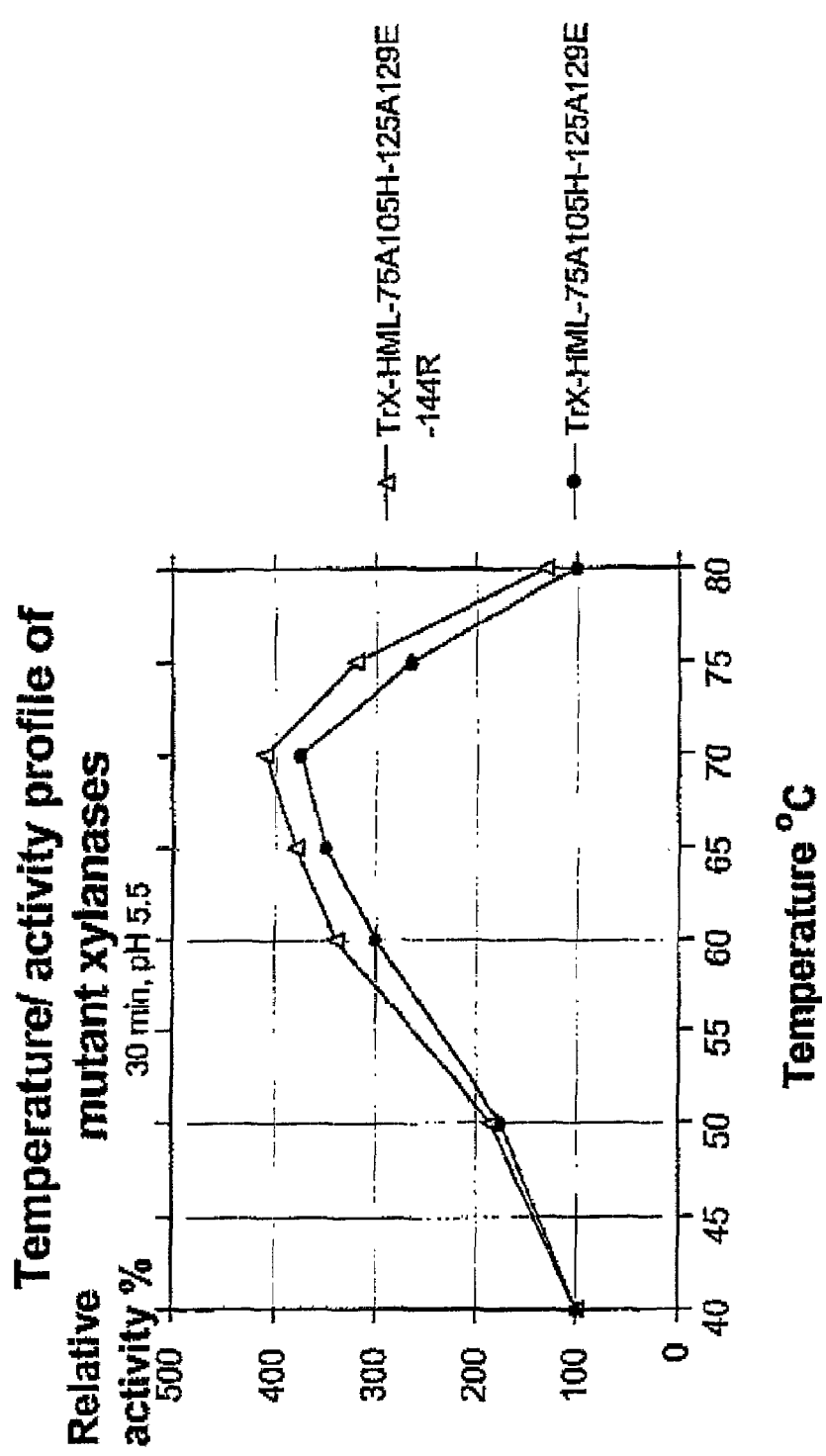
FIG. 3 shows the effect of temperature on the enzymatic activity of modified xylanase TrX-HML-75A105H-125A129E-144R, compared with TrX-HML-75A105H-125A129E, at pH 5.5 during 30-min incubations. The data are normalized to the activity observed at 40° C.

The present invention relates to xylanases. More specifically, the invention relates to xylanase and modified xylanases with improved performance at conditions of high temperature and pH.

The following description is of a preferred embodiment by way of example only and without limitation to the combination of features necessary for carrying the invention into effect.

The mechanism by which xylanases facilitate bleaching of pulp is not fully understood. It has been postulated that the coloured lignin is connected to crystalline cellulose through xylan and xylanase enzymes facilitate bleaching of pulp by hydrolysing xylan, releasing coloured lignin in the pulp. Xylanases and modified xylanases, as outlined herein, may be used for the purposes of bleaching pulp or other applications requiring activities at temperatures and pH above that of the wild-type enzyme. For the biobleaching of pulp, the preferred temperature is derived from a xylanase classified in Family 11 (see Table 1), however, the modifications disclosed herein need not be limited to only Family 11 xylanases and may include other xylanase enzymes. Furthermore, the modifications as outlined herein may be found in native xylanase proteins, and these native xylanase enzymes may exhibit the desired features as described herein, and are included within the present invention.

Family 11 xylanase enzymes are a group of small enzymes of relatively low molecular mass (approximately 20 kDa, and about 200 amino acid residues. The small size associated with Family 11 xylanases permits ready penetration of the pulp mass. Furthermore, Family 11 xylanases are free of cellulase activity.

One aspect of the present invention is directed to a modified Family 11 xylanase obtained from a *Trichoderma* sp. comprising at least one substituted amino acid residue, and characterized as having a maximum effective temperature (MET; see definition below) between about 69° C. to about 84° C. Preferably, the modified xylanase is characterized as having a MET between about 70° C. to about 80° C. This invention also includes a modified xylanase comprising at least one substituted amino acid residue, and is characterized as having a maximum effective pH (MEP; see definition below) between about 5.8 to about 8.4. Preferably, the MEP is between about 6.0 to about 8.0.

This invention also pertains to a modified xylanase obtained from *Trichoderma*, comprising at least one substituted amino acid, and characterized as having a maximum effective temperature (MET) between about 69° C. to about 84° C., and a maximum effective pH (MEP) between about 5.8 to about 8.4. Preferably the MET is between about 70° to about 80° C., and the MEP is between about 6.0 to about 8.0.

This invention also pertains to a native family 11 xylanase characterized as having a maximum effective temperature (MET) between about 69° C. to about 84° C., and a maximum effective pH (MEP) between about 5.8 to about 8.4. Preferably the MET is between about 70° C. to about 80° C., and the MEP is between about 6.0 to about 8.0.

By "maximum effective temperature" or "MET" it is meant the highest temperature at which a xylanase exhibits at least 80% of its optimal activity. This test is typically carried out using soluble birchwood xylan as a substrate at pH 5.5 or 6.0, and for a 30 min period. Results from assays used to characterize modified xylanases are presented in FIGS. 3 to 8 and involved a 30-min incubation at pH 5.5 or 6.0. A summary of the MET of several enzymes of the present invention, determined from FIGS. 3 to 8 is presented in FIG. 11. Experiments demonstrate that the MET of a xylanase differs on different substrates. Therefore, it is to be understood that with different substrates, different MET values will be obtained (data not presented). For the purposes of evaluating xylanases of the present invention, the soluble birchwood xylan substrate is used (see example 3).

By "maximum effective pH" or "MEP" it is meant the highest pH at which a xylanase exhibits at least 80% of its optimal activity. This test is carried out using soluble birchwood xylan as a substrate, at 65° C., and for a 30-min period. Results from assays used to characterize modified xylanases are presented in FIGS. 9 and 10 and involved a 30-min incubation at 65° C. A summary of the MEP of several enzymes of the present invention is presented in FIG. 11.

Experiments demonstrate that the MEP of a xylanase differs on different substrates. For example, on kraft pulp prepared from soft wood or hardwood, a MEP of 9.2 has been observed (data not presented). Therefore, it is to be understood that with different substrates, different MEP values will be obtained. For the purposes of evaluating xylanases of the present invention, the soluble birchwood xylan substrate is used (see example 4).

TABLE 1

Family 11 xylanase enzymes

| Microbe | Xylanase | SEQ ID NO |
|---|---|---|
| *Aspergillus niger* | Xyn A | SEQ ID NO: 1 |
| *Aspargillus awamari var. kawachi* | Xyn B | SEQ ID NO: 19 |
| *Aspergillus kawachii* | Xyn C | — |
| *Aspergillus tubigensis* | Xyn A | SEQ ID NO: 2 |
| *Bacillus circulans* | Xyn A | SEQ ID NO: 3 |
| *Bacillus pumilus* | Xyn A | SEQ ID NO: 4 |
| *Bacillus subtilis* | Xyn A | SEQ ID NO: 5 |
| *Cellulomonas fimi* | Xyn D | — |
| *Chainia spp.* | Xyn | — |
| *Clostridium acetobutylicum* | Xyn B | SEQ ID NO: 6 |
| *Clostridium stercorarium* | Xyn A | SEQ ID NO: 7 |
| *Fibrobacter succinognees* | Xyn II | SEQ ID NO: 18 |
| *Neocallimasterix patriciarum* | Xyn A | — |
| *Nocardiopsis dassonvillei* | Xyn II | — |
| *Ruminococcus flavefaciens* | Xyn A | SEQ ID NO: 8 |
| *Schizophyllum cimmune* | Xyn | SEQ ID NO: 9 |
| *Streptomyces lividans* | Xyn B | SEQ ID NO: 10 |
| *Streptomyces lividans* | Xyn C | SEQ ID NO: 11 |
| *Streptomyces sp.* No. 36a | Xyn | SEQ ID NO: 12 |
| *Streptomyces thermoviolaceus* | Xyn II | — |
| *Thermomonospora fusca* | Xyn A | SEQ ID NO: 13 |
| *Thermomyces lanuginosus* | Xyn | SEQ ID NO: 20 |
| *Trichoderma harzianum* | Xyn | SEQ ID NO: 14 |
| *Trichoderma reesei* | Xyn I | SEQ ID NO: 15 |
| *Trichoderma reesei* | Xyn II | SEQ ID NO: 16 |
| *Trichoderma viride* | Xyn | SEQ ID NO: 17 |

Family 11 xylanases share extensive amino acid sequence similarity (FIG. 1). Structural studies of several Family 11 xylanases indicate that Family 11 xylanases from bacterial and fungal origins share the same general molecular structure (U.S. Pat. No. 5,405,769; Arase et al 1993). In addition, most Family 11 xylanases identified so far exhibit three types of secondary structure, including beta-sheets, turns and a single alpha helix. The helix of *Trichoderma reesei* xylanase II enzyme encompasses the region from amino acid 151 to amino acid 162 (Torronen et. al. 1995).

A xylanase is classified as a Family 11 xylanase if it comprises amino acids common to other Family 11 xylanases, including two glutamic acid (E) residues which may serve as catalytic residues. The glutamic acid residues are found at positions 86 and 177 (see FIG. 1; based on Tr2 (*Trichoderma reesei* xylanase II enzyme) amino acid numbering).

Most of the Family 11 xylanases identified thus far are mesophilic and have low-molecular masses (20 kDa). However, this family also includes at least two thermostable xylanases of higher molecular mass, *Thermomonospora fusca* xylanase A (TfX-A) of 296 amino acids and a molecular mass of approximately 32 kDa (Irwin et. al., 1994); Wilson et al. 1994, WO 95/12668) and *Clostridium stercorarium* xylanase A of 511 amino acids and a molecular mass of approximately 56 Kda. The *Clostridium stercorarium* xylanase A enzyme exhibits maximum activity at a temperature of 70° (Sakka et al., 1993).

The large thermostable Family 11 xylanases differ from the small mesophilic enzymes by the possession of a hydrophobic cellulose-binding domain (CBD) in the extended C-terminus of the enzyme. The TfX-A enzyme is composed of a catalytic core sequence of 189 residues common to all Family 11 xylanases, and a cellulose binding domain of 107 residues. The larger *C. stercorarium* xylanase A has 2 copies of the cellulose binding domain.

Site-directed mutagenesis has been used in the present invention to produce mutations in xylanases which render the enzyme more thermophilic and alkalophilic compared to the native enzyme. Preferably, the mutant xylanase is one derived from a Family 11 xylanase. More preferably, the mutant xylanase of the present invention comprises a mutant *Trichoderma reesei* xylanase II enzyme.

Therefore, it is considered within the scope of the present invention that xylanases, including Family 11 xylanases for example but not limited to *Trichoderma reesei* xylanase II, *Trichoderma reesei* xylanase I, *Trichoderma viride* xylanase, *Streptomyces lividans* xylanase B and *Streptomyces lividans* xylanase C, may be modified following the general approach and methodology as outlined herein. It is also considered within the scope of the present invention that non-Family 11 xylanases may also be modified following the general principles as described herein in order to obtain a xylanase enzyme that exhibits thermophilicity and alkalophilicity.

By the term "thermophilicity" it is meant that an enzyme is active, or more active, at a higher temperature when compared with the activity of another enzyme when all other conditions remain constant. For example, xylanase 1 exhibits increased thermophilicity compared to xylanase 2 if xylanase 1 is capable of, or is more active in, hydrolysing xylan at a higher temperature than xylanase 2, under identical conditions using the same substrate. As most xylanases are effective at a higher temperature when hydrolysing pure xylan rather than pulp, comparative analysis should be made using the same substrate. Quantitative measures of thermophilicity referred to herein use pure xylan substrates unless otherwise indicated.

By "thermostability" it is meant the ability of an enzyme to be stored or incubated at high temperature conditions, typically in the absence of substrate, and then exhibit activity when returned to standard assay conditions. For example, xylanase 1 is said to display increased thermostability compared to xylanase 2 if xylanase 1 retains a greater amount of activity than xylanase 2 after being maintained at a certain temperature (typically a higher temperature), for example but not limited to, 70° C. for 24 hours, followed by assay at a lower temperature. In contrast to thermophilicity, thermostability relates to the remaining enzyme activity following an incubation in the absence of substrate.

The use of these two terms (thermophilicity and thermostability) has been confused within the prior art as they have been used interchangeably. However, the use of the terms as defined herein is consistent with the usage of the terms in the art (Mathrani and Ahring, 1992).

By "alkalophilicity" it is meant that an enzyme is active, or more active, at a higher pH when compared with the activity of another enzyme when all other conditions remain constant. For example, xylanase 1 exhibits increased alkalophilicity compared to xylanase 2 if xylanase 1 is capable of hydrolysing xylan at a higher pH than xylanase 2. Typically alkalophilicity relates to enzyme activity in the presence of xylan substrate.

By "broader range of effective pH", it is meant than an enzyme is active, or more active, at a higher ph, a lower pH, or both a higher and lower pH, when compared to the activity of another enzyme when all other conditions remain constant. For example, which is not to be considered limiting, xylanase 1 exhibits broader range of effective pH compared to xylanase 2, if xylanase 1 is capable of hydrolysing xylan over a pH of 5.5-8.0 at close to optimal (80%) activity, while xylanase 2 can only maintain 80% optimal activity at a narrower range of pH 5.5-7.5

By "TrX numbering" it is meant the numbering associated with the position of amino acids based on the amino acid sequence of TrX (Xyn II—Table 1; Tr2—FIG. 1; SEQ ID NO:16). As disclosed below and as is evident upon review of FIG. 1, Family 11 xylanases exhibit a substantial degree of sequence similarity. Therefore, by aligning the amino acids to optimize the sequence similarity between xylanase enzymes and by using the amino acid numbering of TrX as the basis for numbering, the positions of amino acids within other xylanase enzymes can be determined relative to TrX.

By "expression efficiency", it is meant that the suitability or ease of active enzyme or enzymatic activity to be produced by the production host, and is typically calculated as quantity of active enzyme or enzymatic activity generated per unit volume of the fermentation culture when all fermentation conditions remain constant. For example, which is not to be considered limiting, xylanase 1 has improved expression efficiency compared to xylanase 2 if xylanase is produced 3-fold as much as xylanase 2 in a unit volume of culture by the same host. A non-limiting example of such a host is *E. coli*.

By modified xylanase, it is meant the alteration of a xylanase molecule using techniques that are known to one of skill in the art. These techniques include, but are not limited to, site directed mutagenesis, cassette mutagenesis, random mutagenesis, synthetic oligonucleotide construction, cloning and other genetic engineering techniques.

As described in more detail herein, several mutant xylanases have been prepared that exhibit increased thermophilicity, alkalophilicity and thermostability when compared to native xylanase. A list of several of mutants, which is not to be considered limiting in any manner, is presented in Table 2.

Furthermore, the present is directed to a modified Family 11 xylanase, for example but not limited to a xylanase obtained from a *Trichoderma* sp., that comprises at least one substituted amino acid residue, and characterized as having a maximum effective temperature (MET) between about 69° C. to about 84° C. Preferably, the modified xylanase is characterized as having a MET between about 70° to about 80° C. This invention also pertains to a modified xylanase, for example but nto limited to a xylanase obtained from *Trichoderma*, comprising at least one substituted amino acid, and characterized as having a maximum effective pH (MEP) between about 5.8 to about 8.4. Preferably the MEP is between about 6.0 to about 8.0. This invention also pertains to a modified xylanase, for example but not limited to a xylanase obtained from *Trichoderma*, comprising at least one substituted amino acid, and characterized as having a maximum effective temperature (MET) between about 69° C. to about 84° C., and a maximum effective pH (MEP) is between about 5.8 to about 8.4. Preferably the MET is between about 70° to about 84° C., and the MEP is between about 6.0 to about 8.0.

Furthermore, the present invention also relates to a native family 11 xylanase characterized as having a maximum effective temperature (MET) between about 69° C. to about 84° C., and a maximum effective pH (MEP) between about 5.8 to about 8.4. Preferably the MET is between about 70° to about 80° C., and the MEP is between about 6.0 to about 8.0.

Determination of the MET and MEP of a xylanase may be carried out as follows:
  i) measure the temperature profile of a xylanase as outlined in Example 3. The temperatures for which at least 80% of the optimal (maximum) activity are determined, and the highest temperature is the MET;
  ii) measure the pH profile of a xylanase as outlined in Example 4. The pH for which at least 80% of the optimal (maximum) activity is determined, and the highest pH is the MEP.

Figure 11:
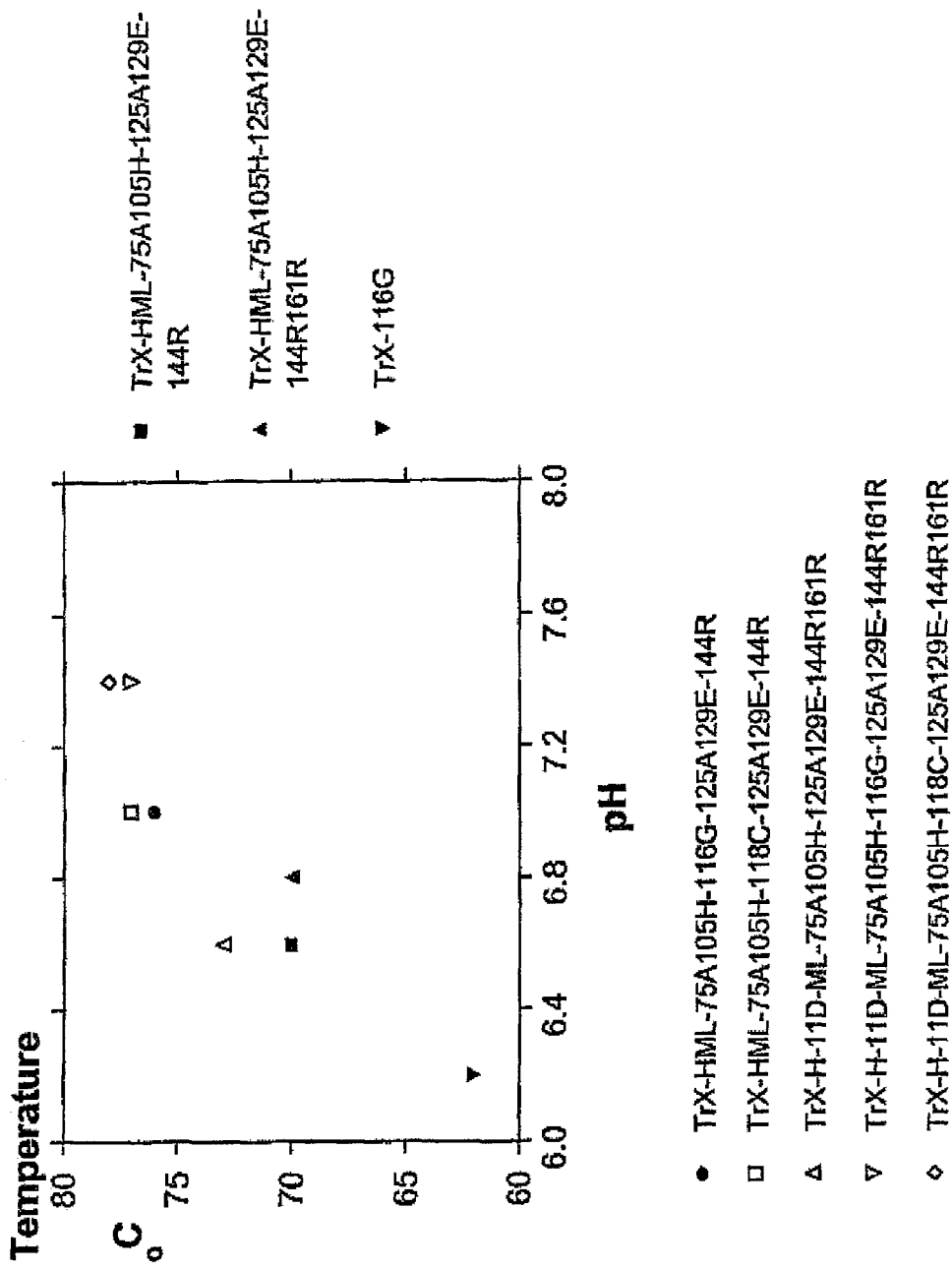
FIG. 11 shows the maximum effective temperature (MET) and maximum effective pH (MEP) values of several of the modified enzymes of the present invention. The MET and MEP are the highest temperature and pH, respectively, at which a xylanase exhibits at least 80% of its optimal activity (using soluble birchwood xylan as a substrate; see method for complete details of assays). These data points were obtained from the data presented in FIGS. 3 to 10.

These values may then be plotted as shown in FIG. 11.

TABLE 2

Modified xylanases

| Xylanase | Description |
| --- | --- |
| TrX-HML | TrX with N10H, Y27M, and N29L (see U.S. Pat. No. 5,759,840) |
| TrX-HML-105R | TrX N10H, Y27M, N29L and L105R |
| TrX-HML-75A-105R | TrX N10H, Y27M, N29L, S75A and L105R |
| TrX-HML-75G-105R | TrX N10H, Y27M, N29L, S75G and L105R |
| TrX-HML-GRAE | TrX N10H, Y27M, N29L, S75G, L105R, Q125A and I129E |
| TrX-HML-AHAE | TrX N10H, Y27M, N29L, S75A, L105H, Q125A and I129E |
| TrX-HML-AHAE-R | TrX N10H, Y27M, N29L, S75A, L105H, Q125A, I129E and 144R |
| TrX-HML-AHAE-RR | TrX N10H, Y27M, N29L, S75A, L105H, Q125A, I129E, 144R, and Q161R |
| TrX-116G | TrX D116G |
| TrX-118C | TrX Y118C |
| TrX-HML-AHGAE-R | TrX N10H, Y27M, N29L, S75A, L105H, D116G, Q125A, I129E and H144R |
| TrX-HML-AHCAE-R | TrX N10H, Y27M, N29L, S75A, L105H, Y118C, Q125A, I129E and H144R |
| TrX-H-11D-ML-AHAE-RR | TrX N10H, N11D, Y27M, N29L, S75A, L105H, Q125A and I129E, H144R and Q161R |
| TrX-H-11D-ML-AHGAE-RR | TrX N10H, N11D, Y27M, N29L, S75A, L105H, D116G, Q125, I129E, H144R and Q161R |
| TrX-H-11D-ML-AHCAE-RR | TrX N10H, N11D, Y27M, N29L, S75A, L105H, Y118C, Q125A, I129E, H144R and Q161R |
| TrX-H-11D-ML-AHCAE-RR | TrX N10H, N11D, Y27M, N29L, S75A, L105H, D116G, Y118C, Q125A, I129E, H144R and Q161R |

Substitution at position 11, 116, 118, 144 or 161 does not significantly change the specific activity of the xylanase enzyme compared to that of native xylanase (see Table 4, Example 2-3).

Improving the Expression Efficiency of Xylanase

The mutant xylanases TrX-H-11D-ML-75A105H-125A129E-144R161R, (TrX H 11D-ML-AHAE-RR); TrX-H-11D-ML-75A105H-116G-125A129E-144R161R (TrX H11D-ML-AHGAE-RR); and TrX-H-11D-ML-75A105H-118C-125A129E-144R161R (TrX H11D-ML-AHCAE-RR), all bearing the mutation of N11D, have consistently been expressed and produce from about 2.5 top about 4.3 fold as much protein than their precursors without this mutation (see Table 5, Example 2-4). These results suggested that this mutation improves the yield of the production of xylanases, an important factor in any production in industrial scale. This improvement in expression efficiency of xylanase is achieved without any decrease of thermophilicity and alkalophilicity of the xylanase.

Increasing the Thermophilicity of Xylanase

The mutation of position 144 to Arg has improved the enzymatic activity of mutant xylanase TrX-HML-75A105H-125A129E-144R (TrX-HML-AHAE-R) in the hydrolysis of xylan at higher temperatures (FIG. 3), when compared to the precursor xylanase TrX-HML-75A105H-125A129E that lacks this mutation. Therefore, the present invention provides a native or a modified xylanase comprising a basic amino acid, for example but not limited to Arg, at position 144. Preferably the native or modified xylanase with the basic amino acid at position 144 exhibits a MET between about 69° C. to about 84° C.

Two mutations at positions 116 and 118 to Gly and Cys, respectively, also demonstrate improved activity of xylanase at high temperatures. Compared to native TrX, the single point mutants TrX-116G and TrX-118C exhibit greater activity at higher temperatures (FIG. 4), with a temperature optimum at 55° C., v. 50° C. exhibited by native TrX.

Figure 6:
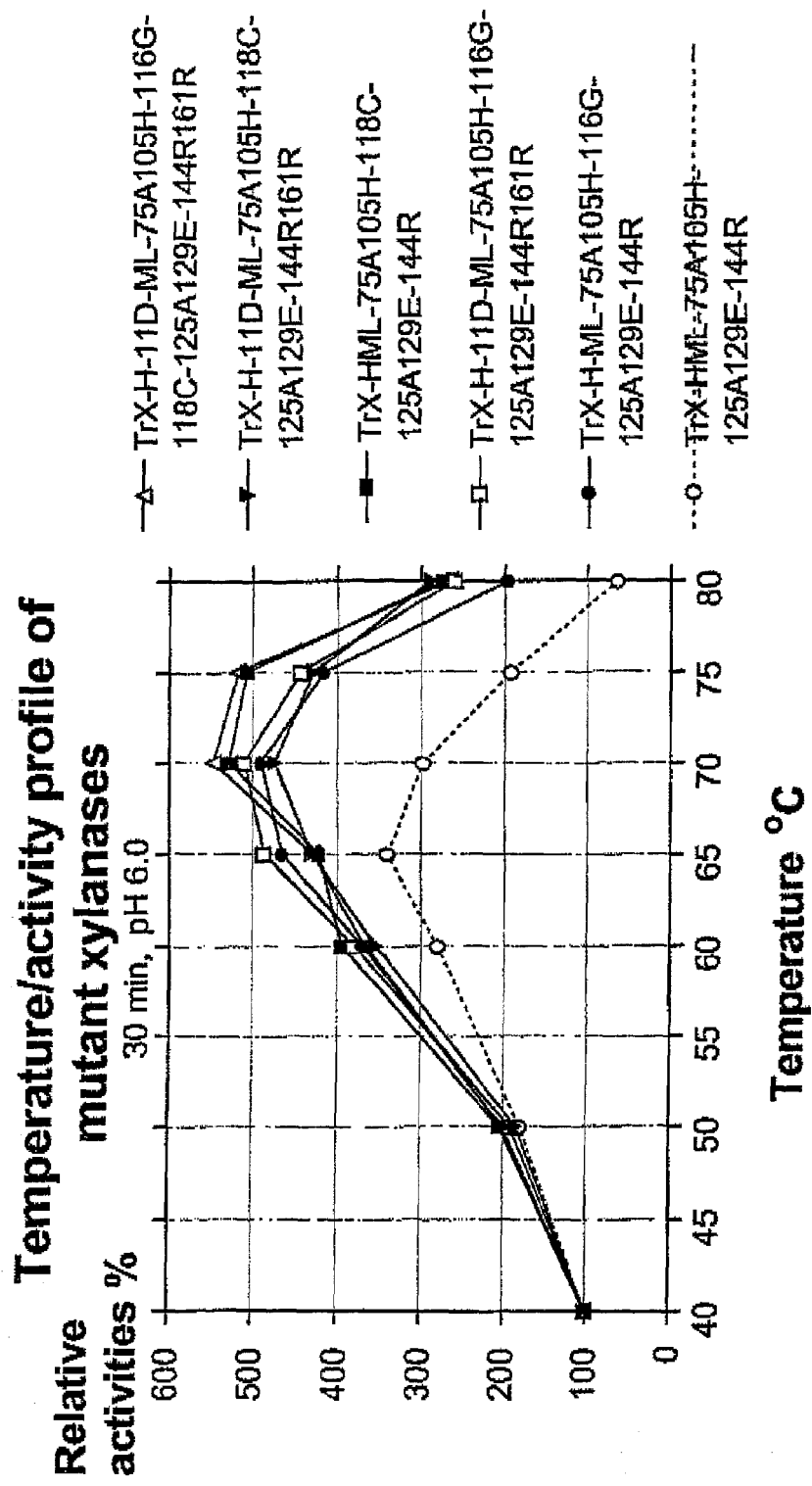
FIG. 6 shows the effect of temperature on the enzymatic activity of modified xylanases TrX-H-11D-ML-75A105H-116G118C-125A129E-144R161R, TrX-HML-75A105H-116G-125A129E-144R, TrX-H-11D-ML-75A105H-116G-125A129E-114R161R, TrX-HML-75A105H-118C-125A129E-144R and TrX-H-11D-ML-75A105H-118C-125A129E-144R161R, as compared to TrX-HML-75A105H-125A129E-144R, at pH 6.0 during 30-min incubations. The data are normalized to the activity observed at 40° C.
Figure 7:
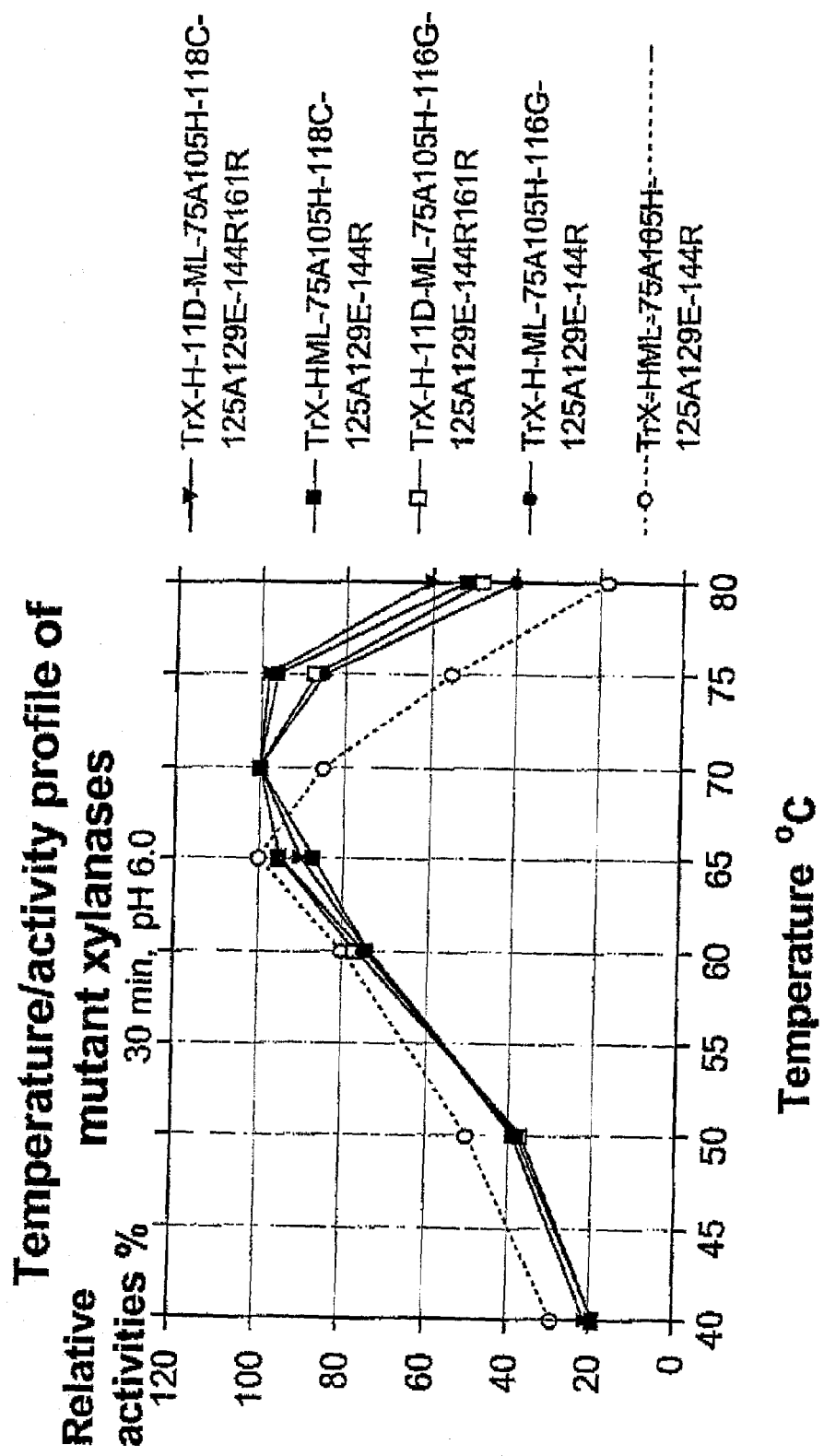
FIG. 7 shows the effect of temperature on the enzymatic activity of modified xylanases TrX-HML-75A105H-116G-125A129E-144R and TrX-H-11D-ML-75A105H-116G-125A129E-144R161R, TrX-HML-75A105H-118C-125A129E-144R and TrX-H-11D-ML-75A105H-118C-125A129E-144R161R, as compared to TrX-HML-75A105H-125A129E-144R, at pH 6.0 during 30-min incubations. The data are normalized to maximum activity for each enzyme.

The same enhancement in thermophilicity by these two mutations (116 and 118 to Gly and Cys, respectively) is also observed in: TrX-HML-75A105H-116G-125A129E-144R (TrX-HML-AHGAE-R); and TrX-HML-75A105H-118C-125A129E-144R (TrX-HML-AHCAE-R), when compared to the precursor xylanase, TrX-HML-75A105H-125A129E-144R (TrX-HML-AHAE-R) at pH 5.5 (see FIG. 5, 116G mutant) and pH 6.0 (FIGS. 6 and 7).

The improvement in thermophilicity by the mutations at position 116 to a small non-polar residue is unexpected as a majority of the natural xylanases including the thermophilic xylanases (for example, Tf, Fl, Cs, FIG. 1) possess negatively charged amino acids, aspartic acid (D, 66%, FIG. 1) and glutamic acid (E, 10%, FIG. 1), or a polar, uncharged amino acid glutamine (Q, 15%, FIG. 1) at this position. No known xylanases possess a Gly at position 116. Therefore, the present invention also pertains to a native or a modified xylanase comprising a non-polar amino acid, for example but not limited to Gly, at position 116. Preferably the native or modified xylanase with the non-polar amino acid at position 116 exhibits a MET between about 69° C. to about 84° C.

The improvement of thermophilicity based on the mutation at position 118 to cysteine is also unexpected, as most xylanases including the thermophilic xylanases (Tf, Tl, Cs, FIG. 1) possess a tyrosine (Y, 60%, FIG. 1) and trytophan (W, 10%, FIG. 1). The only xylanases possessing Cysteine at position 118 are among the mesophilic *Aspergillus niger, Aspergillus kawakii* and *Aspergillus tubigensis* (FIG. 1), with temperature optimum of these xylanases around 45-55° C. (Sunna and Antranikian, 1997). Therefore, the present invention also pertains to a modified xylanase comprising a non-aromatic hydrophobic amino acid, for example but not limited to Cys at position 118, and to a native xylanase comprising a non-aromatic hydrophobic amino acid at position 118, providing that the native xylanase exhibits a MET between about 69° C. to about 84° C.

Figure 8:
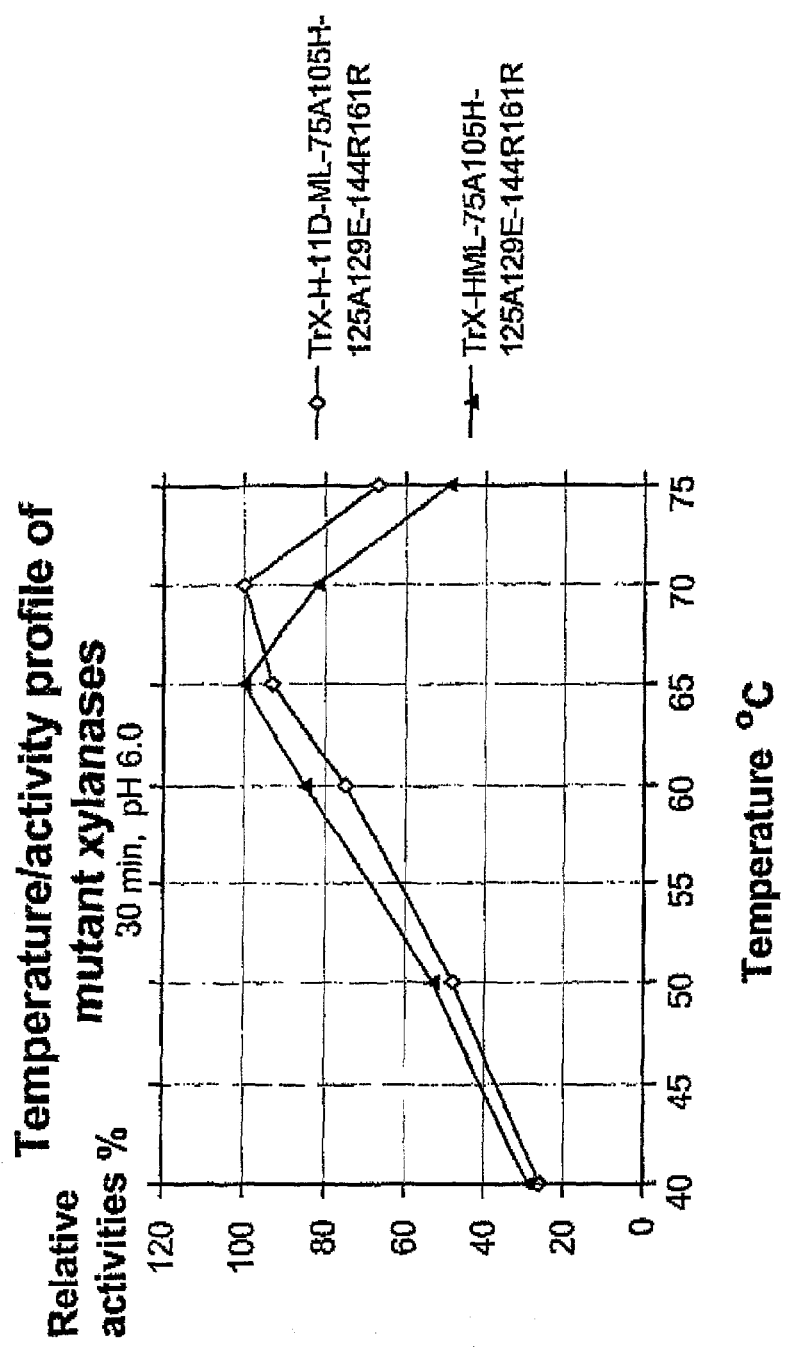
FIG. 8 shows the effect of temperature on the enzymatic activity of modified xylanases TrX-H-11D-ML-75A105H-125A129E-144R161R, as compared to TrX-HML-75A105H-125A129E-144R, at pH 6.0 during 30-min incubations. The data are normalized to the activity observed at 40° C.

Another mutation at position 11 to Asp also benefits thermophilicity of xylanase. Mutant TrX-H-11D-ML-75A105H-125A129E-144R161R (Trx-H11D-ML-AHAE-RR) exhibits greater activity at higher temperatures, as compared to the precursor TrX-HML-75A105H-125A129E-144 (TrX-HML-AHAE; FIG. 8). This result is also unexpected since (Turenen et. al. (2001) reported that the same N11D mutation lowered the temperature optima and range in a TrX mutant containing an intramolecular disulfide bond. Furthermore, U.S. Pat. No. 5,759,840 discloses that the 11D mutation has not effect on thermophilicity of TrX-H-11D-ML (mutant termed NI-TX12). Therefore, the present invention also pertains to a native or a modified xylanase comprising an acidic amino acid, for example but not limited to Asp, at position 118, providing that the native or modified xylanase exhibits a MET between about 69° C. to about 84° C.

Furthermore, mutations identified above can be combined to create mutant xylanases with greater thermophilicity, even at higher pH range. The combination mutants xylanases based on triple mutations N11D/D116G/144R or N11D/Y118C/144R, namely: TrX-H-11D-ML-75A105H-116G-125A129E-144R161R (TrX-H11D-ML-AHGAE-RR); and TrX-H-11D-ML-75A105H-118C-125A129E-144R161R (Trx-H11D-ML-AHCAE RR), exhibited a maximum enzymatic activity at higher temperature of 70-75° C. and further showed significant enzymatic activity at 80° C. at pH 5.5 (FIG. 5, only 116G mutant) and pH 6.0 (FIGS. 6 and 7). These results suggest the effects of the mutations D116G or Y118C with N11D and H144R on the thermophilicity of the mutant xylanase are complementary. Therefore, the present invention relates to a native or a modified xylanase comprising an acidic amino acid at position 11, a non-polar amino acid at position 116, and a base amino acid at position 144, for example but not limited to N11D/D116G/144R, or an acidic amino acid at position 11, a non-aromatic hydrophobic amino acid at position 118, and a basic amino acid at position at position 114, for example but not limited to N11D/Y118C/144R. Preferably the native or modified xylanase comprising an acidic amino acid at position 11, a non-polar amino acid at position 116, and a basic amino acid at position 144, or the xylanase comprising an acidic amino acid at position 11, a non-aromatic hydrophobic amino acid at position 118, and a basic amino acid at position at position 114, exhibits a MET between about 69° C. to about 84° C.

In addition to achieve optimal activity at higher temperatures, the mutant xylanases based on the present invention, for example: TrX-H-11D-ML-75A105H-116G-125A129E-144R161R (TrX-H11D-ML-AHGAE-RR); and TrX-H-11D-ML-75A105H-118C-125A129E-144R161R (TrX-H11D-ML-AHCAE-RR), (FIGS. 5 and 6), also demonstrate higher enzymatic activity (detected as greater xylose release) at their temperature optima. Both TrX-H11D-ML-AHGAE-RR and TrX-H11D-ML-AHCAE-RR exhibit about 600% activity at their temperature optima, than the activity observed at 40° C. This compared with the precursor, modified xylanase TrX-HML-75A105H-125A129E, which exhibits about 400% activity at its temperature optima, versus its activity at 40° C., and natural TrX (150% of its activity at its optimal temperature, v. value at 40° C.).

This invention therefore includes a modified xylanase comprising a His at positions 10 and 105, a Met at position 27, a Leu at position 29, an Ala at positions 75 and 125, a Glu at position 129, and at least one of:

an acidic amino acid at positions 11;

a small non-polar amino acid at position 116;

a medium-size non-aromatic hydrophobic amino acid at position 118; and a basic amino acid at position 144

Preferably, the amino acid at position 11 is Asp (D), the amino acid at position 116 is Gly (G), the amino acid at position 118 is Cys (C), and the amino acid at position 144 is selected from the group consisting of Lys (L), and Arg (R).

Increasing the Alkalophilicity of Xylanase

Figure 9:
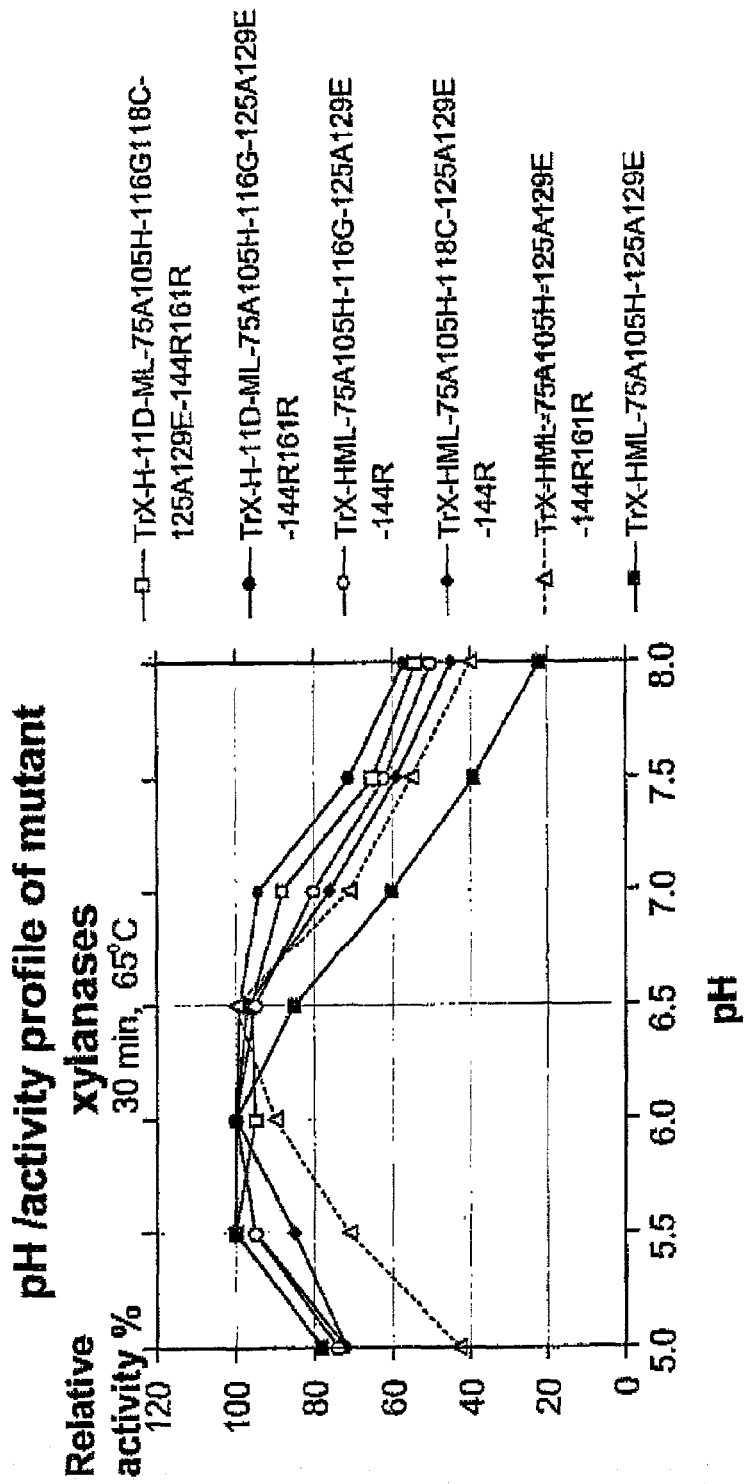
FIG. 9 shows the pH/activity profile of modified xylanase enzymes TrX-H-11D-ML-75A105H-116G118C-125A129E-144R161R, TrX-H-11D-ML-75A105H-116G-125A129E-114R161R, TrX-HML-75A105H-116G-125A129E-144R and TrX-HML-75A105H-118C-125A129E-144R, as compared to TrX-HML-75A105H-125A129E-144R161R and TrX-HML-75A105H-125A129E, over pH 5.0-8.0 at 65° C. during 30-min incubation. The data are normalized to the pH exhibiting optimal activity for each enzyme.

The effect of pH conditions on the enzymatic activity by the mutation Q161R in the mutant xylanase TrX-HML-75A105H-125A129E-144R161R (TrX-HML-AHAE-RR), is shown in FIG. 9. Compared to its precursors TrX-HML-75A105H-125A129E and TrX-HML-75A105H-125A129E-144R (not shown). These latter enzymes have identical pH/activity profiles, however, the mutant xylanase TrX-HML-75A105H-125A129E-144R161R (TrX-HML-AHAE-RR) exhibits a greater activity at higher pH ranges of about 6.5 to about 8.0. TrX-HML-AHAE-RR also exhibits lower activity at lower pHs of about 5.0 to about 6.0, when compared to precursors without this mutation. Therefore, the present invention relates to a native or a modified xylanase comprising a basic amino acid, for example but not limited to Arg, at position 161. Preferably the native or modified xylanase with the basic amino acid at position 161 exhibits a MEP between about 5.8 to about 8.4.

Figure 10:
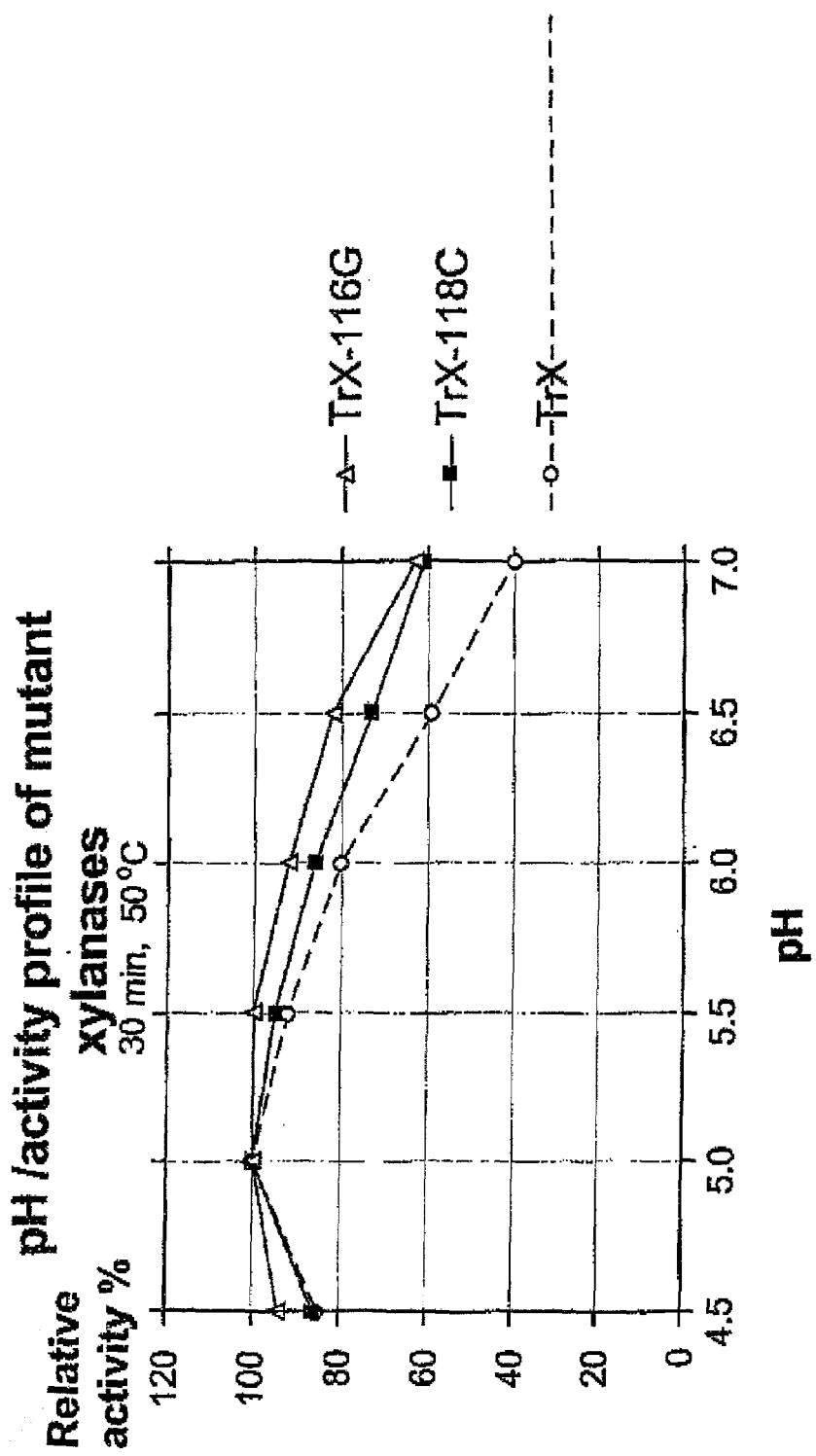
FIG. 10 shows the pH/activity profiles of modified xylanases TrX-116G and TrX-118C, as compared to native TrX, over pH 4.5-7.0 at 50° C. during 30-min incubation. The data are normalized to the pH exhibiting optimal activity for each enzyme.

The mutations at positions 116 and 118 to Gly and Cys, respectively, also improve enzymatic activity at higher pH ranges. Compared to native TrX, the single mutants TrX-116G and TrX-118C have greater activity at higher pH as shown in FIG. 10.

The improvement by the mutation at positions 116 to a small non-polar residue to improve alkalophilicity is unexpected as no natural possess a Gly at position 116. Therefore, the present invention provides a native or a modified xylanase comprising a non-polar amino acid, for example but not limited to Gly, at position 116. Preferably the native or modified xylanase with the non-polar amino acid at position 116 exhibits a MEP between about 5.8 to about 8.4.

The improvement of thermophilicity based on the mutation at position 118 to cysteine is also unexpected, as most xylanases including the alkalophilic xylanase (for example, Tf, Bp, see FIG. 1) possess a tyrosine (Y, 60%, FIG. 1) and trytophan (W, 10%, FIG. 1). The only xylanases possessing cysteine at position 118 are among the acidophilic *Aspergillus niger, Aspergillus kawakii* and *Aspergillus tubigensis* (FIG. 1), with pH optimum of these xylanases around 2-4 (Sunna and Antranikian, 1997; Kinoshita et al 1995). Therefore, the present invention embraces a native or a modified xylanase comprising a non-aromatic hydrophobic amino acid, for example but not limited to Cys, at position 118. Preferably the native or modified xylanase with the non-aromatic hydrophobic amino acid at position 118 exhibits a MEP between about 5.8 to about 8.4.

An enhancing effect in alkalophilicity of xylanase, by the mutations D116G and Y118C, is also observed in the mutants: TrX-HML-75A105H-116G-125A129E-144R (TrX-HML-AHGAE-R); and TrX-HML-75A105H-118C-125A129E-144R (TrX-HML-AHCAE-R), (FIG. 9), when compared to the precursor xylanases TrX-HML-75A105H-125A129E-144R and TrX-HML-75A105H-125A129E. While both mutants demonstrated higher activity at pH from about 6.5 to about 8.0, only the mutant TrX-HML-75A105H-116G-125A129E-144R (TrX-HML-AHGAE-R) retains substantially optimal activity at the lower pH of about 5.0 to about 6.0. This maintenance of high activity at pH of about 5.0 to about 8.0 represents a broadening of the optimal pH range by this mutation at position 116.

Mutations identified above have been combined to create mutant xylanases with greater alkalophilicity and thermophilicity. The combination mutants xylanases based on quadriple mutations N11D/D116G/H144R/Q161R or N11D/Y118C/144R/Q161R, namely: TrX-H-11D-ML-75A105H-116G-125A129E-144R161R (TrX-H11D-ML-AHGAE-RR; FIG. 9); and TrX-H-11D-ML-75A105H-118C-125A129E-144R161R (TrX-H11D-ML-AHCAE-RR; not shown), exhibit close to maximum enzymatic activity at pH from about 5.0 to about 7.0, as compared to their precursors. Furthermore the presence of the mutation D116G helps the retaining of substantially maximal activity at lower pH range of about 5.0 to about 6.0, thus avoiding the significant loss of activity at low pH observed in precursor TrX-HML-75A105H-125A129E-144R161R (FIG. 9). This result further confirmed the broadening of the optimal pH range by this mutation at position 116. Therefore, the present invention relates to a native or a modified xylanase comprising an acidic amino acid at position 11, a non-polar amino acid at position 116, and a basic amino acid at position 114, for example but not limited to N11D/D116G/144R, or an acidic amino acid at position 11, a non-aromatic hydrophobic amino acid at position 118, and an basic amino acid at position at position 114, for example but not limited to N11D/Y118C/144R. Preferably the native or modified xylanase comprising an acidic amino acid at position 11, a non-polar amino acid at position 116, and a basic amino acid at position 114, or the xylanase comprising an acidic amino acid at position 11, a non-aromatic hydrophobic amino acid at position 118, and a basic amino acid at position 114 a MEP between about 5.8 to about 8.4.

This invention also provides a modified xylanase comprising a His at positions 10 and 105, a Met at position 27, a Leu at position 29, an Ala at positions 75 and 125, a Glu at position 129, and at least one of:
- an acidic amino acid at position 11;
- a small non-polar amino acid at position 116;
- a medium-size non-aromatic hydrophobic amino acid at position 118;
- a basic amino acid at position 161.

Preferably, the amino acid at position 11 is Asp, the amino acid at position 116 is Gly, the amino acid at position 118 is Cys, the amino acid at position 161 is selected from the group consisting of Lys, and Arg.

In summary, improved alkalophilic mutant TrX xylanases may be constructed through;
i) mutation of Asp 116 to a small non-polar residue, for example, but not limited to Gly;
ii) mutation of Tyr 118 to a medium-size, non-aromatic hydrophobic residue such as but not limited to Cys;
iii) mutation of Glen 161 to a basic amino acid Arg or Lys;
iv) combination of mutations described in i) with those described in ii) to iii) for the improvement of thermophilicity and alkalophilicity; or
v) combination of mutations described in i) to iv), above, with the HML series of mutations as described above (see U.S. Pat. No. 5,759,840 which is incorporated herein by reference for HML mutations).

The above description is not intended to limit the claimed invention in any manner, furthermore, the discussed combination of features might not be absolutely necessary for the inventive solution.

EXAMPLES

The present invention will be further illustrated in the following examples. However, it is to be understood that these examples are for illustrative purposes only, and should not be used to limit the scope of the present invention in any manner.

Example 1

Construction of *Trichoderma reesei* Mutant Xylanases

Basic recombinant DNA methods like plasmid preparation, restriction enzyme digestion, polymerase chain reaction, oligonucleotide phosphorylation, ligation, transformation and DNA hybridization were performed according to well-established protocols familiar to those skilled in the art (e.g. Sung et al., 1986) or as recommended by the manufacturer of the enzymes or kit. The buffers for many enzymes have been supplied as part of a kit or made according to the manufacturer's instructions. Restriction enzymes, T4 polynucleotide kinase and T4 DNA ligase were purchased from New England BioLabs Ltd, Mississauga, Ont. GeneAmp PCR reagent kit was purchased from Perkin-Elmer. A precursor plasmid pXYbe, which is a pUC type plasmid with a *Bacillus circulans* xylanase gene inserted, has previously been prepared and published (Sung et al, 1993; Campbell et al., U.S. Pat. No. 5,405,769). A commonly used *E. coli* strain, HB101 (Clonetech Lab, Palo Alto, Calif.) was used as a transformation and expression host for all gene constructs. Birchwood xylan and Remazol Brilliant Blue R-D-Xylan were purchased from Sigma (St. Louis, Mo.). Hydroxybenzoic acid hydrazide (HBAH) was purchased from Aldrich. Oligonucleotides were prepared with an APPLIED BIOSYSTEM DNA synthesizer (model 380B). All xylanase enzymatic assays were performed in a covered circulating water bath (Haake type F 4391) and maintained within a temperature range of ±0.1° c.

1-1: Construction of Precursor Plasmid pTrX Harbouring Synthetic TrX (SEQ ID NO:39)

The precursor plasmid pTrX for mutations disclosed below has been previously published (Sung et al, 1995). This plasmid is derived from a pUC119 plasmid with a synthetic nucleotide sequence encoding a *Trichoderma reesei* xylanase (TrX; FIG. 2). Expression of this xylanase and other mutant xylanases subsequently described are under the control of the lac Z promoter of the pUC plasmid. The total assembly of the *Trichoderma* xylanase gene required two stages, initially for the (92-190; Tr2 numbering) region, then followed by the (1-92; Tr2 numbering) region. The protocol for the construction of this gene is routine and identical to the standard published procedure for many other genes. The protocol requires enzymatic phosphorylation of overlapping synthetic oligonucleotides which encodes a xylanase. This is followed by their ligation into an appropriately cut plasmid.

For the construction of TrX (92-190), ten overlapping oligonucleotides (see FIG. 2):
XyTv-101, SEQ ID NO:29;
XyTv-102, SEQ ID NO:30;
TrX-103, SEQ ID NO:31;
XyTv-104, SEQ ID NO:32;
XyTv-105, SEQ ID NO:33;
XyTv-106, SEQ ID NO:38;
XyTv-107, SEQ ID NO:37;
TrX-108, SEQ ID NO:36;
XyTv-109, SEQ ID NO:35; and
XyTv-110, SEQ ID NO:34 were designed with codon usage frequency imitating that of *E. coli*. The SalI and BglII cohesive ends of two terminal oligonucleotides enabled the enzymatic ligation of the ten fragments into the linearized plasmid pXYbc. The ten oligonucleotides (50 pmol, 1 µL for each) encoding the TrX(92-190) region of *Trichoderma* xylanase were phosphorylated in a mixture containing 10X standard kinase buffer (0.4 µL), 1 mM ATP (4 µL), T4 DNA kinase (5 units), and water (3 µL). Phosphorylation reactions were carried out for 1 h at 37° C. The solutions were then combined and heated to 70° C. for 10 min. After being cooled slowly to room temperature, the combined solutions were added to a mixture of 4 mM ATP (3.5 µL), EcoRI-HindIII linearized plasmid pUC119 (0.1 pmol), and T4 DNA ligase (3.5 µL) and incubated at 12° C. for 20 h. Aliquots of the ligation mixture were used to transform *E. coli* HB101 on YT plates (8 g yeast extract, 5 g bactotryptone, 5 g NaCl, 15 g of agar in 1 L of water) containing ampicillin (100 mg/L).

For the preparation of a hybridization probe, one of the oligonucleotides, for example XyTv-110 (10 pmol, 1 µL) was phosphorylated with $^{32}$P-ATP (10 pmol, 3 µL) using T4 DNA kinase (1 µL), 10X kinase buffer (1 µL), and water (4 µL) at 37° C. for 1 h.

Transformants were selected randomly for hybridization analysis. Colonies were grown an YT plates with ampicillin overnight, and transferred onto nylon filters. They were then denatured with 0.5N NaOH—1.5M NaCl (10 min) and neutralized with 0.5N Tris-HCl (pH 7.0)—1.5M NaCl (10 min). After ultraviolet irradiation at 254 nm for 8 min, the filters were washed with 6X SSC—0.05% Triton X-100 for 30 min. Cell debris was scraped off completely. After another 30 min. in fresh solution, duplicate filters were transferred individually into separate mixtures of 6X SSC—1% dextran sulphate—0.05% TritonX-100—1X Denhardt's hybridization fluid. The $^{32}$P-labelled probe was added to the filter. After 16 h at 45° C., the filter was washed twice with 6X SSC—0.5% TritonX-100 at room temperature for 5 min. and then at 65° C. for 30 min. Positively hybridized clones with the intermediate plasmid pBcX-TrX were identified by auto-radiographic analysis.

labelled oligonucleotide, and (v) confirmation of the mutation through dideoxy nucleotide sequencing.

1-2: Construction of the Precursor Plasmid pTrX-HML

The construction of this precursor plasmid pTrX-HML has been described in detail in U.S. Pat. No. 5,759,840 (see Example 1N, herein incorporated by reference; plasmid termed pNI-TX13). TrX-HML comprises the native TrX xylanase, along with three mutations at N10H (Asn at position 10 is replaced with His), Y27M and N29L. The first thirty amino acids of the sequence comprising N10H, Y27M and N29L are shown below (SEQ ID NO:56, 57; DNA and amino acid, respectively).

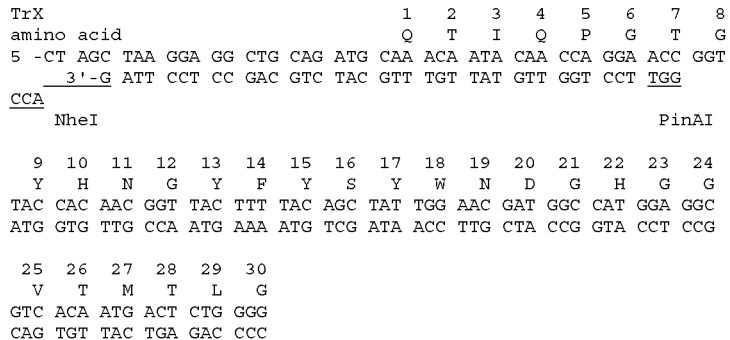

The above protocol, involving enzymatic phosphorylation of synthetic overlapping oligonucleotides and ligation into a linearized plasmid, was employed in the assembly of the TrX(1-92) region and in the cassette mutagenesis for the subsequent generation of other mutant xylanases described in this invention.

For the assembly of the TrX(1-92; Tr2 numbering) region to complete the full-length *Trichoderma reesei* xylanase II gene (TrX), the intermediate plasmid pBcX-TrX was linearized by NheI and KpnI endonucleases to release the DNA insert for BcX(1-83). With NheI and KpnI cohesive ends, eight overlapping oligonucleotides:

TrX-1, SEQ ID NO:21;
XyTv-2, SEQ ID NO:22;
TrX-3, SEQ ID NO:23;
XyTv-4, SEQ ID NO:24;
XyTv-5, SEQ ID NO:28;
TrX-6, SEQ ID NO:27;
XyTv-7, SEQ ID NO:26; and
TrX-8 SEQ ID NO:25, encoding the TrX(1-91) sequence were ligated into the linearized plasmid pBcX-TrX (FIG. 2), via the protocol described above. The new plasmid pTrX therefore harbored a synthetic TrX gene (SEQ ID NO:39).

All mutant xylanase genes described below have been constructed via the method of cassette mutagenesis. The protocol for cassette mutagenesis was identical to that described for gene assembly described above. Generally, cassette mutagenesis involved (i) enzymatic phosphorylation of overlapping synthetic oligonucleotides, (ii) ligation of synthetic oligonucleotides with a linearized plasmid, (iii) transformation of the plasmid into *E. coli* HB101 competent cells, (iv) identification of mutant transformants via hybridization with the 1-3: Construction of the Deletion Plasmid pTrX-HML-(1-113)

Plasmid pTrX-HML-(1-113) comprises the amino acid sequence 1-113 of TrX (SEQ ID NO:39) and cannot express an active xylanase. Such transformants are confirmed by the absence of a clearing zone or halo around the transformant colonies on blue xylan plates.

The new plasmid was constructed via (i) the removal of the TrX(114-190) coding sequence of pTrX-HML through cutting with restriction enzymes BamHI and BglII, (ii) ligation of the identical cohesive ends of the linearized plasmid, (iii) transformation into the *E. coli* HB101 competent cells followed by platting on YT plate (containing 5 g yeast extract, 3 g bacto-tryptone, 5 g NaCl, 15 g of agar in 1 L of water, 1 g Remazol Brilliant Blue R-D-xylan) and ampicillin (100 mg/L), (iv) identification of the mutant transformants through the loss of xylanase activity (absence of a clearing zone or halo around the colonies on the blue xylan plate overnight at 40° C.), and (v) confirmation of the mutation through dideoxy nucleotide sequencing. The protocol for each of these steps was similar to that for gene assembly described above.

1-4: Construction of the Plasmid pTrX-HML-105R

Mutant xylanase pTrX-HML-105R is similar to TrX-HML except that Leu at position 105 is replaced by Arg (L105R).

PCR was used to generate a DNA fragment encoding (100-190) region with the L105R mutation. The PCR primers with mutation (in bold type) in the construction of pTrX-HML-105R is shown below:

```
TX-105R-1 (SEQ ID NO:44 and 58; DNA and amino acid, respectively)
        100 101 102 103 104 105 106 107 108 109 110 111 112 113
         T   G   A   T   K   R   G   E   V   T   S   D   C   S
5'-ACC GGC GCC ACA AAA AGA GGC GAA GTC ACT AGT GAT GGA TCC
       KasI Reverse PCR primer TX-C1 comprised:
TX-C1 (SEQ ID NO:42 and 59; DNA and amino acid, respectively)
183 184 185 186 187 188 189 190 ter
 C   S   A   S   I   T   V   S
CCA AGG CGA TCA TAA TGT CAC TCG ATT TCT AGA ACT TCG AAC CC-5'
                                BglI      HindIII
```

The appropriate PCR template and primers, and the restriction enzymes to cut the end of the PCR products are listed below (Table 3-1).

TABLE 3-1

| PCR product | PCR upstream primer | PCR reverse primer | PCR template | Restriction enzymes for PCR primer |
|---|---|---|---|---|
| (a) | TX-105R-1 | TX-C1 | pTrX | KasI/HindIII |

The cut PCR product (a) (Table 3-1) was ligated into a KasI/HindIII-linearized plasmid pTrX-HML(1-113) to generate plasmid pTrX-HML-105R.

1-5: Construction of the Plasmids pTrX-HML-75A105R and pTrX-HML-75G105R

Xylanase mutants TrX-HML-75A-105R and TrX-HML-75G105R are similar to TrX-HML-105R, with the exception of an additional single mutation S75A or S75G respectively.

The PCR primers with mutations S75A (TX-75A-1; SEQ ID NO: 40) and S75G (TX75-G-1; SEQ ID NO: 46) are shown below.

```
TX-75A-1 (SEQ ID NO:40 and 60; DNA and amino acid, respectively)
    69  70  71  72  73  74  75  76  77  78  79  80  81
     N   G   N   S   Y   L   A   V   Y   G   W   S   R
5'-T GGG AAT TCA TAC TTA GCC GTC TAT GGC TGG TCT AG
        EcoRI TX-75G-1 (SEQ ID NO:46 and 61; DNA and amino acid, respectively)
    69  70  71  72  73  74  75  76  77  78  79  80  81
     N   G   N   S   Y   L   G   V   Y   G   W   S   R
5'-T GGG AAT TCA TAC TTA GGC GTC TAT GGC TGG TCT AG
        EcoRI
```

The appropriate PCR template and primers, and the restriction enzymes to cut the end of the PCR products are listed below (Table 3-2).

TABLE 3-2

| PCR product | PCR upstream primer | PCR reverse Primer | PCR template | Restriction enzymes for PCR product |
|---|---|---|---|---|
| (b) | TX-75A-1 | TX-C1 | pTrX-HML-105R | EcoRI/HindIII |
| (c) | TX-75G-1 | TX-C1 | pTrX-HML-105R | EcoRI/HindIII |

The EcoRI/HindIII-cut PCR products (b) and (c) (see Table 3-2) were prepared and ligated into EcoRI/HindIII-linearized pTrX-HML(1-113) plasmid to generate plasmids pTrX-HML-75A-105R and pTrX-HML-75G-105R respectively.

1-6: Construction of the Plasmids pTrX-HML-75G105R-125A129E

The mutant TrX-HML-75G-105R-125A129E was identical to TrX-HML-75G-105R, with the exception of the additional mutations Q125A and I129E.

The intact mutant xylanase gene was assembled via the ligation of two DNA sequences encoding the 1-121 and the 122-190 regions. The DNA sequecence encoding the 1-121 region was isolated through the deletion of plasmid pTrX-HML-75G-105R with restriction nucleases listed below (Table 3-3).

TABLE 3-3

| Deletion sequence | Precursor plasmid | Restriction enzymes |
|---|---|---|
| (A) | pTrX-HML-75G-105R | NheI/MluI |

The DNA sequence encoding the 122-190 region was a PCR product (d) by a primer encoding the mutations as shown below.

The appropriate PCR primers with mutations at position-105 and the restriction enzymes to cut the end of the PCR product are listed below (Table 3-6).

```
TX-125A129E-1 (SEQ ID NO:49 and 62; DNA and amino acid, respectively)
 120 121 122 123 124 125 126 127 128 129 130 131 132 133
     Q   R   V   N   A   P   S   I   E   G   T   A   T
5'-C CAA CGC GTT AAT GCG CCA TCG ATC GAG GGA ACC GCC ACC
     MluI
```

The appropriate PCR template and primers, and the restriction enzymes to cut the end of the PCR product, are listed below (Table 3-4).

TABLE 3-4

| PCR product | PCR upstream primer | PCR reverse primer | PCR template | Restriction enzymes for PCR product |
|---|---|---|---|---|
| (d) | TX-125A129E-1 | TX-C1 | pTrX | MluI/HindIII |

The cut PCR product (d) and the deletion sequence (A) were ligated to the NheI/HindIII-linearized plasmid pTrX-(1-113) to generate the plasmid pTrX-HML-75G-105R-125A129E.

1-7: Construction of the Plasmid pTrX-HML-75A105H-125A129E

The intact mutant gene was assembled via the ligation of two DNA sequences encoding the 1-101 and the 102-190 regions.

For the preparation of the DNA sequence encoding the 1-101 region, restriction nucleases for the deletion of the appropriate plasmid are listed below (Table 3-5).

TABLE 3-5

| Deletion sequence | Precursor plasmid | Restriction enzymes |
|---|---|---|
| (B) | pTrX-HML-75A-105R | NheI/KasI |

For the preparation of the DNA sequence encoding the 102-190 region, polymerase chain reaction was used with primer TX-105H-I.

TABLE 3-6

Plasmid pTrX-HML-75G-105R-125A129E as PCR template.

| PCR product | PCR upstream primer | PCR reverse primer | Restriction enzymes for PCR product |
|---|---|---|---|
| (e) | TX-105H-1 | TX-C1 | KasI/HindIII |

The cut PCR product (e) and the deletion sequence (B) were ligated to the NheI/HindIII-linearized plasmid pTrX-(1-113) to generate the plasmid pTrX-HML-75A-105H-125A129E.

1-8: Construction of the Deletion Plasmid pTrX-del(43-53)

A plasmid pTrX-del(43-53) encoding an inactive xylanase with the (43-53) region deleted, was constructed via restriction cutting of the plasmid pTrX at the BspEI site at residue 43 and the XmaI site at residue-53 and self-ligation of the identical ends. After transformation, the correct clones were identified through non-expressing of xylanase or absence of halo or clearing zone in blue xylan-containing YT plates.

1-9: Construction of the Deletion Plasmids pTrX-del(123-144) and pTrX-HML-75A105H-del(123-144)

Two plasmids containing partially deleted xylanase gene, were constructed via a PCR reaction with a new primer encoding the deletion of the (123-144) region.

PCR oligonucleotide primers:

```
TX-105H-1 (SEQ ID NO:41 and 63; DNA and amino acid, respectively)
   100 101 102 103 104 105 106 107 108 109 110 111 112 113
    T   G   A   T   K   N   G   E   V   T   S   D   G   S
5'-ACC GGC GCC ACA AAA CAC GGC GAA GTC ACT AGT GAT GGA TCC
       KasI
```

TX-del(123-144)-1r (SEQ ID NO:43 and 64; DNA and amino acid, respectively)
```
 148 147 146 145     122 121 120 119 118 117 116 115
  G   S   S   R       R   Q   T   R   Y   I   D   Y
5'-C GGA GCT CCG AC GCG TTG GGT ACG GTA GAT ATC ATA
     SacI        MluI
```

TX-N1 (SEQ ID NO:45 and 65; DNA and amino acid, respectively)
```
                  1   2   3   4   5   6   7
                  Q   T   I   Q   P   G   T
5'-CT AGC TAA GGA GG CTG CAG ATG CAA ACA ATA CAA CCA GGA A
   NheI          PstI
```

TABLE 3-7

PCR template with TX-del(123-144)-1r and TX-N1 as primer

| PCR product | PCR template | Restriction enzymes for PCR product |
|---|---|---|
| (f) | pTrX | PstI/SacI |
| (g) | PTrX-HML-75A105H-125A129E | PstI/SacI |

Ligation of the cut PCR fragments (f) and (g) to the PstI/SacI-linearized plasmid pTrX and transformation to yield the correct clones harboring the deletion plasmids pTrX-del(123-144) and pTrX-HML-75A105H-del(123-144) respectively, that were identified through non-expressing of xylanase and absence of halo or clearing zone in the blue xylan-containing YT plates.

1-10: Construction of the Plasmid pTrX-HML-75A105H-125A129E-144R

The new mutant pTrX-HML-75A105H-125A129E-144R differs from the precursor pTrX-HML-75A105H-125A129E by an additional mutation H144R. A new PCR reverse primer was used to create this mutation.

TX-144R-1r (SEQ ID NO:47 and 66; DNA and amino acid; respectively)
```
 159 158 157 156 155 154 153 152 151 150 149 148 147
  W   A   N   F   H   N   A   T   N   V   S   G   S
5'-CCA TGC ATT AAA GTG ATT CGC AGT ATT AAC CGA ACC GGA 146 145 144 143 142 141 140 139 138
 S   R   N   R   R   V   S   W
GCT CCG ACG ATT ACG TCT AAC ACT CCA
    NsiI
```

The appropriate PCR template and primers, and the restriction enzymes to cut the end of the PCR product which is the 1-146 sequence, are listed below (Table 3-8).

TABLE 3-8

| PCR product | Upstream primer | Downstream primer | Template | Restriction cut |
|---|---|---|---|---|
| (h) | TX-N1 | TX-144R-1r | pTrX-HML-75A105H-125A129E | PstI/NsiT |

The PstI/NsiI-cut PCR fragment (h) was ligated to the PstI/NsiI-linearized plasmid pTrX-del(43-53) to restore the functional xylanase gene in the new plasmid pTrX-HML-75A-105H-125A-129E-144R.

1-11: Construction of the Plasmid pTrX-HML-75A105H-125A129E-144R161R

The new mutant pTrX-HML-75A105H-125A129E-144R161 differs from the precursor pTrX-HML-75A105H-125A129E-144R by an additional mutation Q161R. A new PCR reverse primer was used to create this mutation.

TX-161R-1r (SEQ ID NO: 48 and 67; DNA and amino acid, respectively)
```
 168 167 166 165 164 163 162 161 160 159 158 157 156 155 154
  T   G   L   T   L   G   Q   R   A   W   A   N   F   H   N
5'-GT ACC TAG GGT TAA CCC TTG CCG TGC CCA TGC ATT AAA GTG ATT
      AvrII
```

A PCR product encoding the TrX(1-165) region was prepared as described in Table 3-9.

TABLE 3-9

Plasmid pTrX-HML-75A-105H-125A129E-144R as PCR template.

| PCR product | PCR upstream primer | PCR reverse primer | Restriction enzymes for PCR product |
|---|---|---|---|
| (i) | TX-N1 | TX-161R-1r | PsI/AvrII |

The PstI/AvrII-cut PCR fragment (i) was ligated to the PstI/AvrII-linearized plasmid pTrX-del(43-53) to restore the functional xylanase gene in the new plasmid pTrX-HML-75A-105H-125A-129E-144R161R.

1-12: Construction of the Plasmids pTrX-116G and pTrX-118C

The two new mutants are identical to TrX, with the major difference of an additional mutation, i.e. Asp-116 to Gly (D116G) or Tyr-118 to Cys (Y118C).

Two PCR primers were prepared with mutation (in bold type).

```
TX-116G-1 (SEQ ID NO:50 and 68; DNA and
amino acid, respectively)
   111 112 113 114 115 116 117 118 119
    D   G   S   V   Y   G   I   Y   R
5'-GAC GGA TCC GTA TAT GGT ATC TAC CG
       BamHI TX-118C-1 (SEQ ID NO:51 and 69; DNA and
amino acid, respectively)
   111 112 113 114 115 116 117 118 119 120 121 122
    D   G   S   V   Y   D   I   C   R   T   Q   R
5'-GAC GGA TCC GTA TAT GAT ATC TGC CGT ACC CAA CGC
       BamHI
```

The following plasmid template and primers are required for the two PCR:

TABLE 3-10

PCR with plasmid pTrX as template

| PCR product | PCR upstream primer | PCR reverse primer | Restriction cuts |
|---|---|---|---|
| (j) | TX-116G-1 | TX-C1 | BamHI/HindIII |
| (k) | TX-118C-1 | TX-C1 | BamHI/HindIII |

Ligation of the cut PCR products (j) and (k) to BamHI/HindIII-linearized plasmid pTrX-del(123-144) restored a functional xylanase gene in transformants harboring the respective plasmids pTrX-116G and pTrX-118C.

1-13: Construction of the Plasmids pTrX-HML-75A105H-116G-125A129E-144R and pTrX-HML-75A105H-118C-125A129E-144R The two new mutants were identical to the precursor TrX-HML-75A105H-125A129E-144R, with the major difference of an additional mutation, i.e. Asp-116 to Gly (D116G) or Tyr-118 to Cys (Y118C).

The following plasmid template and primers are required for the two PCR:

TABLE 3-11

PCR with plasmid pTrX-HML-75A105H-125A129E-144R as template

| PCR product | PCR upstream primer | PCR reverse primer | Restriction cuts |
|---|---|---|---|
| (l) | TX-116G-1 | TX-C1 | Bam-HI/HindIII |
| (m) | TX-118C-1 | TX-C1 | Bam-HI/HindIII |

Ligation of the cut PCR products (l) and (m) to the BamHI/HindIII-linearized plasmid pTrX-HML-75A105H-del(123-144) restored a functional xylanase gene in transformants harboring the respective plasmids pTrX-HML-75A105H-116G-125A129E-144R and pTrX-HML-75A105H-118C-125A129E-144R.

1-14: Construction of the Plasmids pTrX-H-11D-ML-75A105H-125A129E-144R161R, pTrX-H-11D-ML-75A105H-116G-125A129E-144R161R and pTrX-H-11D-ML-75A105H-118C-125A129E-144R161R The new mutants TrX-H-11D-ML-75A105H-125A129E-144R161R, TrX-H-11D-ML-75A105H-116G-125A129E-144R161R and TrX-H-11D-ML-75A105H-118C-125A129E-144R161R were identical to their respective precursors TrX-HML-75A105H-125A129E-144R, TrX-HML-75A105H-116G-125A129E-144R and TrX-HML-75A105H-118C-125A129E-144R, with the major difference of additional mutations, i.e. Asn-11 to Asp (N11D) and Gln-161 to Arg (Q161R). A new PCR primers was prepared with mutation N11D (in bold type).

```
TX-10H11D-1 (SEQ ID NO:52 and 70; DNA and
amino acid, respectively)
    6   7   8   9  10  11  12  13  14  15  16  17
    G   T   G   Y   H   D   G   Y   F   Y   S   Y
5'-GGA ACC GGT TAC CAC GAC GGT TAC TTT TAC AGC TAT
       AgeI
   18
    W
   TGG
```

TABLE 3-13

| PCR product | Upstream primer | Downstream primer | Template | Restriction cut |
|---|---|---|---|---|
| (n) | TX-10H11D-1 | TX-161R-1r | pTrX-HML-75A105H-125A129E-144R | AgeI/AvrII |
| (o) | TX-10H11D-1 | TX-161R-1r | pTrX-HML-75A105H-116G-125A129E-144R | AgeI/AvrII |
| (p) | TX-10H11D-1 | TX-161R-1r | pTrX-HML-75A105H-118C-125A128E-144R | AgeI/AvrII |

Ligation of the cut PCR products (n), (o) and (p) to AgeI/AvrII-cut plasmid pTrX-del(43-53) restored a functional xylanase gene in the transformant harboring the new plasmids pTrX-H-11D-ML-75A105H-125A129E-144R161R, pTrX- H-11D-ML-75A105H-116G-125A129E-144R161R and pTrX-H-11D-ML-75A105H-118C-125A129E-144R161R respectively

1-15: Construction of the Deletion Plasmid pTrX-H-11D-ML-75A105H-116G-del(123-144)

A plasmid containing partially deleted xylanase gene, were constructed via a PCR reaction with a new primer encoding the deletion of the (123-144) region, via a protocol identical to the EXAMPLE 1-9.

TABLE 3-14

| PCR template with TX-del(123-144)-1r and TX-N1 as primer | | |
|---|---|---|
| PCR product | PCR template | Restriction enzymes for PCR product |
| (q) | pTrX-H-11D-ML-75A105E-116G-125A129E-144R161R | PstI/SacI |

Ligation of the cut PCR fragment (q) to the PstI/SacI-linearized plasmid pTrX and transformation to yield the correct clones harboring the deletion plasmid pTrX-H-11D-ML-75A105H-116G-del(123-144), that were identified through non-expressing of xylanase and absence of halo or clearing zone in the blue xylan-containing YT plates.

1-16: Construction of the Plasmid pTrX-H-11D-ML-75A105H-116G118C-125A129E-144R161R The new mutant TrX-H-11D-ML-75A105H-116G118C-125A129E-144R161R was identical to its precursors TrX-H-11D-ML-75A105H-116G-125A129E-144R161R and TrX-H-11D-ML-75A105H-118C-125A129E-144R161R with the difference in the possession of combination mutation, Tyr-118 to Cys (Y118C) and Asp-116 to Gly (D116G). A new PCR primers was prepared with the combination mutation D116G/Y118C (in bold type).

```
TX-116G118C-1 (SEQ ID NO:53 and 71; DNA and
amino acid, respectively)
    111 112 113 114 115 116 117 118 119 120 121 122
     D   G   S   V   Y   G   I   C   R   T   Q   R
5'-GAC GGA TCC GTA TAT GGT ATC TGC CGT ACC CAA CGC
        BamHI
```

TABLE 3-15

| PCR to create (112-167) fragment containing the combination mutation | | | | |
|---|---|---|---|---|
| PCR product | Upstream primer | Downstream primer | Template | Restriction cut |
| (r) | TX-116G118C-1 | TX-161R-1r | rTrX-HML-75A105H-125A129E-144R | Bam-HI/AvrII |

Ligation of the cut PCR products (r) to BamHI/AvrII-cut plasmid pTrX-H-11D-ML-75A105H-116G-del(123-144) restored a functional xylanase gene in the transformant harboring the new plasmid pTrX-H-11D-ML-75A105H-116G118C-125A129E-144R161R.

Example 2

Characterization of Mutant Xylanases

2-1: Production of Xylanases

The culture conditions comprised a 5 ml culture of overnight innoculant in 2YT medium (16 g bacto-tryptone, 10 g yeast extract, 5 g NaCl, 1 L of water) containing ampicillin (100 mg/L) was added to 2YT medium (1 L) with ampicillin. The cultures were grown with shaking (200 rpm) at 37° C. After 16 hr, cells were harvested.

2-2: Purification of Mutant Xylanases

Protein samples were prepared from cells by first making an extract of the cells by grinding 10 g of the cell paste with 25 g of alumina powder. After grinding to smooth mixture, small amounts (5 mL) of ice cold buffer A (10 mM sodium acetate, pH 5.5 for BcX mutants) or buffer B (10 mM sodium acetate, pH 4.6 for TX mutants) were added and the mixture ground vigorously between additions. The alumina and cell debris were removed by centrifugation of the mixture at 8000×g for 30 min.

Prior to column chromatography, the supernatant was adjusted to pH 4.6 by acetic acid and centrifuged to remove any precipitate. The subsequent method for column chromatography was identical for all mutant xylanases.

Following acification and centrifugation, the xylanase sample was pumped onto a 50 ml bed volume, CM-sepharose fast flow, cation exchange column (Pharmacia Biotech, Uppsala), equilibrated in 10 mM sodium acetate (pH 4.6). The xylanase was eluted with a 250 ml linear gradient (0 to 0.6M NaCl in 10 mM sodium acetate, pH 4.6) at a flow rate of 1 ml/min. The xylanases elute at 150 to 200 ml of the gradient. Aliquots from the collected fractions are examined by SDS-PAGE, and those fractions having most of the xylanase present were pooled. The purified xylanase was quantified by spectrophotometry at 280 nm using an extinction coefficient between 54,600-53,400 $M^{-1}$, for most mutant TrX xylanases. A typical purification from 10 g of cells yielded 25 mg of xylanase.

2-3: Standard Assay for the Measurement of Enzymatic Activity

The quantitative assay determined the number of reducing sugar ends generated from soluble xylan. The substrate for this assay was the fraction of birchwood xylan which dissolved in water from a 5% suspension of birchwood xylan (Sigma Chemical Co.). After removing the insoluble fraction, the supernatant was freeze dried and stored in a dessicator. The measurement of specific activity was performed as follows: Reaction mixtures containing 100 µL of 30 mg/mL xylan previously diluted in assay buffer (50 mM sodium citrate, pH 5.5 or the pH optimum of the tested xylanase), 150 µL assay buffer, and 50 µL of enzyme diluted in assay buffer were incubated at 40° C. At various time intervals 50 µL portions were removed and the reaction stopped by diluting in 1 mL of 5 mM NaOH. The amount of reducing sugars was determined with the hydroxybenzoic acid hydrazide reagent (HBAH) (Lever, 1972, Analytical Biochem 47:273-279). A unit of enzyme activity was defined as that amount generating 1 µ mol reducing sugar in 1 minute at 40° C.

For comparison of the specific activities between mutant and native xylanases the specific activities of a mutant xylanase was converted to a relative activity. The relative activity is calculated as a percentage, by dividing the specific activity of the mutant enzyme by the specific activity of the native xylanase.

TABLE 4

Relative activity of mutant and native xylanases at 40° C. and pH 5.5.

| Xylanase | Relative activity |
| --- | --- |
| native TrX | 100* |
| TrX-HML-75A105H-116G-125A129E-144R | 84 |
| TrX-H-11D-ML-75A105H-116G-125A129E-144R161R | 80 |
| TrX-HML-75A105H-118C-125A129E-144R | 113 |
| TrX-H-11D-ML-75A105H-118C-125A129E-144R161R | 121 |

*Specific activity of native TrX xylanase determined to be 770 U/mg.

The results depicted in Table 4 indicate that the specific enzymatic activities of the mutant xylanases at 40° C. have not changed significantly as compared to the native xylanase. Rather, with the 118C mutant xylanases (TrX-HML-AHCAE-R, and TrX-H11D-ML-AHCAE-R) more activity is observed, when compared with the native xylanase (an increase in 13-21% in specific activity).

2-4: Determination of the Expression Efficiency of Mutant Xylanases by *E. coli*

Via the standard assay described in 2-3, the relative expression efficiency for each mutant xylanase has been determined, via an estimation of xylose release by the xylanase produced in unit volume of the bacterial culture. The three mutant xylanases encoding the mutation N11D, namely: TrX-H-11D-ML-75A105H-125A129E-144R161R (TrX-H11D-ML-AHAE-RR); TrX-H-11D-ML-75A105H-116G-125A129E-144R161R (TrX-H11D-ML-AHGAE-RR); and TrX-H-11D-ML-75A105H-118C-125A129E-144R161R (TrX-H11D-ML-AHCAERR) are 2.4-4.3 fold more efficiently expressed by *E. coli*, as compared to their respective precursors TrX-HML-75A105H-125A129E-144R161R, TrX-HML-75A105H-116G-125A129E-144R and TrX-HML-75A105H-118C-125A129E-144R without this mutation.

TABLE 5

Expression efficiency of mutant xylanases

| Xylanase | Relative expression efficiency* |
| --- | --- |
| TrX-H-11D-ML-75A105H-125A129E144R161R | 2.4 fold |
| TrX-H-11D-ML-75A105H-116G-125A129E-144R161R | 3.1 fold |
| TrX-H-11D-ML-75A105H-118C-125A129E-144R161R | 4.3 fold |

*Relative to the respective precursors as stated in the text above.

This indicates that one of the benefits of the mutation N11D is the enhancement of expression in microbes, a important characteristic for the industrial production of the enzyme.

Example 3

Thermophilicity of Mutant Xylanases

Thermophilicity was examined to test the effect of different temperatures on the enzymatic hydrolysis of soluble xylan by different mutant xylanases.

The assay procedure was similar to the standard assay with changes in the incubation temperature and time. The xylanases (15 µg/mL) and soluble birchwood xylan substrate, in 50 mM sodium citrate buffer of pH 5.5, were mixed and incubated in a circulating water bath at different temperatures. After a 30-min incubation, the amount of reducing sugars released from xylan was determined by HBAH analysis and was calculated as a relative activity, with the value at 40° C. representing 100%.

The effect of temperature on the hydrolysis of xylan by TrX-HML-75A105H-125A129E-144R (TrX-HML-AHAE-R) is shown in FIG. 3. Compared to the presursor without the H144R mutation (TrX-HML-AHAE), this mutant xylanase showed a moderately improved enzymatic activity at higher temperature. These results suggest that the H144R mutation improves the thermophilicity of xylanases.

Another mutant TrX-HML-75A105H-125A129E-144R161R (TrX-HML-AHAE-RR) did not significantly enhance the enzymatic activity at higher temperature (not shown), as compared to TrX-HML-75A105H-125A129E-144R (TrX-HML-AHAE-R). These results suggest that the Q161R mutation does not benfit the thermophilicity of xylanases.

Figure 4:
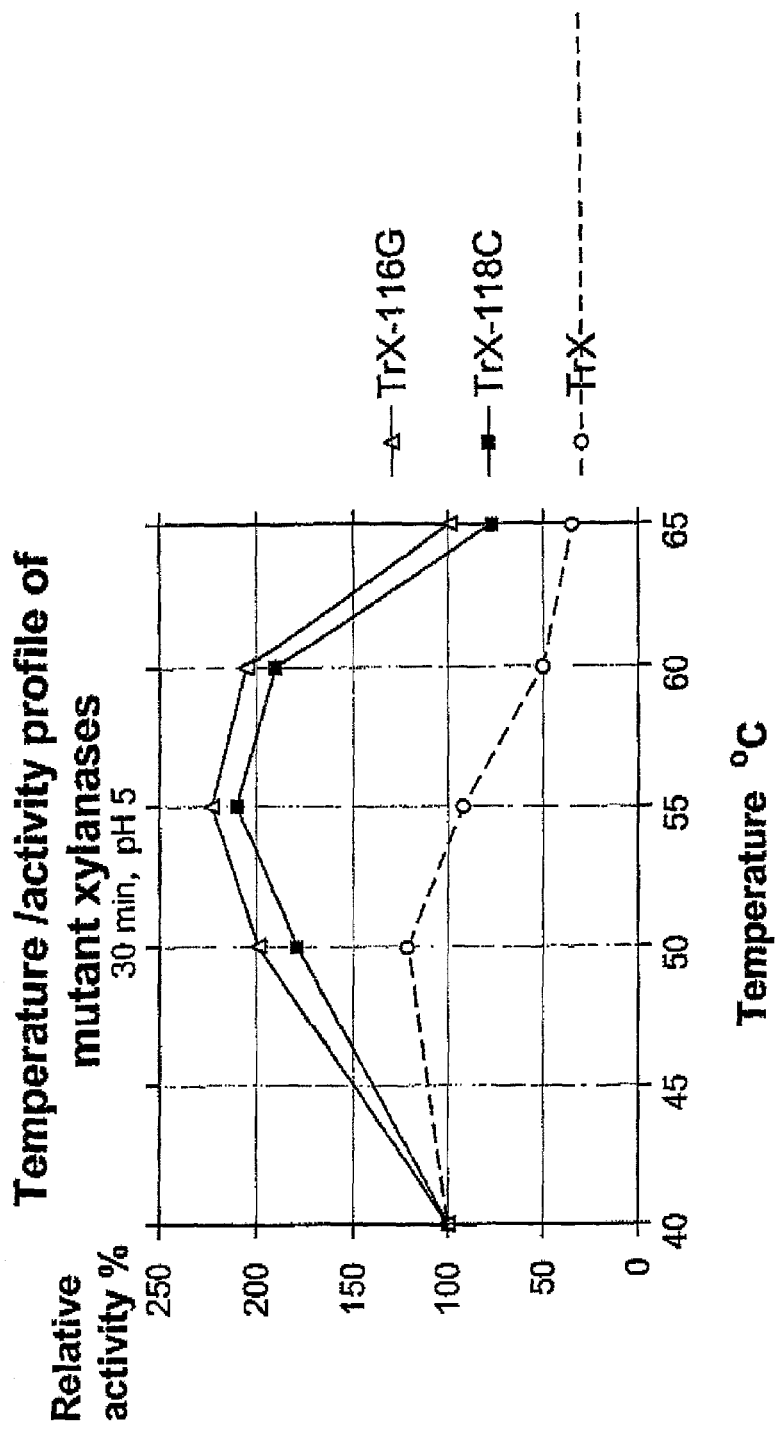
FIG. 4 shows the effect of temperature on the enzymatic activity of modified xylanases TrX-116G and TrX-118C, compared to native TrX, at pH 5.0 during 30-min incubations. The data are normalized to the activity observed at 40° C.
Figure 5:
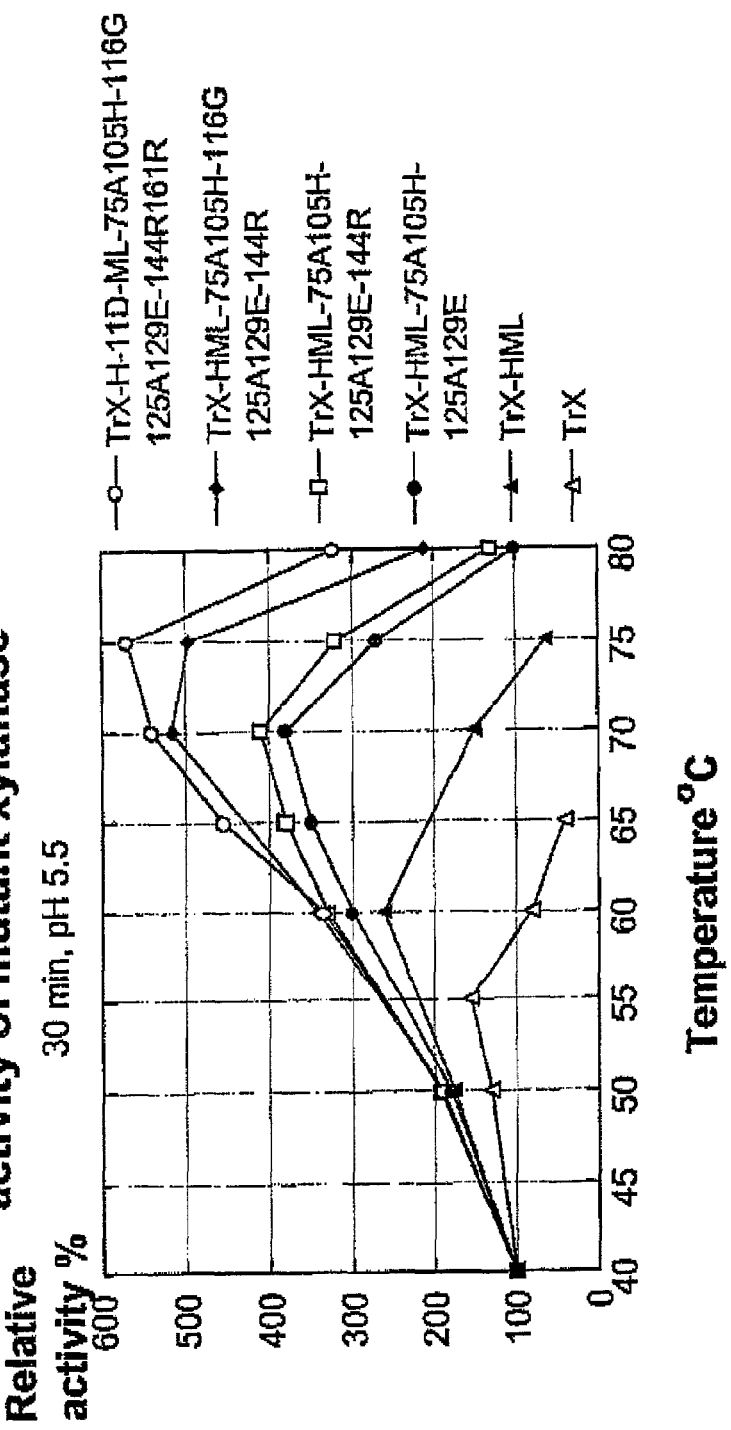
FIG. 5 shows the effect of temperature on the enzymatic activity of modified xylanases TrX-HML-75A105H-116G-125A129E-144R and TrX-H-11D-ML-75A105H-116G-125A129E-144R161R, as compared to native TrX, TrX-HML, TrX-HML-75A105H-125A129E and TrX-HML-75A105H-125A129E-144R, at pH 5.5 during 30-min incubations. The data are normalized to the activity observed at 40° C.

Two series of the mutants based on the mutations D116G and Y118C have been tested. Compared to native TrX, the single mutants TrX-116G and TrX-118C exhibit greater activity at higher temperatures (FIG. 4).

The same enhancing effect in thermophilicity was also observed in the next pairs of mutants: TrX-HML-75A105H-116G-125A129E-144R (TrX-HML-AHGAE-R); and TrX-HML-75A105H-118C-125A129E-144R (TrX-HML-AHCAE-R), as compared to the precursor TrX-HML-75A105H-125A129E-144R (Trx-HML-AHAE-R) at pH 5.5 (FIG. 5, only 116G mutant shown) and pH 6.0 (FIGS. 6 and 7; these figures comprise the same data but have different representation of the relative activity).

Another series of mutant xylanases based on the N11D mutation also benefits the thermophilicity. Mutant TrX-H-11D-ML-75A105H-125A129E-144R161R (TrX-H11D-ML-AHAE-RR) exhibited greater activity at higher temperatures, as compared to the precursor TrX-HML-75A105H-125A129E-144R (TrX-HML-AHAE-R; FIG. 8). This result is unexpected as prior art resports indicated the same N11D mutation either lowered the temperature optima and temperature range in TrX mutants containing an intramolecular disulfide bond (Turenen et. al., 2001), or no effect on thermophilicity of TrX-H-11D-ML was observed (U.S. Pat. No. 5,759,840; mutant termed NI-TX12). These data of the present invention indicate that the 11D mutation benefits appropriately modified xylanases.

The mutations identified above can be combined to create mutant xylanases with greater thermophilicity, even at higher pH range. The combination mutant xylanases, comprising triple mutations N11D/D116G/144R or N11D/Y118C/144R, namely: TrX-H-11D-ML-75A105H-116G-125A129E-144R161R (TrX-H11D-ML-AHGAE-RR); and TrX-H-11D-

ML-75A105H-118C-125A129E-144R161R (TrX-H11D-ML-AHCAE-RR), exhibit maximum enzymatic activity at a higher temperature of about 70 to about 75° C. and show significant enzymatic activity at 80° C. at pH 5.5 (FIG. 5, only 116G mutant shown), and pH 6.0 (FIGS. 6 and 7). These results suggest the effects of the mutations, D116G or Y118C, complement the mutations, N11D and H144R, with respect to thermophilicity of xylanase.

Example 4

Alkalophilicity of Mutant Xylanases

The alkalophilicity of genetically modified xylanases was examined to test the effect that different pH conditions had on the enzymatic hydrolysis of soluble birchwood xylan by mutant xylanases. The assay procedure was similar to the standard assay with changes in the incubation temperature and time. Aliquots of genetically modified xylanases (15 µg/mL) and soluble xylan substrate in 50 mM sodium citrate buffers which varied between pH 4-7 were incubated together at 65° C. Following 30 min incubations, the amount of reducing sugars released from the xylan substrate was determined by HBAH analysis and the enzymatic activity as a function of pH was calculated for a variety of mutant xylanases with the maximal activity taken as 100%.

The mutation H144R does not affect the activity at higher pH. The mutant TrX-HML-75A105H-125A129E-144R and its precursor TrX-HML-75A105H-125A129E have the same pH/activity profile (not shown). However, as noted in Example 3, this mutation (H144R) is beneficial to the thermophilicity of xylanase.

The effect of pH on the enzymatic activity by the mutation Q161R in the mutant xylanase TrX-HML-75A105H-125A129E-144R161R (TrX-HML-AHAE-RR) is shown in FIG. 9. Compared to its precursors TrX-HML-75A105H-125A129E and TrX-HML-75A105H-125A129E-144R (not shown), both of which have identical pH/activity profiles, the mutant xylanase TrX-HML-75A105H-125A129E-144R161R (TrX-HML-AHAE-RR) exhibits greater activity at a higher pH range of 6.5, 7.0, 7.5 and 8.0. TrX-HML-AHAE-RR also exhibits lower activity at lower pH of 5.0, 5.5 and 6.0, when compared to precursors without this mutation.

The direct effect of the mutations D116G and Y118C on xylanase activity have been tested. Compared to native TrX, the single mutants TrX-116G and TrX-118C have demonstrated greater activity at higher pH (FIG. 10).

The same enhancing effect in alkalophilicity by the mutations D116G and Y118C is also observed in the mutants: TrX-HML-75A105H-116G-125A129E-144R (TrX-HML-AHGAE-R); and TrX-HML-75A105H-118C-125A129E-144R (TrX-HML-AHCAE-R; FIG. 9), when compared to the precursors TrX-HML-75A105H-125A129E-144R and TrX-HML-75A105H-125A129E. While both of these mutants demonstrated higher activity at pH 6.5, 7.0, 7.5 and 8.0, the mutant TrX-HML-75A105H-116G-125A129E-144R retains optimal activity at the lower pH of 5.0, 5.5 and 6.0. This maintenance of high activity at pH 5.0-8.0 by both of these mutants represents a broadening of the optimal pH range.

The N11D mutation does not appear to contribute to the alkalophilicity of TrX. The mutant TrX-H-11D-ML-75A105H-125A129E-144R161R (TrX-H11DML-AHAE-RR) has identical pH/activity profile as its precursor TrX-HML-75A105H-125A129E-144R161R (not shown). The result, of 11D having no effect in the pH/activity profile, contradicts Turenen et al. (2001) who note that the N11D mutation lowered by pH optima and pH range in a TrX mutant containing an intramolecular disulfide bond. However, the results as described above agree with that in U.S. Pat. No. 5,759,840, where no negative effect on alkalophilicity of TrX-H-11D-ML (mutant termed NI-TX12) was observed.

Mutations identified above have been combined to create mutant xylanases with greater alkalophilicity and thermophilicity. The combination mutants xylanases based on quadruple mutations N11D/D116G/H144R/Q161R or N11D/Y118C/114R/Q161R, namely: TrX-H-11D-ML-75A105H-116G-125A129E-144R161R (TrX-H11D-ML-AHGAE-RR; FIG. 9); and TrX-H-11D-ML-75A105H-118C-125A129E-144R161R (TrX-H11D-ML-AHCAE-RR; SEQ ID NO:55), exhibit a maximum enzymatic activity from about pH 5.5 to about pH 7, as compared to precursor xylanases. Furthermore the presence of the mutation D116G helps the retain substantially maximal activity at a lower pH range of 5.0, 5.5 and 6.0, thus avoiding the significant loss of activity at low pH as observed in precursor TrX-HML-75A105H-125A129E-144R161R (FIG. 9). This result further confirms the broadening of the optimal pH range.

In summary, alkalophilic xylanase can be constructed through combination of mutations, D116G or Y118C with Q161R. Addition of other new mutations N11D and H144R can further enhance the thermophilicity of the mutant TrX. The N11D mutation may benefit the expression of the mutants.

While the present invention has described mutant xylanases which exhibit improved thermophilicity and alkalophilicity and the benefits associated with these enzymes in the production of paper pulp, these mutant xylanases may also be of use in other industrial processes, for example but not limited to the washing of precision devices and semiconductors. Further, by virtue their increased thermophilicity, and thermostability the mutant xylanases may be used in chemical processes that employ small quantities of denaturants or detergents or in the presence of solvents, for example but not limited to small amounts of apolar solvents such as but not limited to hexane, dioxanes, carbontetrachloride, benzene, ethers, chloroform, acetic acid and methylene chloride, and polar solvents such as but not limited to acetone, alcohols, dimethylformamide, acetonitrile, sulfolane, dimethylsulfoxide and water.

The present invention has been described with regard to preferred embodiments. However, it will be obvious to persons skilled in the art that a number of variations and modifications can be made without departing from the scope of the invention as described herein.

All references and citations are herein incorporated by reference

References

Arase, A., Yomo, T., Urabe, I., Hata, Y., Katsube, Y. and Okada, H. (1993) FEBS Lett. 316:123-127.

Casimir-Schenkel, J., Davis, S., Fiechter, a., Gysin, B., Murray, E., Perrolaz, J.-J. and Zimmermann, W. European Patent application no. 91810652.7, published on Apr. 3, 1992. Publication no. 0 473 545 A2.

Campbell, R. L., Rose, D. R., Sung, W. L., Yaguchi, M. and Wakarchuk, W. U.S. Pat. No. 5,405,769 issued on Apr. 11, 1995.

Campbell, R. L., Rose, D. R., Sung, W. L., Yaguchi, M. and Wakarchuk, W. PCT publication no. WO 94/24270, published on Oct. 27, 1994.

Chandra Raj, K. and Chandra, T. S. (1995) Biotechnol. Lett. 17: 309-314.

Fisk, R. S. and Simpson, C. (1993) in Stability and Stabilization of Enzymes, edited by W. J. J. van den Tweel, A. Harder and R. M. Buitelaar; published by Elsevier Science Publishers B. V. pp323-328.

Gruber, K., Klintschar, G., Hayn, M, Schlacher, A., Steiner, W. and Kratky, C. (1998) Biochemistry 37:13475-13485.

Irwin, D., Jung, E. D. and Wilson, D. B. (1994) Appl. Environ. Microbiol. 60:763-770.

Kinoshita, K., Takano, M., Koseki, T., Ito, K. and Iwano, K. (1995) J. Fermentation and Bioengineering 79:422-428.

Krengel, U. and Dijkstra (1996) J. Mol. Biol. 263:70-78.

Lee, S. L., Forsberg, C. W., and Rattray, J. B. (1987) Appl. Environ. Microbiol. 53:644-650.

Lüthi, E., Jasmat, N. B., and Bergquist, P. L. (1990) Appl. Environ. Microbiol. 56:2677-2683.

Mathrani, I. M. and Ahring, B. K. (1992) Appl. Microbiol. Biotechnol. 38:23-27.

Misset, O. (1993) in Stability and Stabilization of Enzymes, edited by W. J. J. van den Tweel, A. Harder and R. M. Buitelaar; published by Elsevier Science Publishers B. V. pp111-131.

Nissen A. M., Anker, L., Munk, N., and Lange, N. K. in Xylans and Xylanases, edited by J. Visser, G. Beldman, M. A. Kusters-van Someren and A. G. J. Voragen, published by Elsevier, Amsterdam, 1992, p325-337.

Sakka, K., Kojima Y., Kondo, T., Karita, S., Ohmiya, K. and Shimada, K. (1993) Biosci. Biotech. Biochem. 57:273-277.

Simpson, H. D., Haufler, U. R., and Daniel, R. M. (1991) Biochem. J. (1991) 277:413-417.

Sung, W. L., Yao, F.-L., Zahab, D. M. and Narang, S. A. (1986) Proc. Natl. Acad. Sci. USA 83:561-565.

Sung, W. L., Luk, C. K., Zahab, D. M. and Wakarchuk, W. (1993) Protein Expression Purif. 4:200-206.

Sung, W. L., Luk, C. K., Chan, B., Wakarchuk, W., Yaguchi, M., Campbell, R., Willick, G., Ishikawa, K. and Zabab, D. M. (1995) Biochem. Cell. Biol. 73:253-259.

Sung, W. L., Yaguchi, M and Ishikawa, K. U.S. Pat. No. 5,759,840, issued on Jun. 2, 1998.

Sung, W. L., Yaguchi, M and Ishikawa, K. U.S. Pat. No. 5,866,408, issued on Feb. 2, 1999

Sunna, A. And Antranikian, G. (1997) Crit. Rev. Biotech. 17:39-67.

Tolan, J. S. and Vega Canovas, R. (1992) Pulp & Paper Canada 93:116-119).

Turenen, O., Etuaho, K., Fenel, F., Vehmaanpera, J., Wu, X. Rouvinen, J. and Leisola, M. (2001) J. Biotech. 88:37-46.

Wakarchuck W. W., Sung, W. L., Campbell, R. L., Cunningham, A., Watson, D. C. and Yaguchi, M. (1994) Protein Engineering 7:1379-1386.

Wilson, D. B., Jung, E. D., Changas, G. S., Irvin, D. C. PCT international publication on 11 May 1995. Publication No. WO 95/12668.

Winterhalter C. and Liebl, W. (1995) Appl. Environ. Bicrobiol. 61:1810-1815.

Zappe, H., Jones, W. A., and Woods, D. R. (1987) Appl. Microbiol. Biotechnol. 27:57-63.

Zappe, H., Jones, W. A., and Woods, D. R. (1990) Nucleic Acids Res. 18:2179.

The invention claimed is:

1. A modified *Trichoderma reesei* xylanase II selected from the group consisting of:
   - a modified *Trichoderma reesei* xylanase II comprising TrX-N10H-Y27M-N29L-S75A-L105H-Q125A-I129E-H144R;
   - a modified *Trichoderma reesei* xylanase II comprising TrX-N10H-Y27M-N29L-S75A-L105H-Q125A-I129E-H144R-Q161R;
   - a modified *Trichoderma reesei* xylanase II comprising TrX-D116G;
   - a modified *Trichoderma reesei* xylanase II comprising TrX-Y118C;
   - a modified *Trichoderma reesei* xylanase II comprising TrX-H144R;
   - a modified *Trichoderma reesei* xylanase II comprising TrX-H144R-Q161R;
   - a modified *Trichoderma reesei* xylanase II comprising TrX-N10H-Y27M-N29L-S75A-L105H-D116G-Q125A-I129E-H144R;
   - a modified *Trichoderma reesei* xylanase II comprising TrX-N10H-Y27M-N29L-S75A-L105H-Y118C-Q125A-I129E-H144R;
   - a modified *Trichoderma reesei* xylanase II comprising TrX-N10H-N11D-Y27M-N29L-S75A-L105H-Q125A-I129E-H144R-Q161R;
   - a modified *Trichoderma reesei* xylanase II comprising TrX-N10H-N11D-Y27M-N29L-S75A-L105H-D116G-Q125A-I129E-H144R-Q161R;
   - a modified *Trichoderma reesei* xylanase II comprising TrX-N10H-N11D-Y27M-N29L-S75A-L105H-Y118C-Q125A-I129E-H144R-Q161R; and
   - a modified *Trichoderma reesei* xylanase II comprising TrX-N10H-N11D-Y27M-N29L-S75A-L105H-D116G-Y118C-Q125A-I129E-H144R-Q161R;

wherein the modified *Trichoderma reesei* xylanase II comprises an amino acid sequence that is from 93 to 99% identical to SEQ ID NO: 16, exhibits activity on a xylan substrate and improved thermophilicity in comparison to a corresponding native *Trichoderma reesei* xylanase II with an amino acid sequence as set forth in SEQ ID NO:16.

2. The modified *Trichoderma reesei* xylanase II of claim 1, wherein the modified *Trichoderma reesei* xylanase II exhibits improved alkalophilicity in comparison to a corresponding native xylanase.

3. The modified *Trichoderma reesei* xylanase II of claim 1 having a maximum effective temperature (MET) between about 69° C. and about 84° C.

4. The modified *Trichoderma reesei* xylanase II of claim 3, wherein the MET is between about 70° and about 84° C.

5. The modified *Trichoderma reesei* xylanase II of claim 1 having a maximum effective pH (MEP) between about pH 5.8 to about pH 8.4.

6. The modified *Trichoderma reesei* xylanase II of claim 5, wherein the MEP is between about pH 6.0 and about pH 8.0.

7. The modified *Trichoderma reesei* xylanase II of claim 3, wherein the modified xylanase is further characterized as having a maximum effective pH (MEP) between about pH 5.8 and about pH 7.6.

8. The modified *Trichoderma reesei* xylanase II of claim 4, wherein the modified xylanase is further characterized as having a maximum effective pH (MEP) between about pH 6.5 and about pH 7.4.

9. A method of manufacturing pulp, comprising treating the pulp with the modified *Trichoderma reesei* xylanase II of claim 1.

* * * * *

```
                        SEQUENCE LISTING

<160> NUMBER OF SEQ ID NOS: 71

<210> SEQ ID NO 1
<211> LENGTH: 184
<212> TYPE: PRT
<213> ORGANISM: Aspergillus niger

<400> SEQUENCE: 1

Ser Ala Gly Ile Asn Tyr Val Gln Asn Tyr Asn Gly Asn Leu Gly Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Thr Tyr Ser Ala Glu Tyr Ser Ala Ser Gly Ser Ser
    50                  55                  60

Ser Tyr Leu Ala Val Tyr Gly Trp Val Asn Tyr Pro Gly Ala Glu Tyr
65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Ile Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
    130                 135                 140

Val Ala Asn His Phe Asn Phe Trp Ala Gln His Gly Phe Gly Asn Ser
```

```
                145                 150                 155                 160
Asp Phe Asn Tyr Gln Val Met Ala Val Glu Ala Trp Ser Gly Ala Gly
                165                 170                 175
Ser Ala Ser Val Thr Ile Ser Ser
                180

<210> SEQ ID NO 2
<211> LENGTH: 185
<212> TYPE: PRT
<213> ORGANISM: Aspergillus tubigensis

<400> SEQUENCE: 2

Ser Ala Gly Ile Asn Tyr Val Gln Asn Tyr Asn Gln Asn Leu Gly Asp
1               5                   10                  15
Phe Thr Tyr Asp Glu Ser Ala Gly Thr Phe Ser Met Tyr Trp Glu Asp
                20                  25                  30
Gly Val Ser Ser Asp Phe Val Val Gly Leu Gly Gly Trp Thr Thr Gly
            35                  40                  45
Ser Ser Asn Ala Ile Thr Tyr Ser Ala Glu Tyr Ser Ala Ser Gly Ser
        50                  55                  60
Ala Ser Tyr Leu Ala Val Tyr Gly Trp Val Asn Tyr Pro Gln Ala Glu
65                  70                  75                  80
Tyr Tyr Ile Val Glu Asp Tyr Gly Asp Tyr Asn Pro Cys Ser Ser Ala
                85                  90                  95
Thr Ser Leu Gly Thr Val Tyr Ser Asp Gly Ser Thr Tyr Gln Val Cys
            100                 105                 110
Thr Asp Thr Arg Ile Asn Glu Pro Ser Ile Thr Gly Thr Ser Thr Phe
        115                 120                 125
Thr Gln Tyr Phe Ser Val Arg Glu Ser Thr Arg Thr Ser Gly Thr Val
    130                 135                 140
Thr Val Ala Asn His Phe Asn Phe Trp Ala His His Gly Phe His Asn
145                 150                 155                 160
Ser Asp Phe Asn Tyr Gln Val Val Ala Val Glu Ala Trp Ser Gly Ala
                165                 170                 175
Gly Ser Ala Ala Val Thr Ile Ser Ser
            180                 185

<210> SEQ ID NO 3
<211> LENGTH: 185
<212> TYPE: PRT
<213> ORGANISM: Bacillus circulans

<400> SEQUENCE: 3

Ala Ser Thr Asp Tyr Trp Gln Asn Trp Thr Asp Gly Gly Gly Ile Val
1               5                   10                  15
Asn Ala Val Asn Gly Ser Gly Gly Asn Tyr Ser Val Asn Trp Ser Asn
                20                  25                  30
Thr Gly Asn Phe Val Val Gly Lys Gly Trp Thr Thr Gly Ser Pro Phe
            35                  40                  45
Arg Thr Ile Asn Tyr Asn Ala Gly Val Trp Ala Pro Asn Gly Asn Gly
        50                  55                  60
Tyr Leu Thr Leu Tyr Gly Trp Thr Arg Ser Pro Leu Ile Glu Tyr Tyr
65                  70                  75                  80
Val Val Asp Ser Trp Gly Thr Tyr Arg Pro Thr Gly Thr Tyr Lys Gly
                85                  90                  95
Thr Val Lys Ser Asp Gly Gly Thr Tyr Asp Ile Tyr Thr Thr Thr Arg
```

```
                100             105             110
Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Ala Thr Ile
        130                 135                 140

Thr Phe Thr Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 4
<211> LENGTH: 201
<212> TYPE: PRT
<213> ORGANISM: Bacillus pumilus

<400> SEQUENCE: 4

Arg Thr Ile Thr Asn Asn Glu Met Gly Asn His Ser Gly Tyr Asp Tyr
1               5                   10                  15

Glu Leu Trp Lys Asp Tyr Gly Asn Thr Ser Met Thr Leu Asn Asn Gly
            20                  25                  30

Gly Ala Phe Ser Ala Gly Trp Asn Asn Ile Gly Asn Ala Leu Phe Arg
        35                  40                  45

Lys Gly Lys Lys Phe Asp Ser Thr Arg Thr His His Gln Leu Gly Asn
50                  55                  60

Ile Ser Ile Asn Tyr Asn Ala Ser Phe Asn Pro Ser Gly Asn Ser Tyr
65                  70                  75                  80

Leu Cys Val Tyr Gly Trp Thr Gln Ser Pro Leu Ala Glu Tyr Tyr Ile
                85                  90                  95

Val Asp Ser Trp Gly Thr Tyr Arg Pro Thr Gly Ala Tyr Lys Gly Ser
            100                 105                 110

Phe Tyr Ala Asp Gly Gly Thr Tyr Asp Ile Tyr Glu Thr Thr Arg Val
        115                 120                 125

Asn Gln Pro Ser Ile Ile Gly Ile Ala Thr Phe Lys Gln Tyr Trp Ser
    130                 135                 140

Val Arg Gln Thr Lys Arg Thr Ser Gly Thr Val Ser Val Ser Ala His
145                 150                 155                 160

Phe Arg Lys Trp Glu Ser Leu Gly Met Pro Met Gly Lys Met Tyr Glu
                165                 170                 175

Thr Ala Phe Thr Val Glu Gly Tyr Gln Ser Ser Gly Ser Ala Asn Val
            180                 185                 190

Met Thr Asn Gln Leu Phe Ile Gly Asn
        195                 200

<210> SEQ ID NO 5
<211> LENGTH: 185
<212> TYPE: PRT
<213> ORGANISM: Bacillus subtilus

<400> SEQUENCE: 5

Ala Ser Thr Asp Tyr Trp Gln Asn Trp Thr Asp Gly Gly Gly Ile Val
1               5                   10                  15

Asn Ala Val Asn Gly Ser Gly Gly Asn Tyr Ser Val Asn Trp Ser Asn
            20                  25                  30

Thr Gly Asn Phe Val Val Gly Lys Gly Trp Thr Thr Gly Ser Pro Phe
```

```
                35                  40                  45
Arg Thr Ile Asn Tyr Asn Ala Gly Val Trp Ala Pro Asn Gly Asn Gly
 50                  55                  60

Tyr Leu Thr Leu Tyr Gly Trp Thr Arg Ser Pro Leu Ile Glu Tyr Tyr
65                  70                  75                  80

Val Val Asp Ser Trp Gly Thr Tyr Arg Pro Thr Gly Thr Tyr Lys Gly
                85                  90                  95

Thr Val Lys Ser Asp Gly Gly Thr Tyr Asp Ile Tyr Thr Thr Thr Arg
            100                 105                 110

Tyr Asn Ala Pro Ser Ile Asp Gly Asp Arg Thr Thr Phe Thr Gln Tyr
            115                 120                 125

Trp Ser Val Arg Gln Ser Lys Arg Pro Thr Gly Ser Asn Ala Thr Ile
130                 135                 140

Thr Phe Ser Asn His Val Asn Ala Trp Lys Ser His Gly Met Asn Leu
145                 150                 155                 160

Gly Ser Asn Trp Ala Tyr Gln Val Met Ala Thr Glu Gly Tyr Gln Ser
                165                 170                 175

Ser Gly Ser Ser Asn Val Thr Val Trp
            180                 185

<210> SEQ ID NO 6
<211> LENGTH: 211
<212> TYPE: PRT
<213> ORGANISM: Clostridium acetobutylicum

<400> SEQUENCE: 6

Ser Ala Phe Asn Thr Gln Ala Ala Pro Lys Thr Ile Thr Ser Asn Glu
1               5                   10                  15

Ile Gly Val Asn Gly Gly Tyr Asp Tyr Glu Leu Trp Lys Asp Tyr Gly
                20                  25                  30

Asn Thr Ser Met Thr Leu Lys Asn Gly Gly Ala Phe Ser Cys Gln Trp
            35                  40                  45

Ser Asn Ile Gly Asn Ala Leu Phe Arg Lys Gly Lys Lys Phe Asn Asp
 50                  55                  60

Thr Gln Thr Tyr Lys Gln Leu Gly Asn Ile Ser Val Asn Tyr Asn Cys
65                  70                  75                  80

Asn Tyr Gln Pro Tyr Gly Asn Ser Tyr Leu Cys Val Tyr Gly Trp Thr
                85                  90                  95

Ser Ser Pro Leu Val Glu Tyr Tyr Ile Val Asp Ser Trp Gly Ser Trp
            100                 105                 110

Arg Pro Pro Gly Gly Thr Ser Lys Gly Thr Ile Thr Val Asp Gly Gly
            115                 120                 125

Ile Tyr Asp Ile Tyr Glu Thr Thr Arg Ile Asn Gln Pro Ser Ile Gln
130                 135                 140

Gly Asn Thr Thr Phe Lys Gln Tyr Trp Ser Val Arg Arg Thr Lys Arg
145                 150                 155                 160

Thr Ser Gly Thr Ile Ser Val Ser Lys His Phe Ala Ala Trp Glu Ser
                165                 170                 175

Lys Gly Met Pro Leu Gly Lys Met His Glu Thr Ala Phe Asn Ile Glu
            180                 185                 190

Gly Tyr Gln Ser Ser Gly Lys Ala Asp Val Asn Ser Met Ser Ile Asn
            195                 200                 205

Ile Gly Lys
    210
```

<210> SEQ ID NO 7
<211> LENGTH: 206
<212> TYPE: PRT
<213> ORGANISM: Clostridium stercocrarium

<400> SEQUENCE: 7

```
Gly Arg Ile Ile Tyr Asp Asn Glu Thr Gly Thr His Gly Gly Tyr Asp
1               5                   10                  15

Tyr Glu Leu Trp Lys Asp Tyr Gly Asn Thr Ile Met Glu Leu Asn Asp
            20                  25                  30

Gly Gly Thr Phe Ser Cys Gln Trp Ser Asn Ile Gly Asn Ala Leu Phe
        35                  40                  45

Arg Lys Gly Arg Lys Phe Asn Ser Asp Lys Thr Tyr Gln Glu Leu Gly
    50                  55                  60

Asp Ile Val Val Glu Tyr Gly Cys Asp Tyr Asn Pro Asn Gly Asn Ser
65                  70                  75                  80

Tyr Leu Cys Val Tyr Gly Trp Thr Arg Asn Phe Leu Val Glu Tyr Tyr
                85                  90                  95

Ile Val Glu Ser Trp Gly Ser Trp Arg Pro Pro Gly Ala Thr Pro Lys
            100                 105                 110

Gly Thr Ile Thr Gln Trp Met Ala Gly Thr Tyr Glu Ile Tyr Glu Thr
        115                 120                 125

Thr Arg Val Asn Gln Pro Ser Ile Asp Gly Thr Ala Thr Phe Gln Gln
    130                 135                 140

Tyr Trp Ser Val Arg Thr Ser Lys Arg Thr Ser Gly Thr Ile Ser Val
145                 150                 155                 160

Thr Glu His Phe Lys Gln Trp Glu Arg Met Gly Met Arg Met Gly Lys
                165                 170                 175

Met Tyr Glu Val Ala Leu Thr Val Glu Gly Tyr Gln Ser Ser Gly Tyr
            180                 185                 190

Ala Asn Val Tyr Lys Asn Glu Ile Arg Ile Gly Ala Asn Pro
        195                 200                 205
```

<210> SEQ ID NO 8
<211> LENGTH: 211
<212> TYPE: PRT
<213> ORGANISM: Ruminoccus flavefaciens

<400> SEQUENCE: 8

```
Ser Ala Ala Asp Gln Gln Thr Arg Gly Asn Val Gly Gly Tyr Asp Tyr
1               5                   10                  15

Glu Met Trp Asn Gln Asn Gly Gln Gly Gln Ala Ser Met Asn Pro Gly
            20                  25                  30

Ala Gly Ser Phe Thr Cys Ser Trp Ser Asn Ile Glu Asn Phe Leu Ala
        35                  40                  45

Arg Met Gly Lys Asn Tyr Asp Ser Gln Lys Lys Asn Tyr Lys Ala Phe
    50                  55                  60

Gly Asn Ile Val Leu Thr Tyr Asp Val Glu Tyr Thr Pro Arg Gly Asn
65                  70                  75                  80

Ser Tyr Met Cys Val Tyr Gly Trp Thr Arg Asn Pro Leu Met Glu Tyr
                85                  90                  95

Tyr Ile Val Glu Gly Trp Gly Asp Trp Arg Pro Pro Gly Asn Asp Gly
            100                 105                 110

Glu Val Lys Gly Thr Val Ser Ala Asn Gly Asn Thr Tyr Asp Ile Arg
        115                 120                 125
```

```
Lys Thr Met Arg Tyr Asn Gln Pro Ser Leu Asp Gly Thr Ala Thr Phe
    130                 135                 140

Pro Gln Tyr Trp Ser Val Arg Gln Thr Ser Gly Ser Ala Asn Asn Gln
145                 150                 155                 160

Thr Asn Tyr Met Lys Gly Thr Ile Asp Val Ser Lys His Phe Asp Ala
                165                 170                 175

Trp Ser Ala Ala Gly Leu Asp Met Ser Gly Thr Leu Tyr Glu Val Ser
            180                 185                 190

Leu Asn Ile Glu Gly Tyr Arg Ser Asn Gly Ser Ala Asn Val Lys Ser
        195                 200                 205

Val Ser Val
    210

<210> SEQ ID NO 9
<211> LENGTH: 197
<212> TYPE: PRT
<213> ORGANISM: Schizophyllum cimmune

<400> SEQUENCE: 9

Ser Gly Thr Pro Ser Ser Thr Gly Thr Asp Gly Gly Tyr Tyr Tyr Ser
1               5                   10                  15

Trp Trp Thr Asp Gly Ala Gly Asp Ala Thr Tyr Gln Asn Asn Gly Gly
                20                  25                  30

Gly Ser Tyr Thr Leu Thr Trp Ser Gly Asn Asn Gly Asn Leu Val Gly
            35                  40                  45

Gly Lys Gly Trp Asn Pro Gly Ala Ala Ser Arg Ser Ile Ser Tyr Ser
50                  55                  60

Gly Thr Tyr Gln Pro Asn Gly Asn Ser Tyr Leu Ser Val Tyr Gly Trp
65                  70                  75                  80

Thr Arg Ser Ser Leu Ile Glu Tyr Tyr Ile Val Glu Ser Tyr Gly Ser
                85                  90                  95

Tyr Asp Pro Ser Ser Ala Ala Ser His Lys Gly Ser Val Thr Cys Asn
            100                 105                 110

Gly Ala Thr Tyr Asp Ile Leu Ser Thr Trp Arg Tyr Asn Ala Pro Ser
        115                 120                 125

Ile Asp Gly Thr Gln Thr Phe Glu Gln Phe Trp Ser Val Arg Asn Pro
130                 135                 140

Lys Lys Ala Pro Gly Gly Ser Ile Ser Gly Thr Val Asp Val Gln Cys
145                 150                 155                 160

His Phe Asp Ala Trp Lys Gly Leu Gly Met Asn Leu Gly Ser Glu His
                165                 170                 175

Asn Tyr Gln Ile Val Ala Thr Glu Gly Tyr Gln Ser Ser Gly Thr Ala
            180                 185                 190

Thr Ile Thr Val Thr
        195

<210> SEQ ID NO 10
<211> LENGTH: 191
<212> TYPE: PRT
<213> ORGANISM: Streptomyces lividans Xyl B

<400> SEQUENCE: 10

Asp Thr Val Val Thr Thr Asn Gln Glu Gly Thr Asn Asn Gly Tyr Tyr
1               5                   10                  15

Tyr Ser Phe Trp Thr Asp Ser Gln Gly Thr Val Ser Met Asn Met Gly
                20                  25                  30
```

-continued

Ser Gly Gly Gln Tyr Ser Thr Ser Trp Arg Asn Thr Gly Asn Phe Val
                35                  40                  45

Ala Gly Lys Gly Trp Ala Asn Gly Gly Arg Arg Thr Val Gln Tyr Ser
         50                  55                  60

Gly Ser Phe Asn Pro Ser Gly Asn Ala Tyr Leu Ala Leu Tyr Gly Trp
 65                  70                  75                  80

Thr Ser Asn Pro Leu Val Glu Tyr Tyr Ile Val Asp Asn Trp Gly Thr
                 85                  90                  95

Tyr Arg Pro Thr Gly Glu Tyr Lys Gly Thr Val Thr Ser Asp Gly Gly
            100                 105                 110

Thr Tyr Asp Ile Tyr Lys Thr Thr Arg Val Asn Lys Pro Ser Val Glu
        115                 120                 125

Gly Thr Arg Thr Phe Asp Gln Tyr Trp Ser Val Arg Gln Ser Lys Arg
130                 135                 140

Thr Gly Gly Thr Ile Thr Thr Gly Asn His Phe Asp Ala Trp Ala Arg
145                 150                 155                 160

Ala Gly Met Pro Leu Gly Asn Phe Ser Tyr Tyr Met Ile Asn Ala Thr
                165                 170                 175

Glu Gly Tyr Gln Ser Ser Gly Thr Ser Ser Ile Asn Val Gly Gly
            180                 185                 190

<210> SEQ ID NO 11
<211> LENGTH: 191
<212> TYPE: PRT
<213> ORGANISM: Streptomyces lividans Xyl C

<400> SEQUENCE: 11

Ala Thr Thr Ile Thr Thr Asn Gln Thr Gly Thr Asp Gly Met Tyr Tyr
 1               5                  10                  15

Ser Phe Trp Thr Asp Gly Gly Gly Ser Val Ser Met Thr Leu Asn Gly
                20                  25                  30

Gly Gly Ser Tyr Ser Thr Gln Trp Thr Asn Cys Gly Asn Phe Val Ala
            35                  40                  45

Gly Lys Gly Trp Ser Thr Gly Asp Gly Asn Val Arg Tyr Asn Gly Tyr
 50                  55                  60

Phe Asn Pro Val Gly Asn Gly Tyr Gly Cys Leu Tyr Gly Trp Thr Ser
 65                  70                  75                  80

Asn Pro Leu Val Glu Tyr Tyr Ile Val Asp Asn Trp Gly Ser Tyr Arg
                 85                  90                  95

Pro Thr Gly Thr Tyr Lys Gly Thr Val Ser Ser Asp Gly Gly Thr Tyr
            100                 105                 110

Asp Ile Tyr Gln Thr Thr Arg Tyr Asn Ala Pro Ser Val Glu Gly Thr
        115                 120                 125

Lys Thr Phe Gln Gln Tyr Trp Ser Val Arg Gln Ser Lys Val Thr Ser
    130                 135                 140

Gly Ser Gly Thr Ile Thr Thr Gly Asn His Phe Asp Ala Trp Ala Arg
145                 150                 155                 160

Ala Gly Met Asn Met Gly Gln Phe Arg Tyr Tyr Met Ile Asn Ala Thr
                165                 170                 175

Glu Gly Tyr Gln Ser Ser Gly Ser Ser Asn Ile Thr Val Ser Gly
            180                 185                 190

<210> SEQ ID NO 12
<211> LENGTH: 189
<212> TYPE: PRT
<213> ORGANISM: Streptomyces sp. No. 36a

<400> SEQUENCE: 12

```
Ala Thr Thr Ile Thr Asn Glu Thr Gly Tyr Asp Gly Met Tyr Tyr Ser
1               5                   10                  15

Phe Trp Thr Asp Gly Gly Ser Val Ser Met Thr Leu Asn Gly Gly
            20                  25                  30

Gly Ser Tyr Ser Thr Arg Trp Thr Asn Cys Gly Asn Phe Val Ala Gly
            35                  40                  45

Lys Gly Trp Ala Asn Gly Gly Arg Arg Thr Val Arg Tyr Thr Gly Trp
            50                  55                  60

Phe Asn Pro Ser Gly Asn Gly Tyr Gly Cys Leu Tyr Gly Trp Thr Ser
65                  70                  75                  80

Asn Pro Leu Val Glu Tyr Tyr Ile Val Asp Asn Trp Gly Ser Tyr Arg
                85                  90                  95

Pro Thr Gly Glu Thr Arg Gly Thr Val His Ser Asp Gly Gly Thr Tyr
            100                 105                 110

Asp Ile Tyr Lys Thr Thr Arg Tyr Asn Ala Pro Ser Val Glu Ala Pro
            115                 120                 125

Ala Ala Phe Asp Gln Tyr Trp Ser Val Arg Gln Ser Lys Val Thr Ser
            130                 135                 140

Gly Thr Ile Thr Thr Gly Asn His Phe Asp Ala Trp Ala Arg Ala Gly
145                 150                 155                 160

Met Asn Met Gly Asn Phe Arg Tyr Tyr Met Ile Asn Ala Thr Glu Gly
                165                 170                 175

Tyr Gln Ser Ser Gly Ser Ser Thr Ile Thr Val Ser Gly
            180                 185
```

<210> SEQ ID NO 13
<211> LENGTH: 189
<212> TYPE: PRT
<213> ORGANISM: Thermomonospora fusca

<400> SEQUENCE: 13

```
Ala Val Thr Ser Asn Glu Thr Gly Tyr His Asp Gly Tyr Phe Tyr Ser
1               5                   10                  15

Phe Trp Thr Asp Ala Pro Gly Thr Val Ser Met Glu Leu Gly Pro Gly
            20                  25                  30

Gly Asn Tyr Ser Thr Ser Trp Arg Asn Thr Gly Asn Phe Val Ala Gly
            35                  40                  45

Lys Gly Trp Ala Thr Gly Gly Arg Arg Thr Val Thr Tyr Ser Ala Ser
            50                  55                  60

Phe Asn Pro Ser Gly Asn Ala Tyr Leu Thr Leu Tyr Gly Trp Thr Arg
65                  70                  75                  80

Asn Pro Leu Val Glu Tyr Tyr Ile Val Glu Ser Trp Gly Thr Tyr Arg
                85                  90                  95

Pro Thr Gly Thr Tyr Met Gly Thr Val Thr Thr Asp Gly Gly Thr Tyr
            100                 105                 110

Asp Ile Tyr Lys Thr Thr Arg Tyr Asn Ala Pro Ser Ile Glu Gly Thr
            115                 120                 125

Arg Thr Phe Asp Gln Tyr Trp Ser Val Arg Gln Ser Lys Arg Thr Ser
            130                 135                 140

Gly Thr Ile Thr Ala Gly Asn His Phe Asp Ala Trp Ala Arg His Gly
145                 150                 155                 160

Met His Leu Gly Thr His Asp Tyr Met Ile Met Ala Thr Glu Gly Tyr
                165                 170                 175
```

Gln Ser Ser Gly Ser Ser Asn Val Thr Leu Gly Thr Ser
            180                 185

<210> SEQ ID NO 14
<211> LENGTH: 190
<212> TYPE: PRT
<213> ORGANISM: Trichoderma harzanium

<400> SEQUENCE: 14

Gln Thr Ile Gly Pro Gly Thr Gly Tyr Ser Asn Gly Tyr Tyr Tyr Ser
1               5                   10                  15

Tyr Trp Asn Asp Gly His Ala Gly Val Thr Tyr Thr Asn Gly Gly Gly
            20                  25                  30

Gly Ser Phe Thr Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Ile Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Ser His Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 15
<211> LENGTH: 178
<212> TYPE: PRT
<213> ORGANISM: Trichoderma ressei Xyl I

<400> SEQUENCE: 15

Ala Ser Ile Asn Tyr Asp Gln Asn Tyr Gln Thr Gly Gly Gln Val Ser
1               5                   10                  15

Tyr Ser Pro Ser Asn Thr Gly Phe Ser Val Asn Trp Asn Thr Gln Asp
            20                  25                  30

Asp Phe Val Val Gly Val Gly Trp Thr Thr Gly Ser Ser Ala Pro Ile
        35                  40                  45

Asn Phe Gly Gly Ser Phe Ser Val Asn Ser Gly Thr Gly Leu Leu Ser
    50                  55                  60

Val Tyr Gly Trp Ser Thr Asn Pro Leu Val Glu Tyr Tyr Ile Met Glu
65                  70                  75                  80

Asp Asn His Asn Tyr Pro Ala Gln Gly Thr Val Lys Gly Thr Val Thr
                85                  90                  95

Ser Asp Gly Ala Thr Tyr Thr Ile Trp Glu Asn Thr Arg Val Asn Glu
            100                 105                 110

Pro Ser Ile Gln Gly Thr Ala Thr Phe Asn Gln Tyr Ile Ser Val Arg
        115                 120                 125

```
Asn Ser Pro Arg Thr Ser Gly Thr Val Thr Val Gln Asn His Phe Asn
    130                 135                 140

Trp Ala Ser Leu Gly Leu His Leu Gly Gln Met Met Asn Tyr Gln Val
145                 150                 155                 160

Val Ala Val Glu Gly Trp Gly Ser Gly Ser Ala Ser Gln Ser Val
                165                 170                 175

Ser Asn

<210> SEQ ID NO 16
<211> LENGTH: 190
<212> TYPE: PRT
<213> ORGANISM: Trichoderma ressei Xyl II

<400> SEQUENCE: 16

Gln Thr Ile Gln Pro Gly Thr Gly Tyr Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Asn His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 17
<211> LENGTH: 190
<212> TYPE: PRT
<213> ORGANISM: Trichoderma viride

<400> SEQUENCE: 17

Gln Thr Ile Gln Pro Gly Thr Gly Phe Asn Asn Gly Tyr Phe Tyr Ser
1               5                   10                  15

Tyr Trp Asn Asp Gly His Gly Gly Val Thr Tyr Thr Asn Gly Pro Gly
            20                  25                  30

Gly Gln Phe Ser Val Asn Trp Ser Asn Ser Gly Asn Phe Val Gly Gly
        35                  40                  45

Lys Gly Trp Gln Pro Gly Thr Lys Asn Lys Val Ile Asn Phe Ser Gly
    50                  55                  60

Ser Tyr Asn Pro Asn Gly Asn Ser Tyr Leu Ser Val Tyr Gly Trp Ser
65                  70                  75                  80
```

-continued

```
Arg Asn Pro Leu Ile Glu Tyr Tyr Ile Val Glu Asn Phe Gly Thr Tyr
                85                  90                  95

Asn Pro Ser Thr Gly Ala Thr Lys Leu Gly Glu Val Thr Ser Asp Gly
            100                 105                 110

Ser Val Tyr Asp Ile Tyr Arg Thr Gln Arg Val Asn Gln Pro Ser Ile
        115                 120                 125

Ile Gly Thr Ala Thr Phe Tyr Gln Tyr Trp Ser Val Arg Arg Thr His
    130                 135                 140

Arg Ser Ser Gly Ser Val Asn Thr Ala Asn His Phe Asn Ala Trp Ala
145                 150                 155                 160

Gln Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
            180                 185                 190

<210> SEQ ID NO 18
<211> LENGTH: 202
<212> TYPE: PRT
<213> ORGANISM: Fibrobacter succinognees

<400> SEQUENCE: 18

Asn Ser Ser Val Thr Gly Asn Val Gly Ser Pro Tyr His Tyr Glu
1               5                   10                  15

Ile Trp Tyr Gln Gly Gly Asn Asn Ser Met Thr Phe Tyr Asp Asn Gly
                20                  25                  30

Thr Tyr Lys Ala Ser Trp Asn Gly Thr Asn Asp Phe Leu Ala Arg Val
            35                  40                  45

Gly Phe Lys Tyr Asp Glu Lys His Thr Tyr Glu Glu Leu Gly Pro Ile
        50                  55                  60

Asp Ala Tyr Tyr Lys Trp Ser Lys Gln Gly Ser Ala Gly Gly Tyr Asn
65                  70                  75                  80

Tyr Ile Gly Ile Tyr Gly Trp Thr Val Asp Pro Leu Val Glu Tyr Tyr
                85                  90                  95

Ile Val Asp Asp Trp Phe Asn Lys Pro Gly Ala Asn Leu Leu Gly Gln
            100                 105                 110

Arg Lys Gly Glu Phe Thr Val Asp Gly Asp Thr Tyr Glu Ile Trp Gln
        115                 120                 125

Asn Thr Arg Val Gln Gln Pro Ser Ile Lys Gly Thr Gln Thr Phe Pro
    130                 135                 140

Gln Tyr Phe Ser Val Arg Lys Ser Ala Arg Ser Cys Gly His Ile Asp
145                 150                 155                 160

Ile Thr Ala His Met Lys Lys Trp Glu Glu Leu Gly Met Lys Met Gly
                165                 170                 175

Lys Met Tyr Glu Ala Lys Val Leu Val Glu Ala Gly Gly Ser Gly
            180                 185                 190

Ser Phe Asp Val Thr Tyr Phe Lys Met Thr
        195                 200

<210> SEQ ID NO 19
<211> LENGTH: 189
<212> TYPE: PRT
<213> ORGANISM: Asparigillus awamori var. kawachi

<400> SEQUENCE: 19

Arg Ser Thr Pro Ser Ser Thr Gly Glu Asn Asn Gly Tyr Tyr Tyr Ser
1               5                   10                  15
```

```
Phe Trp Thr Asp Gly Gly Asp Val Thr Tyr Thr Asn Gly Asn Ala
                20              25              30
Gly Ser Tyr Ser Val Glu Trp Ser Asn Val Gly Asn Phe Val Gly
            35              40              45
Lys Gly Trp Asn Pro Gly Ser Ala Lys Asp Ile Thr Tyr Ser Gly Asn
 50              55              60
Phe Thr Pro Ser Gly Asn Gly Tyr Leu Ser Val Tyr Gly Trp Thr Thr
 65              70              75              80
Asp Pro Leu Ile Glu Tyr Tyr Ile Val Glu Ser Tyr Gly Asp Tyr Asn
                85              90              95
Pro Gly Ser Gly Gly Thr Thr Arg Gly Asn Val Ser Ser Asp Gly Ser
                100             105             110
Val Tyr Asp Ile Tyr Thr Ala Thr Arg Thr Asn Ala Pro Ser Ile Asp
                115             120             125
Gly Thr Gln Thr Phe Ser Gln Tyr Trp Ser Val Arg Gln Asn Lys Arg
 130             135             140
Val Gly Gly Thr Val Thr Thr Ser Asn His Phe Asn Ala Trp Ala Lys
145             150             155             160
Leu Gly Met Asn Leu Gly Thr His Asn Tyr Gln Ile Leu Ala Thr Glu
                165             170             175
Gly Tyr Gln Ser Ser Gly Ser Ser Ser Ile Thr Ile Gln
                180             185

<210> SEQ ID NO 20
<211> LENGTH: 194
<212> TYPE: PRT
<213> ORGANISM: Thermomyces lanuginosus

<400> SEQUENCE: 20

Gln Thr Thr Pro Asn Ser Glu Gly Trp His Asp Gly Tyr Tyr Tyr Ser
 1               5              10               15
Trp Trp Ser Asp Gly Gly Ala Gln Ala Thr Tyr Thr Asn Leu Glu Gly
                20              25               30
Gly Thr Tyr Glu Ile Ser Trp Gly Asp Gly Gly Asn Leu Val Gly Gly
            35              40              45
Lys Gly Trp Asn Pro Gly Leu Asn Ala Arg Ala Ile His Phe Glu Gly
 50              55              60
Val Tyr Gln Pro Asn Gly Asn Ser Tyr Leu Ala Val Tyr Gly Trp Thr
 65              70              75              80
Arg Asn Pro Leu Val Glu Tyr Tyr Ile Val Glu Asn Phe Gly Thr Tyr
                85              90              95
Asp Pro Ser Ser Gly Ala Thr Asp Leu Gly Thr Val Glu Cys Asp Gly
                100             105             110
Ser Ile Tyr Arg Leu Gly Lys Thr Thr Arg Val Asn Ala Pro Ser Ile
            115             120             125
Asp Gly Thr Gln Thr Phe Asp Gln Tyr Trp Ser Val Arg Gln Asp Lys
 130             135             140
Arg Thr Ser Gly Thr Val Gln Thr Gly Cys His Phe Asp Ala Trp Ala
145             150             155             160
Arg Ala Gly Leu Asn Val Asn Gly Asp His Tyr Tyr Gln Ile Val Ala
                165             170             175
Thr Glu Gly Tyr Phe Ser Ser Gly Tyr Ala Arg Ile Thr Val Ala Asp
                180             185             190
Val Gly
```

```
<210> SEQ ID NO 21
<211> LENGTH: 76
<212> TYPE: DNA
<213> ORGANISM: Artificial Sequence
<220> FEATURE:
<223> OTHER INFORMATION: Trx-1

<400> SEQUENCE: 21
ctagctaagg aggctgcaga tgcaaacaat acaaccagga accggttaca acaacggtta      60
cttttacagc tattgg                                                     76

<210> SEQ ID NO 22
<211> LENGTH: 78
<212> TYPE: DNA
<213> ORGANISM: Artificial Sequence
<220> FEATURE:
<223> OTHER INFORMATION: XyTv-2

<400> SEQUENCE: 22
aacgatggcc atggtggtgt tacctataca acgggcccg gaggccaatt tagcgtcaat       60
tggtctaact ccggaaac                                                   78

<210> SEQ ID NO 23
<211> LENGTH: 78
<212> TYPE: DNA
<213> ORGANISM: Artificial Sequence
<220> FEATURE:
<223> OTHER INFORMATION: Trx-3

<400> SEQUENCE: 23
ttcgtaggtg aaaaggttg gcaacccggg accaaaaata aggtgatcaa cttctctgga       60
tcttataatc cgaatggg                                                   78

<210> SEQ ID NO 24
<211> LENGTH: 74
<212> TYPE: DNA
<213> ORGANISM: Artificial Sequence
<220> FEATURE:
<223> OTHER INFORMATION: XyTv-4

<400> SEQUENCE: 24
aattcatact taagcgtcta tggctggtct agaaacccac tgattgaata ttacattgtc      60
gaaaatttcg gtac                                                       74

<210> SEQ ID NO 25
<211> LENGTH: 51
<212> TYPE: DNA
<213> ORGANISM: Artificial Sequence
<220> FEATURE:
<223> OTHER INFORMATION: Trx-8

<400> SEQUENCE: 25
gattcctccg acgtctacgt ttgttatgtt ggtccttggc caatgttgtt g               51

<210> SEQ ID NO 26
<211> LENGTH: 84
<212> TYPE: DNA
<213> ORGANISM: Artificial Sequence
<220> FEATURE:
<223> OTHER INFORMATION: XyTv-7

<400> SEQUENCE: 26
ccaatgaaaa tgtcgataac cttgctaccg gtaccaccac aatggatatg tttgcccggg      60
```
cctccggtta aatcgcagtt aacc                                           84

<210> SEQ ID NO 27
<211> LENGTH: 78
<212> TYPE: DNA
<213> ORGANISM: Artificial Sequence
<220> FEATURE:
<223> OTHER INFORMATION: Trx-6

<400> SEQUENCE: 27
agattgaggc ctttgaagca tccacctttt ccaaccgttg ggccctggtt tttattccac    60
tagttgaaga gacctaga                                                  78

<210> SEQ ID NO 28
<211> LENGTH: 85
<212> TYPE: DNA
<213> ORGANISM: Artificial Sequence
<220> FEATURE:
<223> OTHER INFORMATION: XyTv-5

<400> SEQUENCE: 28
atattaggct taccct taag tatgaattcg cagataccga ccagatcttt gggtgactaa    60
cttataatgt aacagctttt aaagc                                          85

<210> SEQ ID NO 29
<211> LENGTH: 58
<212> TYPE: DNA
<213> ORGANISM: Artificial Sequence
<220> FEATURE:
<223> OTHER INFORMATION: XyTv-101

<400> SEQUENCE: 29
tcgacaattt cggtacctac aatccgagta ccggcgccac aaaattaggc gaagtcac      58

<210> SEQ ID NO 30
<211> LENGTH: 53
<212> TYPE: DNA
<213> ORGANISM: Artificial Sequence
<220> FEATURE:
<223> OTHER INFORMATION: XyTv-102

<400> SEQUENCE: 30
tagtgatgga tccgtatatg atatctaccg tacccaacgc gttaatcagc cat           53

<210> SEQ ID NO 31
<211> LENGTH: 59
<212> TYPE: DNA
<213> ORGANISM: Artificial Sequence
<220> FEATURE:
<223> OTHER INFORMATION: Trx-103

<400> SEQUENCE: 31
cgatcattgg aaccgccacc ttttatcagt actggagtgt tagacgtaat catcggagc     59

<210> SEQ ID NO 32
<211> LENGTH: 69
<212> TYPE: DNA
<213> ORGANISM: Artificial Sequence
<220> FEATURE:
<223> OTHER INFORMATION: XyTv-104

<400> SEQUENCE: 32
tccggttcgg ttaatactgc gaatcacttt aatgcatggg cacagcaagg gttaaccta     60

```
ggtacaatg                                                           69

<210> SEQ ID NO 33
<211> LENGTH: 67
<212> TYPE: DNA
<213> ORGANISM: Artificial Sequence
<220> FEATURE:
<223> OTHER INFORMATION: XyTv-105

<400> SEQUENCE: 33
gattatcaaa tcgtagcggt ggaaggctac ttctcgagtg gttccgctag tattacagtg    60
agctaaa                                                             67

<210> SEQ ID NO 34
<211> LENGTH: 73
<212> TYPE: DNA
<213> ORGANISM: Artificial Sequence
<220> FEATURE:
<223> OTHER INFORMATION: XyTv-110

<400> SEQUENCE: 34
gttaaagcca tggatgttag gctcatggcc gcggtgtttt aatccgcttc agtgatcact    60
acctaggcat ata                                                      73

<210> SEQ ID NO 35
<211> LENGTH: 54
<212> TYPE: DNA
<213> ORGANISM: Artificial Sequence
<220> FEATURE:
<223> OTHER INFORMATION: XyTv-109

<400> SEQUENCE: 35
ctatagatgg catgggttgc gcaattagtc ggtagctagt aaccttggcg gtgg          54

<210> SEQ ID NO 36
<211> LENGTH: 60
<212> TYPE: DNA
<213> ORGANISM: Artificial Sequence
<220> FEATURE:
<223> OTHER INFORMATION: XyTv-108

<400> SEQUENCE: 36
aaaatagtca tgacctcaca atctgcatta gtagcctcga ggccaagcca attatgacgc    60

<210> SEQ ID NO 37
<211> LENGTH: 66
<212> TYPE: DNA
<213> ORGANISM: Artificial Sequence
<220> FEATURE:
<223> OTHER INFORMATION: XyTv-107

<400> SEQUENCE: 37
ttagtgaaat tacgtacccg tgtcgttccc aattgggatc catgttacct aatagtttag    60
catcgc                                                              66

<210> SEQ ID NO 38
<211> LENGTH: 53
<212> TYPE: DNA
<213> ORGANISM: Artificial Sequence
<220> FEATURE:
<223> OTHER INFORMATION: XyTv-106

<400> SEQUENCE: 38
caccttccga tgaagagctc accaaggcga tcataatgtc actcgatttc tag           53
```

<210> SEQ ID NO 39
<211> LENGTH: 596
<212> TYPE: DNA
<213> ORGANISM: Artificial Sequence
<220> FEATURE:
<223> OTHER INFORMATION: TrX

<400> SEQUENCE: 39

```
ctagctaagg aggctgcaga tgcaaacaat acaaccagga accggttaca acaacggtta      60
cttttacagc tattggaacg atggccatgg tggtgttacc tatacaaacg ggcccggagg     120
ccaatttagc gtcaattggt ctaactccgg aaacttcgta ggtggaaaag gttggcaacc     180
cgggaccaaa aataaggtga tcaacttctc tggatcttat aatccgaatg ggaattcata     240
cttaagcgtc tatggctggt ctagaaaccc actgattgaa tattacattg tcgaaaattt     300
cggtacctac aatccgagta ccggcgccac aaaaattagg cgaagtcacta gtgatggatc     360 cgtatatgat atctaccgta cccaacgcgt taatcagcca tcgatcattg gaaccgccac     420
cttttatcag tactggagtg ttagacgtaa tcatcggagc tccggttcgg ttaatactgc     480
gaatcacttt aatgcatggg cacagcaagg gttaacccta ggtacaatgg attatcaaat     540
cgtagcggtg gaaggctact ctcgagtggt tccgctagt attacagtga gctaaa         596
```

<210> SEQ ID NO 40
<211> LENGTH: 36
<212> TYPE: DNA
<213> ORGANISM: Artificial Sequence
<220> FEATURE:
<223> OTHER INFORMATION: Tx-75A-1

<400> SEQUENCE: 40

```
tgggaattca tacttagccg tctatggctg gtctag                                36
```

<210> SEQ ID NO 41
<211> LENGTH: 42
<212> TYPE: DNA
<213> ORGANISM: Artificial Sequence
<220> FEATURE:
<223> OTHER INFORMATION: Tx-105H-1

<400> SEQUENCE: 41

```
accggcgcca caaaacacgg cgaagtcact agtgatggat cc                         42
```

<210> SEQ ID NO 42
<211> LENGTH: 44
<212> TYPE: DNA
<213> ORGANISM: Artificial Sequence
<220> FEATURE:
<223> OTHER INFORMATION: Tx-C1

<400> SEQUENCE: 42

```
ccaaggcgat cataatgtca ctcgatttct agaacttcga accc                       44
```

<210> SEQ ID NO 43
<211> LENGTH: 36
<212> TYPE: DNA
<213> ORGANISM: Artificial Sequence
<220> FEATURE:
<223> OTHER INFORMATION: Tx-del(123-144)-1r

<400> SEQUENCE: 43

```
cggagctccg acgcgttggg tacggtagat atcata                                36
```

<210> SEQ ID NO 44
<211> LENGTH: 42
<212> TYPE: DNA
<213> ORGANISM: Artificial Sequence
<220> FEATURE:
<223> OTHER INFORMATION: Tx-105R-1

<400> SEQUENCE: 44
accggcgcca caaaaagagg cgaagtcact agtgatggat cc                    42

<210> SEQ ID NO 45
<211> LENGTH: 41
<212> TYPE: DNA
<213> ORGANISM: Artificial Sequence
<220> FEATURE:
<223> OTHER INFORMATION: Tx-N1

<400> SEQUENCE: 45
ctagctaagg aggctgcaga tgcaaacaat acaaccagga a                     41

<210> SEQ ID NO 46
<211> LENGTH: 36
<212> TYPE: DNA
<213> ORGANISM: Artificial Sequence
<220> FEATURE:
<223> OTHER INFORMATION: Tx-75-G1

<400> SEQUENCE: 46
tgggaattca tacttaggcg tctatggctg gtctag                           36

<210> SEQ ID NO 47
<211> LENGTH: 66
<212> TYPE: DNA
<213> ORGANISM: Artificial Sequence
<220> FEATURE:
<223> OTHER INFORMATION: Tx-144R-1r

<400> SEQUENCE: 47
ccatgcatta aagtgattcg cagtattaac cgaaccggag ctccgacgat tacgtctaac 60
actcca                                                           66

<210> SEQ ID NO 48
<211> LENGTH: 44
<212> TYPE: DNA
<213> ORGANISM: Artificial Sequence
<220> FEATURE:
<223> OTHER INFORMATION: Tx-161R-1r

<400> SEQUENCE: 48
gtacctaggg ttaacccttg ccgtgcccat gcattaaagt gatt                  44

<210> SEQ ID NO 49
<211> LENGTH: 40
<212> TYPE: DNA
<213> ORGANISM: Artificial Sequence
<220> FEATURE:
<223> OTHER INFORMATION: Tx-125A 129E-1

<400> SEQUENCE: 49
ccaacgcgtt aatgcgccat cgatcgaggg aaccgccacc                       40

<210> SEQ ID NO 50
<211> LENGTH: 26
<212> TYPE: DNA
<213> ORGANISM: Artificial Sequence

```
<220> FEATURE:
<223> OTHER INFORMATION: Tx-116G-1

<400> SEQUENCE: 50
gacggatccg tatatggtat ctaccg                                           26

<210> SEQ ID NO 51
<211> LENGTH: 36
<212> TYPE: DNA
<213> ORGANISM: Artificial Sequence
<220> FEATURE:
<223> OTHER INFORMATION: Tx-118C-1

<400> SEQUENCE: 51
gacggatccg tatatgatat ctgccgtacc caacgc                                36

<210> SEQ ID NO 52
<211> LENGTH: 39
<212> TYPE: DNA
<213> ORGANISM: Artificial Sequence
<220> FEATURE:
<223> OTHER INFORMATION: Tx-10H11D-1

<400> SEQUENCE: 52
ggaaccggtt accacgacgg ttacttttac agctattgg                             39

<210> SEQ ID NO 53
<211> LENGTH: 36
<212> TYPE: DNA
<213> ORGANISM: Artificial Sequence
<220> FEATURE:
<223> OTHER INFORMATION: Tx-116G118C-1

<400> SEQUENCE: 53
gacggatccg tatatggtat ctgccgtacc caacgc                                36

<210> SEQ ID NO 54
<211> LENGTH: 184
<212> TYPE: PRT
<213> ORGANISM: Aspergillus kawachii

<400> SEQUENCE: 54
```

Ser Ala Gly Ile Asn Tyr Val Gln Asn Tyr Asn Gly Asn Leu Ala Asp
1               5                   10                  15

Phe Thr Tyr Asp Glu Ser Ala Gly Thr Phe Ser Met Tyr Trp Glu Asp
            20                  25                  30

Gly Val Ser Ser Asp Phe Val Val Gly Leu Gly Trp Thr Thr Gly Ser
        35                  40                  45

Ser Asn Ala Ile Ser Tyr Ser Ala Glu Tyr Ser Ala Ser Gly Ser Ser
    50                  55                  60

Ser Tyr Leu Ala Val Tyr Gly Trp Val Asn Tyr Pro Gln Ala Glu Tyr
65                  70                  75                  80

Tyr Ile Val Glu Asp Tyr Gly Asp Tyr Asn Pro Cys Ser Ser Ala Thr
                85                  90                  95

Ser Leu Gly Thr Val Tyr Ser Asp Gly Ser Thr Tyr Gln Val Cys Thr
            100                 105                 110

Asp Thr Arg Thr Asn Glu Pro Ser Ile Thr Gly Thr Ser Thr Phe Thr
        115                 120                 125

Gln Tyr Phe Ser Val Arg Glu Ser Thr Arg Thr Ser Gly Thr Val Thr
    130                 135                 140

Val Ala Asn His Phe Asn Phe Trp Ala Gln His Gly Phe Gly Asn Ser

```
                145                 150                 155                 160
Asp Phe Asn Tyr Gln Val Met Ala Val Glu Ala Trp Ser Gly Ala Gly
                165                 170                 175
Ser Ala Ser Val Thr Ile Ser Ser
                180

<210> SEQ ID NO 55
<211> LENGTH: 190
<212> TYPE: PRT
<213> ORGANISM: Artificial Sequence
<220> FEATURE:
<223> OTHER INFORMATION: TrX-H-11D-ML-75A105H-118C-125A129E-144R161R
      (TrX-H-11D-ML-AHCAE-RR)

<400> SEQUENCE: 55

Gln Thr Ile Gln Pro Gly Thr Gly Tyr His Asp Gly Tyr Phe Tyr Ser
1               5                   10                  15

Tyr Trp Asn Asp Gly His Gly Gly Val Thr Met Thr Leu Gly Pro Gly
                20                  25                  30

Gly Gln Phe Ser Val Asn Trp Ser Asn Ser Gly Asn Phe Val Gly Gly
            35                  40                  45

Lys Gly Trp Gln Pro Gly Thr Lys Asn Lys Val Ile Asn Phe Ser Gly
        50                  55                  60

Ser Tyr Asn Pro Asn Gly Asn Ser Tyr Leu Ala Val Tyr Gly Trp Ser
65                  70                  75                  80

Arg Asn Pro Leu Ile Glu Tyr Tyr Ile Val Glu Asn Phe Gly Thr Tyr
                85                  90                  95

Asn Pro Ser Thr Gly Ala Thr Lys His Gly Glu Val Thr Ser Asp Gly
                100                 105                 110

Ser Val Tyr Asp Ile Cys Arg Thr Gln Arg Val Asn Ala Pro Ser Ile
            115                 120                 125

Glu Gly Thr Ala Thr Phe Tyr Gln Tyr Trp Ser Val Arg Arg Asn Arg
        130                 135                 140

Arg Ser Ser Gly Ser Val Asn Thr Ala Asn His Phe Asn Ala Trp Ala
145                 150                 155                 160

Arg Gln Gly Leu Thr Leu Gly Thr Met Asp Tyr Gln Ile Val Ala Val
                165                 170                 175

Glu Gly Tyr Phe Ser Ser Gly Ser Ala Ser Ile Thr Val Ser
                180                 185                 190

<210> SEQ ID NO 56
<211> LENGTH: 112
<212> TYPE: DNA
<213> ORGANISM: Artificial Sequence
<220> FEATURE:
<223> OTHER INFORMATION: TrX-HML

<400> SEQUENCE: 56
ctagctaagg aggctgcaga tgcaaacaat acaaccagga accggttacc acaacggtta      60
cttttacagc tattggaacg atggccatgg aggcgtcaca atgactctgg gg             112

<210> SEQ ID NO 57
<211> LENGTH: 30
<212> TYPE: PRT
<213> ORGANISM: Artificial Sequence
<220> FEATURE:
<223> OTHER INFORMATION: TrX-HML

<400> SEQUENCE: 57
```

-continued

Gln Thr Ile Gln Pro Gly Thr Gly Tyr His Asn Gly Tyr Phe Tyr Ser
1               5                   10                  15

Tyr Trp Asn Asp Gly His Gly Gly Val Thr Met Thr Leu Gly
            20                  25                  30

<210> SEQ ID NO 58
<211> LENGTH: 14
<212> TYPE: PRT
<213> ORGANISM: Artificial Sequence
<220> FEATURE:
<223> OTHER INFORMATION: TX-105R-1

<400> SEQUENCE: 58

Thr Gly Ala Thr Lys Arg Gly Glu Val Thr Ser Asp Gly Ser
1               5                   10

<210> SEQ ID NO 59
<211> LENGTH: 8
<212> TYPE: PRT
<213> ORGANISM: Artificial Sequence
<220> FEATURE:
<223> OTHER INFORMATION: TX-C1

<400> SEQUENCE: 59

Gly Ser Ala Ser Ile Thr Val Ser
1               5

<210> SEQ ID NO 60
<211> LENGTH: 13
<212> TYPE: PRT
<213> ORGANISM: Artificial Sequence
<220> FEATURE:
<223> OTHER INFORMATION: TX-75A-1

<400> SEQUENCE: 60

Asn Gly Asn Ser Tyr Leu Ala Val Tyr Gly Trp Ser Arg
1               5                   10

<210> SEQ ID NO 61
<211> LENGTH: 13
<212> TYPE: PRT
<213> ORGANISM: Artificial Sequence
<220> FEATURE:
<223> OTHER INFORMATION: TX-75G-1

<400> SEQUENCE: 61

Asn Gly Asn Ser Tyr Leu Gly Val Tyr Gly Trp Ser Arg
1               5                   10

<210> SEQ ID NO 62
<211> LENGTH: 13
<212> TYPE: PRT
<213> ORGANISM: Artificial Sequence
<220> FEATURE:
<223> OTHER INFORMATION: TX125A129E-1

<400> SEQUENCE: 62

Gln Arg Val Asn Ala Pro Ser Ile Glu Gly Thr Ala Thr
1               5                   10

<210> SEQ ID NO 63
<211> LENGTH: 14
<212> TYPE: PRT
<213> ORGANISM: Artificial Sequence
<220> FEATURE:
<223> OTHER INFORMATION: TX-105H-1

-continued

```
<400> SEQUENCE: 63

Thr Gly Ala Thr Lys His Gly Glu Val Thr Ser Asp Gly Ser
1               5                   10

<210> SEQ ID NO 64
<211> LENGTH: 12
<212> TYPE: PRT
<213> ORGANISM: Artificial Sequence
<220> FEATURE:
<223> OTHER INFORMATION: TX-del (123-144)-1r

<400> SEQUENCE: 64

Gly Ser Ser Arg Arg Gln Thr Arg Tyr Ile Asp Tyr
1               5                   10

<210> SEQ ID NO 65
<211> LENGTH: 7
<212> TYPE: PRT
<213> ORGANISM: Artificial Sequence
<220> FEATURE:
<223> OTHER INFORMATION: TX-N1

<400> SEQUENCE: 65

Gln Thr Ile Gln Pro Gly Thr
1               5

<210> SEQ ID NO 66
<211> LENGTH: 22
<212> TYPE: PRT
<213> ORGANISM: Artificial Sequence
<220> FEATURE:
<223> OTHER INFORMATION: TX-144R-1r

<400> SEQUENCE: 66

Trp Ala Asn Phe His Asn Ala Thr Asn Val Ser Gly Ser Ser Arg Arg
1               5                   10                  15

Asn Arg Arg Val Ser Trp
            20

<210> SEQ ID NO 67
<211> LENGTH: 15
<212> TYPE: PRT
<213> ORGANISM: Artificial Sequence
<220> FEATURE:
<223> OTHER INFORMATION: TX-161R-1r

<400> SEQUENCE: 67

Thr Gly Leu Thr Leu Gly Gln Arg Ala Trp Ala Asn Phe His Asn
1               5                   10                  15

<210> SEQ ID NO 68
<211> LENGTH: 9
<212> TYPE: PRT
<213> ORGANISM: Artificial Sequence
<220> FEATURE:
<223> OTHER INFORMATION: TX-116G-1

<400> SEQUENCE: 68

Asp Gly Ser Val Tyr Gly Ile Tyr Arg
1               5

<210> SEQ ID NO 69
<211> LENGTH: 12
<212> TYPE: PRT
<213> ORGANISM: Artificial Sequence
<220> FEATURE:
```

```
<223> OTHER INFORMATION: TX-118C-1

<400> SEQUENCE: 69

Asp Gly Ser Val Tyr Asp Ile Cys Arg Thr Gln Arg
1               5                   10

<210> SEQ ID NO 70
<211> LENGTH: 13
<212> TYPE: PRT
<213> ORGANISM: Artificial Sequence
<220> FEATURE:
<223> OTHER INFORMATION: TX-10H11D-1

<400> SEQUENCE: 70

Gly Thr Gly Tyr His Asp Gly Tyr Phe Tyr Ser Tyr Trp
1               5                   10

<210> SEQ ID NO 71
<211> LENGTH: 12
<212> TYPE: PRT
<213> ORGANISM: Artificial Sequence
<220> FEATURE:
<223> OTHER INFORMATION: TX-116G118C-1

<400> SEQUENCE: 71

Asp Gly Ser Val Tyr Gly Ile Cys Arg Thr Gln Arg
1               5                   10
```